United States Patent [19]

Shishido et al.

[11] Patent Number: 5,539,514

[45] Date of Patent: Jul. 23, 1996

[54] FOREIGN PARTICLE INSPECTION APPARATUS AND METHOD WITH FRONT AND BACK ILLUMINATION

[75] Inventors: Hiroaki Shishido; Shunichi Matsumoto, both of Yokohama, Japan

[73] Assignee: Hitachi, Ltd., Tokyo, Japan

[21] Appl. No.: 269,379

[22] Filed: Jun. 30, 1994

Related U.S. Application Data

[63] Continuation-in-part of Ser. No. 192,036, Feb. 4, 1994, and a continuation-in-part of Ser. No. 902,819, Jun. 23, 1992, Pat. No. 5,410,400.

[30] Foreign Application Priority Data

Jun. 30, 1993 [JP] Japan .................. 5-160912

[51] Int. Cl.⁶ .................................................. G01N 21/00
[52] U.S. Cl. ........................................ 356/237; 356/240
[58] Field of Search ........................................ 356/237, 240

[56] References Cited

U.S. PATENT DOCUMENTS

| | | | |
|---|---|---|---|
| 4,922,308 | 5/1990 | Noguchi et al. | 356/237 |
| 4,952,058 | 8/1990 | Noguchi et al. | 356/237 |
| 5,098,191 | 3/1992 | Noguchi et al. | 356/237 |

FOREIGN PATENT DOCUMENTS

| | | | |
|---|---|---|---|
| 63-006444 | 1/1988 | Japan | 356/237 |
| 63-006442 | 1/1988 | Japan | 356/237 |
| 63-006443 | 1/1988 | Japan | 356/237 |
| 63-315936 | 12/1988 | Japan | 356/237 |
| 63-266036 | 4/1990 | Japan | 356/237 |

*Primary Examiner*—Frank Gonzalez
*Assistant Examiner*—Jason D. Eisenberg
*Attorney, Agent, or Firm*—Antonelli, Terry, Stout & Kraus

[57] ABSTRACT

A method of inspecting a phase shift reticle comprising a transparent or translucent substrate, a circuit pattern of an opaque film formed on the front surface of the substrate and a pattern of a transparent or translucent film formed on the front surface of the substrate comprises: obliquely projecting a front illuminating light beam on the front surface of the substrate by a front illuminating system; concentrating scattered light scattered by the surface of the substrate and the surfaces of the patterns, obliquely projecting a back illuminating light beam on the back surface of the substrate by a back illuminating system, concentrating transmitted-and-diffracted light transmitted and diffracted by the substrate and the patterns; intercepting the scattered light scattered by the patterns and the transmitted-and-diffracted light transmitted and diffracted by the patterns with spatial filters disposed on Fourier transform planes, focusing the scattered light and the transmitted-and-diffracted light transmitted by the spatial filters on detectors; and comparing detection signals provided by the detectors to see if there are any foreign particles on the phase shift reticle.

28 Claims, 57 Drawing Sheets

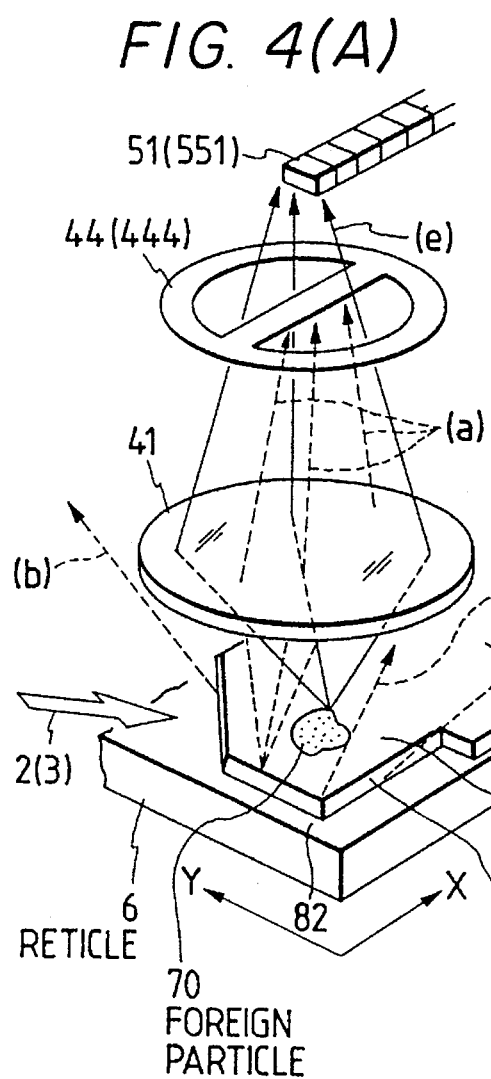
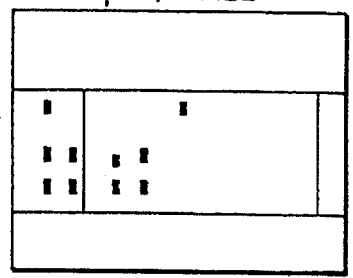
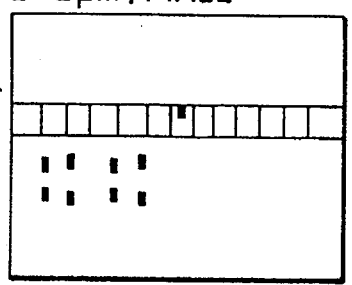
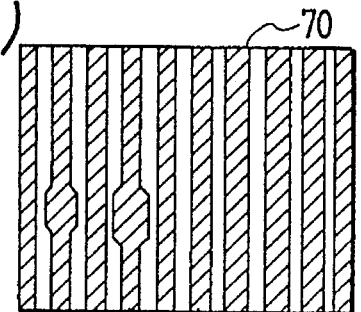

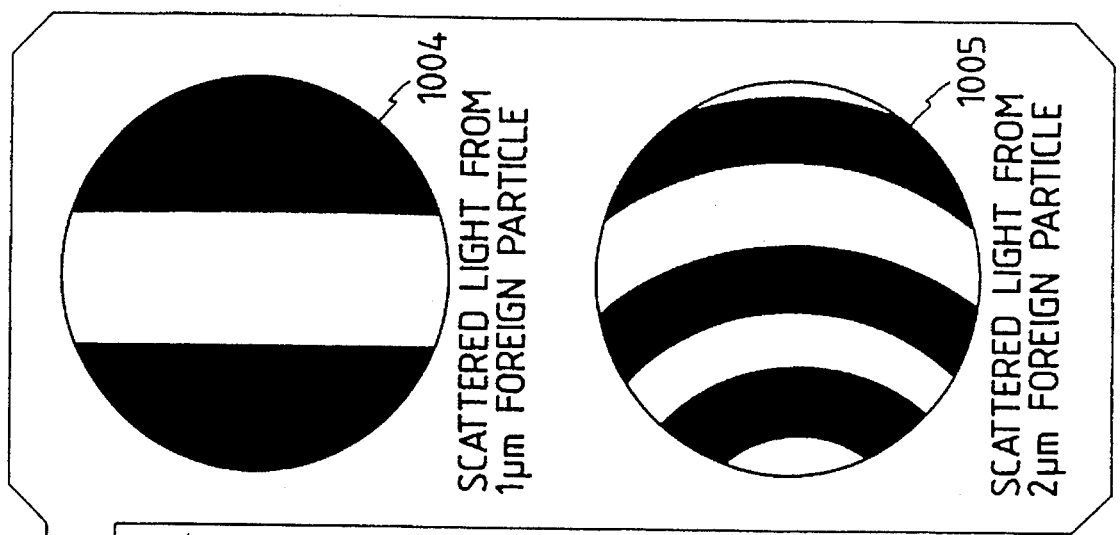
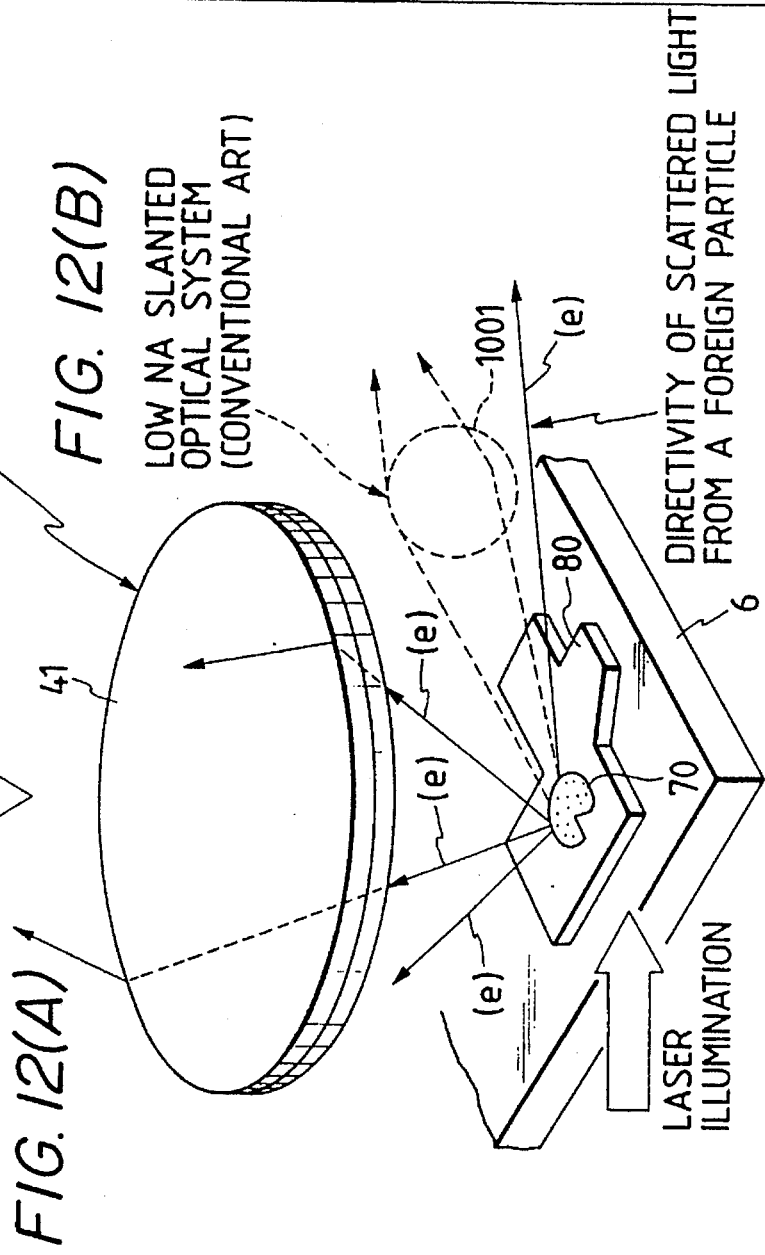

2. BACK ILLUMINATION MODE

1. FRONT ILLUMINATION MODE

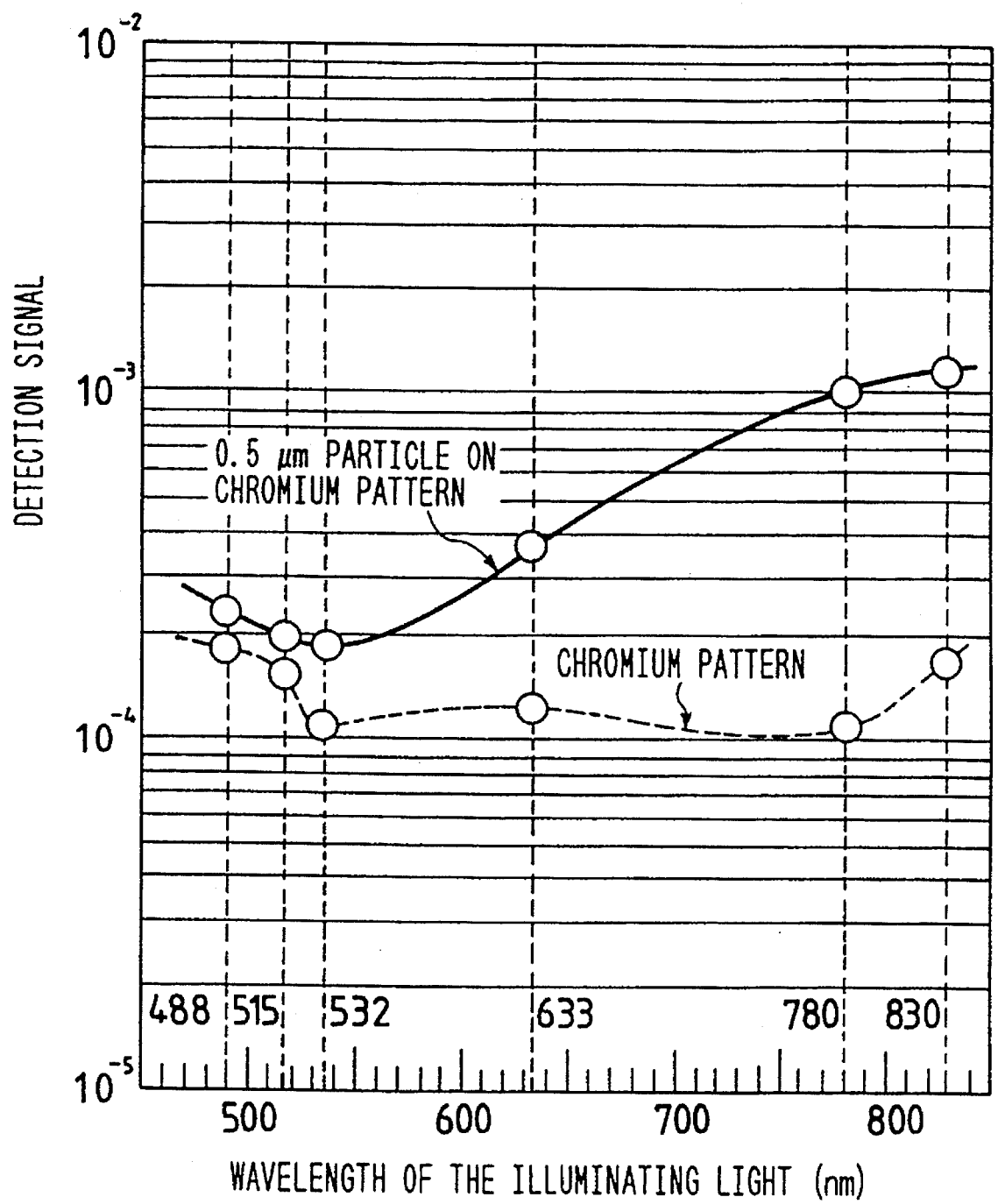

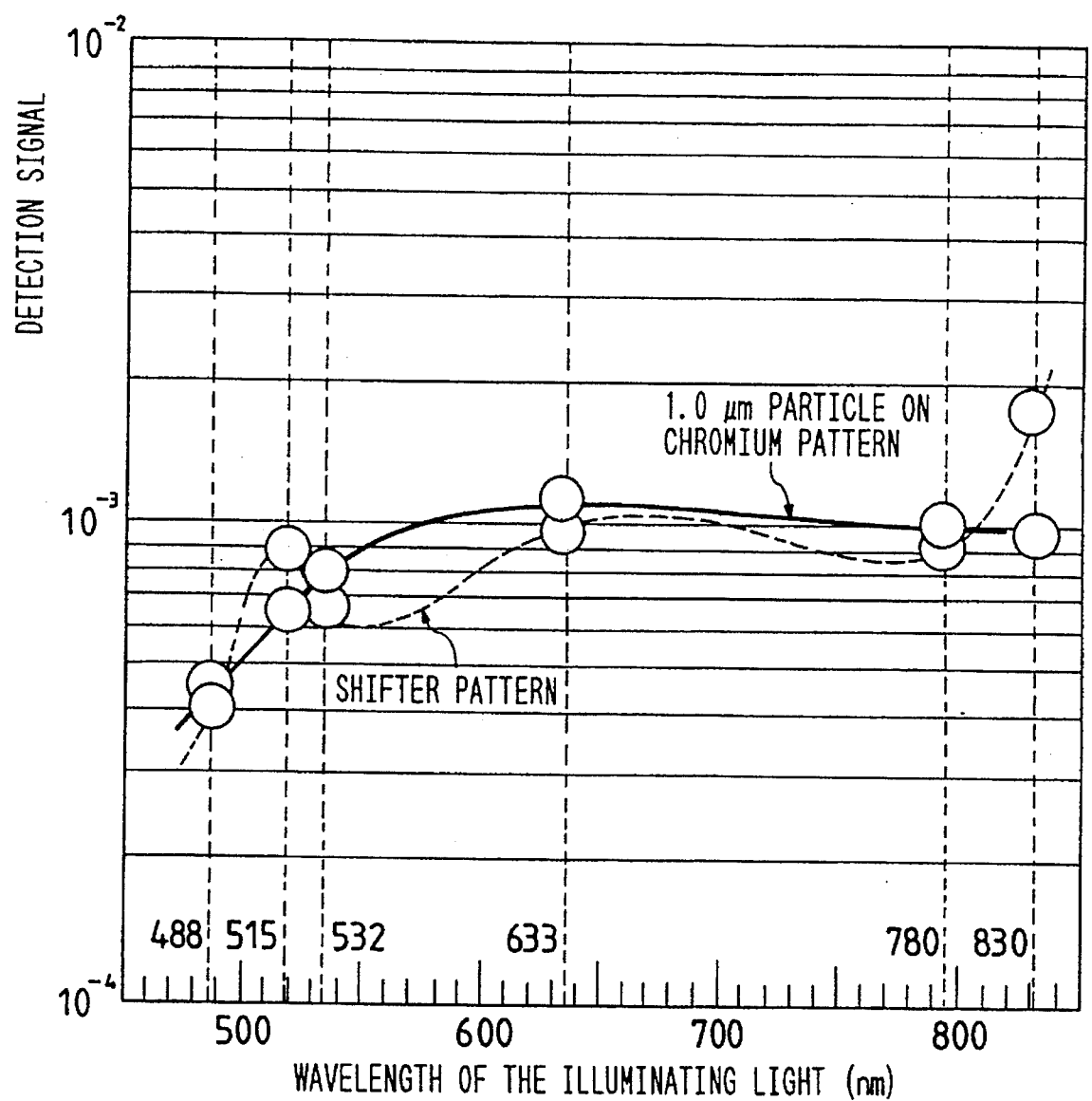

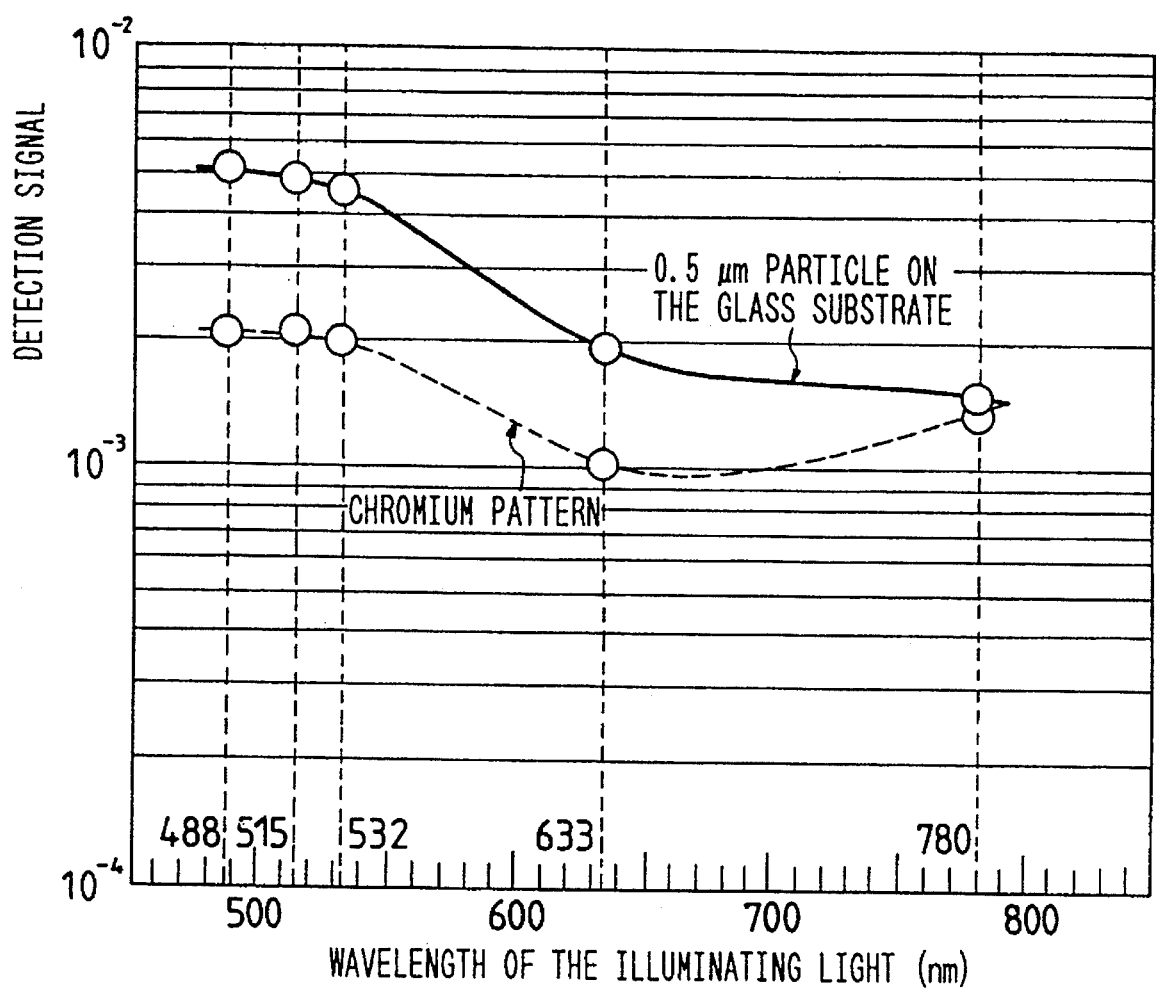

MEASURED RESULT
OF SHADING

COMPENSATED DATA
OF SHADING

DETECTED SIGNAL FROM A
COMPENSATED DETECTOR

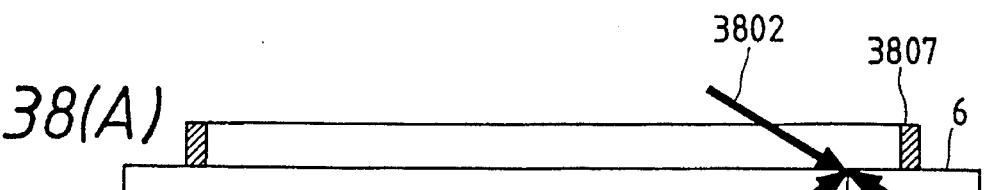
FIG. 38(A)
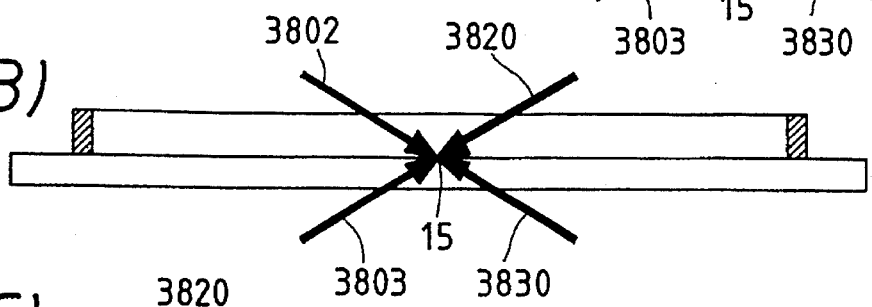
FIG. 38(B)
FIG. 38(C)
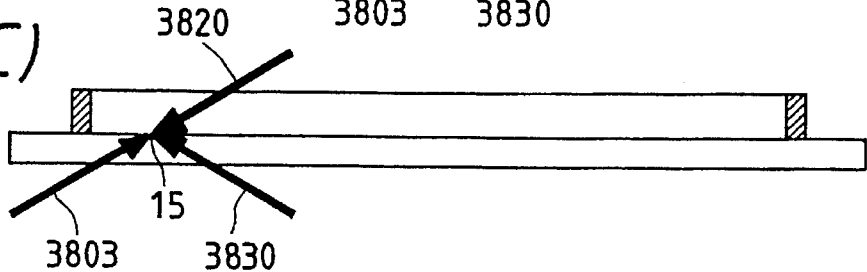
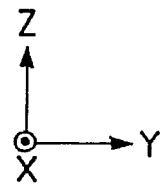
FIG. 39(A)
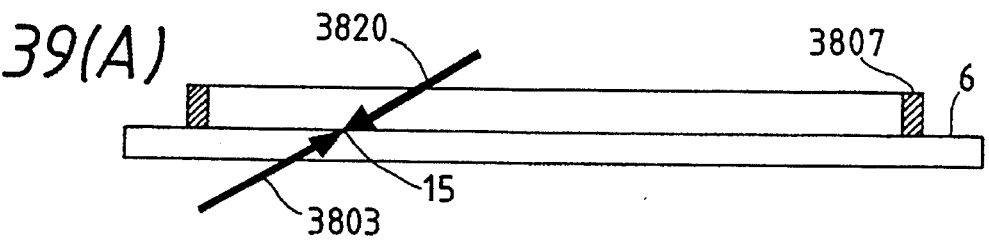
FIG. 39(B)
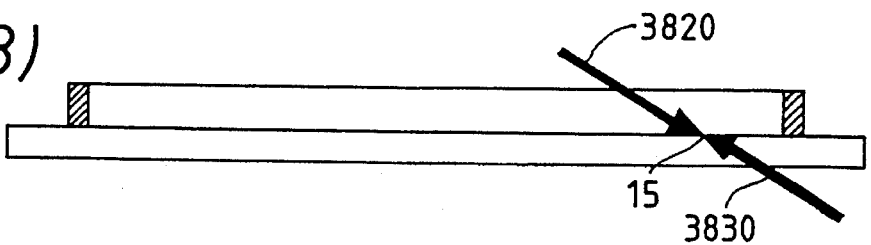
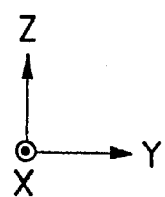

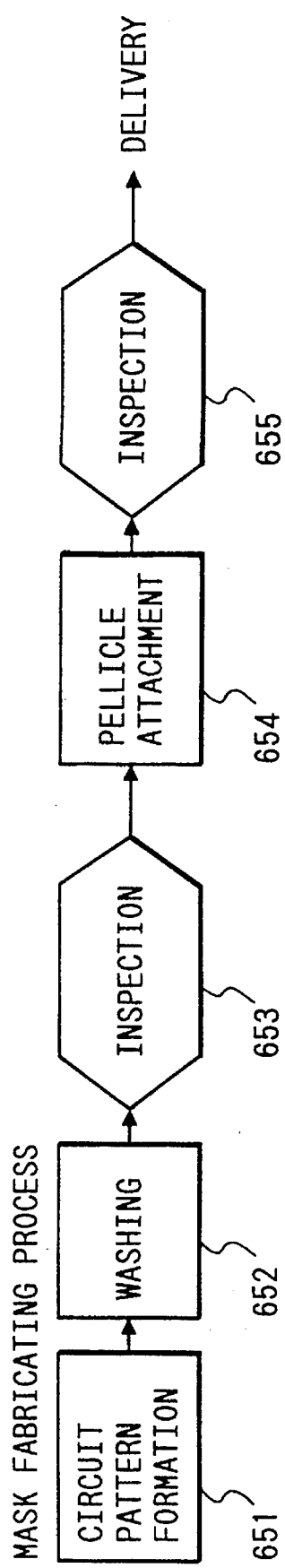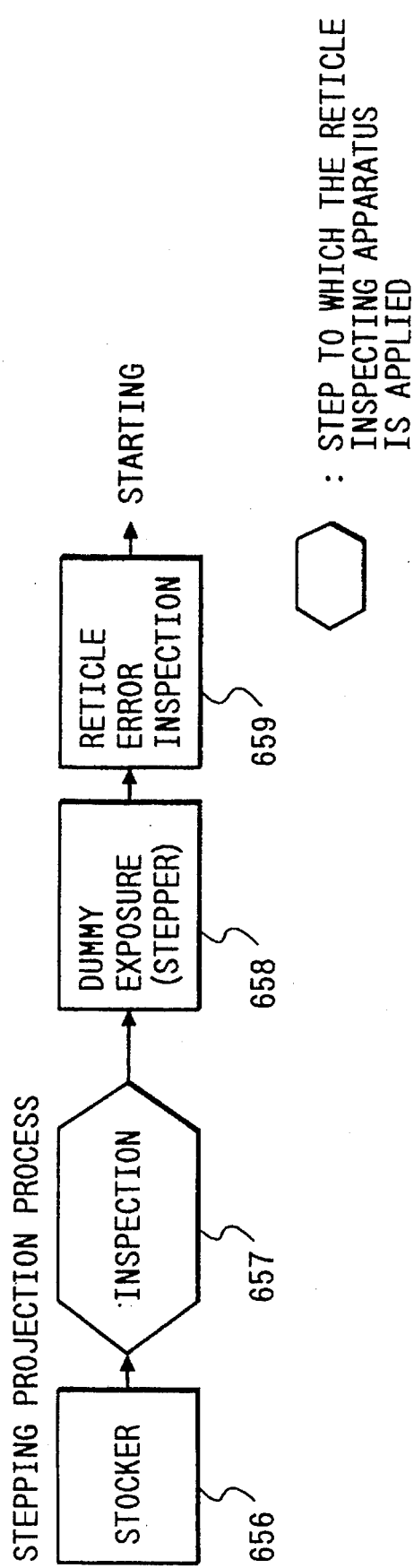

THE MAXIMUM AMONG ① TO ④ IS PROVIDED AT b2

① (a1 + a2) / 2
② (a2 + a3) / 2
③ (b1 + b2) / 2
④ (b2 + b3) / 2
⑤ (a1 + b1) / 2
⑥ (b1 + c1) / 2
⑦ (a2 + b2) / 2
⑧ (b2 + c2) / 2

THE MAXIMUM AMONG ① TO ④ IS PROVIDED AT b2

① a1
② a2
③ b1
④ b2

FOREIGN PARTICLE INSPECTION APPARATUS AND METHOD WITH FRONT AND BACK ILLUMINATION

CROSS-REFERENCE TO RELATED APPLICATIONS

This application is a continuation-in-part of application Ser. No. 08/192,036, filed Feb. 4, 1994, and a continuation-in-part of application Ser. No. 07/902,819, filed Jun. 23, 1992, now U.S. Pat. No. 5,410,400.

BACKGROUND OF THE INVENTION

The present invention relates to a method of inspecting a reticle or a photomask (hereinafter referred to inclusively as "reticle") provided with a circuit pattern and a phase shifter formed of a light-transmissive film for defects, such as foreign particles adhering to the reticle, and, more particularly, to a method of inspecting a reticle provided with phase shifter for defects, such as foreign particles, having sizes on the submicron order before printing the reticle on a wafer, and a reticle inspecting apparatus for carrying out the same reticle inspecting method.

When fabricating LSI chips or printed wiring boards, a reticle having a circuit pattern is inspected for defects before printing the reticle on wafers by a photographic process. If the reticle has minute foreign particles having sizes on the submicron order thereon, the reticle cannot be correctly printed on wafers and, consequently, LSI chips fabricated by using such wafers become defective. Problems attributable to the minute foreign particles adhering to the reticle have become more and more significant with the recent progressive increase in the degree of integration of LSIs and the existence of even foreign particles having sizes on the submicron order on the reticle is not permissible.

The inspection of the reticle for foreign particles before printing the reticle on a wafer is indispensable to preventing defective reticle printing, and various techniques for inspecting the reticle for foreign particles have been proposed. A prevalent method of inspecting a reticle for foreign particles, which is employed widely because of its capability of quick and highly sensitive inspection, irradiates the reticle obliquely with a light beam having a high directivity, such as a laser beam, and detects scattered light scattered by foreign particles. However, since the light beam is diffracted at edges of the pattern of the reticle, the diffracted light and the scattered light scattered by foreign particles must be discriminated from each other. Various technical means for discriminating between the diffracted light and the scattered light have been proposed.

A first previously proposed technical means is an inspecting apparatus disclosed in, for example, Japanese Patent Laid-open (Kokai) No. 54-101390. This inspecting apparatus comprises a laser that emits a linearly polarized laser beam, an irradiating means for irradiating a circuit pattern obliquely with the linearly polarized laser beam so that the linearly polarized laser beam fall on the circuit pattern at a given incidence angle, and an oblique focusing optical system including a polarizing plate and lenses. When the circuit pattern is irradiated with the linearly polarized laser beam, the diffracted light diffracted by the circuit pattern and the scattered light scattered by foreign particles differ from each other in the plane of polarization, i.e., the plane of vibration, therefore, only the light scattered by the foreign particles can be detected.

A second previously proposed technical means is an inspecting apparatus disclosed in, for example, Japanese Patent Laid-open (Kokai) No. 59-65428, 1-117024 or 1-153943. This inspecting apparatus comprises a scanning means for scanning an object with a laser beam obliquely projected on the object, a first lens disposed above the object to condense scattered laser light so that the point of irradiation of the laser beam coincides substantially with the condensing point, a filter plate disposed on the Fourier transform image plane of the first lens to filter regular diffracted light diffracted by the circuit pattern of the object, a second lens for the inverse Fourier transform of the scattered light scattered by the foreign particles and transmitted through the screen plate, a slit plate disposed at the focal point of the second lens to screen scattered light from portions of the object other than a portion corresponding to the point of irradiation with the laser beam, and a light receiving device for receiving the scattered light scattered by the foreign particles and passed through the slit of the slit plate. This inspecting apparatus is based on a fact that generally the elements of a circuit pattern are extended in a single direction or in several directions, and filters the diffracted light diffracted by the elements of the circuit pattern extending in a specified direction by a spatial filter disposed on the Fourier transform image plane to detect only the scattered light scattered by the foreign particles.

A third previously proposed technical means is an arrangement disclosed in, for example, Japanese Patent Laid-open (Kokai) No. 58-62543. This arrangement is based on a fact that diffracted light diffracted by the edges of a circuit pattern is directional light while scattered light scattered by foreign particles is not directional and identifies foreign particles on the basis of the logical product of the outputs of a plurality of obliquely arranged detectors.

A fourth previously proposed technical means is an arrangement disclosed in, for example, Japanese Patent Laid-open (Kokai) No. 60-154634 or 60-154635. This arrangement is based on a fact that diffracted light diffracted by the edges of a circuit pattern converges only along a specific direction while scattered light scattered by foreign particles is scattered in all directions and identifies foreign particles from the outputs of a plurality of detectors.

Apparatuses and methods relating to the inspection of objects for minute foreign particles, such as a schlieren method, a phase-contrast microscope and a technique relating to a diffraction image having a finite size are disclosed in, for example, Hiroshi Kubota, "Oyou Kogaku", Iwanami Zensho, pp. 129–136.

When an array type detector, such as a one-dimensional solid-state imaging device provided with an array of solid-state image sensors, an output signal representing a foreign particle is distributed to a plurality of pixels if the foreign particle corresponds to a plurality of elements of the detector and, consequently, the output of the detector is reduced and therefore there is the possibility that the detector fails in detecting the foreign particle. An invention made to obviate such a possibility, disclosed in Japanese Patent Laid-open (Kokai) No. 61-104242 disposes an array type detector at an angle to the direction of scanning operation of an inspection table. Other inventions made for the same purpose, disclosed in Japanese Patent Laid-open (Kokai) Nos. 61-104244 and 61-104659 employ an array type detector having a unique shape and provided with elements arranged in a unique arrangement.

Irregular illumination and the variation of illumination affects adversely to the repeatability and accuracy of detection. An invention disclose in Japanese Patent Laid-open (Kokai) No. 60-038827 calibrates the intensity of scattered light automatically by using a standard sample having a known characteristics.

Japanese Patent laid-open (Kokai) No. 56-132549 discloses an invention for obviating misidentifying a large amount of scattered light scattered by a comparatively large foreign particle as scattered light scattered by a plurality of comparatively small foreign particles.

As mentioned above, failure in finding foreign particles which affect adversely to the quality of LSI chips has become a significant problem with the reduction of the size of foreign particles to be detected. The first previously proposed technical means, for example, the invention disclosed in Japanese Patent Laid-open (Kokai) No. 54-101390, is unable to detect minute foreign particles because the difference between the plane of polarization of the scattered light scattered by minute foreign particles and the plane of polarization of the diffracted light diffracted by the edges of the circuit pattern is small.

The second previously proposed technical means, for example, the inventions disclosed in Japanese Patent Laid-open (Kokai) Nos. 59-65428, 1-117024 and 1-153943, detect only the scattered light scattered by foreign particles by separating the scattered light scattered by foreign particles from the diffracted light diffracted by the circuit pattern with the filter plate and the slit plate. Although these inventions uses a detecting mechanism for detecting foreign particles by a simple binary method having a simple configuration to their advantage, the diffracted light diffracted by the intersection of the elements of the circuit pattern does not travel unidirectionally like the diffracted light diffracted by the straight edge of the circuit pattern, and hence the spatial filter is unable to filter the diffracted light diffracted by the intersection of the elements of the circuit pattern perfectly. Furthermore, since the diffracted light diffracted by a minute circuit pattern on the micron order for a LSI having a very high degree of integration is analogous in behavior to the scattered light scattered by foreign particles and hence it is practically difficult to discriminate between the circuit pattern and foreign particles by a simple binary method.

The apparatus proposed as the third previously proposed technical means in, for example, Japanese Patent Laid-open (Kokai) No. 58-62543) and the those proposed as the fourth previously proposed technical means in, for example, Japanese Patent Laid-open (Kokai) Nos. 60-154634 and 60-154635 have difficulty in employing an optical system having a sufficiently high condensing ability because of their configurations and hence it is practically difficult for these apparatuses to detect faint scattered light scattered by foreign particles.

The apparatuses disclosed as the fifth previously proposed technical means in, for example, Japanese Patent Laid-open (Kokai) Nos. 61-104242 and 61- 104244 need a special detector and a special optical system, which are costly.

The apparatus disclosed as the sixth previously proposed technical means in, for example, Japanese Patent Laid-open (Kokai) No. 60-038827 has drawbacks in application to an array type detector suitable for quick detection and in structural accuracy for detecting minute foreign particles.

The apparatus disclosed as the seventh previously proposed technical means in, for example, Japanese Patent Laid-open (Kokai) No. 56-132544 detects only a single point on a large foreign particle and hence the apparatus is unable to recognize the shape of an elongate foreign particle accurately.

A reticle recently developed to improve resolution in transferring a circuit pattern formed on the reticle is provided with a transparent or translucent thin film, which is called a phase shift film or a phase shifter, having a thickness equal to odd times half the wavelength of the light used for exposure and formed so as to cover spaces between the elements of the circuit pattern. Although this thin film is transparent or translucent, the thickness of this thin film is several times the thickness on the order of 0.1 μm of the circuit pattern. Consequently, the intensity of the diffracted light diffracted by the edges of the thin film is several to several tens times the intensity of the diffracted light diffracted by the edges of the circuit pattern, which reducing the foreign particle detecting sensitivity significantly.

SUMMARY OF THE INVENTION

Accordingly, it is an object of the present invention to provide a method of inspecting a reticle, such as a reticle fabricated by forming a circuit pattern and a phase shift film for improving transfer resolution on a transparent or translucent substrate for defects, such as minute foreign particles having sizes on the submicron order adhering to the circuit pattern, capable of separating the defects from the circuit pattern and of stably detecting the defects, and an apparatus for carrying out the method.

Another object of the present invention is to provide a projection exposure method capable of eliminating defects, such as minute foreign particles, from a mask, such as a reticle provided with a phase-shift film (hereinafter referred to as "phase shift reticle") and of projecting a circuit pattern formed on the mask on a substrate, such as a wafer, by using an image-reducing projection exposure apparatus for exposure, and an apparatus for carrying out the projection exposure method.

The present invention has been made by introducing improvements into the invention proposed in U.S. patent application Ser. No. 08/192,036 related with U.S. patent application Ser. No. 07/902,819 or the invention proposed in Korean Pat. Application No. 3209/1994 related with Korean Pat. Application No. 11092/1992.

With the foregoing object in view, the present invention provides a reticle inspecting apparatus for inspecting a reticle fabricated by forming a circuit pattern on a substrate, for defects, such as foreign particles adhering to the reticle, comprising: a stage unit for supporting the substrate, capable of being optionally moved in directions along an X-axis, a Y-axis and a Z-axis; an illuminating system having a first illuminating system and a second illuminating system individually provided with light sources that emit light beams of approximately 780 nm in wavelength, disposed opposite to each other on the side of the front surface of the substrate provided with the circuit pattern so as to illuminate the substrate with light beams that travel obliquely to the surface of the substrate, either the first or the second illuminating system that can project the light beam on the surface of the substrate so that the light beam is not intercepted by a pellicle holding frame being used; an illuminating system disposed on the opposite side of the reticle with respect to the former illuminating system, having a third illuminating system corresponding to the first illuminating system and a fourth illuminating system corresponding to the second illuminating system, individually provided with light sources that emit light beams of approximately 488 nm in wavelength, the third illuminating system being used when the first illuminating system is used or the fourth illuminating system being used when the second illuminating system is used; a focusing optical system having a high numerical aperture (NA) of 0.4 or above, disposed on the side of the front surface of the substrate provided with the circuit pattern, that does not concentrate directly reflected light and directly transmitted light, concentrates scattered light scattered by a portion of the circuit pattern and diffracted light diffracted by the same portion of the circuit pattern, separates the scattered light and the diffracted light according to the direction of illumination and wavelength, intercepts the diffracted light diffracted by straight portions of the circuit pattern with spatial filters disposed on the Fourier transform planes of the separated light, and focuses the light from the illuminated area on detectors; and a signal processing system that provides the defect data of foreign matters and the like on the circuit pattern by operating binary data obtained by binarizing the outputs of the detectors by a binarizing circuit set for a threshold, and signals representing the logical product of the binary data.

The present invention provides a method of detecting defects, such as foreign particles adhering to a substrate, comprising: projecting a front illuminating light beam obliquely on the front surface of a transparent or translucent substrate provided with a masking pattern and a pattern of a transparent or translucent film by a front illuminating system, concentrating scattered light scattered by the front surface of substrate and the pattern formed on the substrate, projecting a back illuminating light beam obliquely on the back surface of the substrate, concentrating transmitted-and-diffracted light transmitted and diffracted by the substrate and the pattern formed on the substrate, intercepting the scattered light scattered by the pattern and the transmitted-and-diffracted light transmitted and diffracted by the pattern with the spatial filters disposed on the Fourier transform planes to form images on detectors, and comparing the output of the detector representing the scattered light and that of the detector representing the transmitted-and-diffracted light to detect defects, such as foreign particles adhering to the substrate.

The present invention provides a method of detecting defects, such as foreign particles adhering to a substrate, comprising: projecting a front illuminating light beam obliquely on a transparent or translucent substrate provided with a pattern of an opaque film and a pattern of a transparent or translucent film by a front illuminating system, concentrating scattered light scattered by the surface of the substrate and the pattern formed on the substrate, projecting a back illuminating light beam obliquely on the back surface of the substrate by a back illuminating system, concentrating transmitted-and-diffracted light transmitted and diffracted by the substrate and the pattern formed on the substrate, separating the concentrated scattered light and the concentrated transmitted-and-diffracted light, intercepting the scattered light scattered by the pattern and the transmitted-and-diffracted light transmitted and diffracted by the pattern with spatial filters disposed on Fourier transform planes to focus images on a first detector and a second detector, respectively, and comparing the outputs of the first detector and the second detector to detect defects, such as foreign particles adhering to the substrate.

The method of detecting defects in accordance with the present invention is characterized in that the substrate is a component of a phase shift reticle. The method of detecting defects in accordance with the present invention is characterized in concentrating the scattered light and the transmitted-and-diffracted light by a focusing optical system disposed on the side of the front surface of the substrate with its optical axis substantially perpendicular to the surface of the substrate. The method of detecting defects in accordance with the present invention is characterized in illuminating an area in the front surface of the substrate with the front illuminating light beam along a plurality of directions and illuminating an area in the back surface of the substrate with the back illuminating light beam along a plurality of directions. The method of detecting defects in accordance with the present invention is characterized in using the front illuminating light beam and the back illuminating light beam alternately. The method of detecting defects in accordance with the present invention is characterized in that the front illuminating light beam and the back illuminating light beam are different in wavelength from each other, and the wavelength of the front illuminating light beam is longer than that of the back illuminating light beam. The method of detecting defects in accordance with the present invention is characterized in that the wavelength of the front illuminating light beam is in the range of 600 to 800 nm and the wavelength of the back illuminating light beam is in the range of 450 to 550 nm.

The present invention provides a projection exposure method comprising: a defect detecting step in which the front surface of the transparent or translucent substrate of a phase shift reticle, which is fabricated by forming a circuit pattern of an opaque thin film and a pattern of a transparent or translucent film on the substrate and attaching covering means formed by attaching transparent films to frames, respectively, to the opposite surfaces of the substrate to prevent the adhesion of foreign matters to the surfaces of the substrate, is illuminated through the transparent film of the covering means with a front illuminating light beam projected obliquely on the front surface of the substrate by a front illuminating system, scattered light scattered by the front surface of the substrate and by the pattern formed on the substrate is received through the transparent film of the covering means and concentrated, the back surface of the substrate is illuminated through the transparent film of the covering means with a back illuminating light beam projected obliquely on the back surface of the substrate through the transparent film of the covering means by a back illuminating system, transmitted-and-diffracted light transmitted and diffracted by the substrate and the pattern formed on the substrate is received through the transparent film of the covering means and concentrated, the concentrated scattered light and the concentrated transmitted-and-diffracted light are separated, the scattered light scattered by the pattern and the transmitted-and-diffracted light transmitted and diffracted by the pattern are intercepted with spatial filters disposed on Fourier transform planes, the light transmitted by the spatial filters is focused on a first detector and a second detector, and the outputs of the first detector and the second detector are compared to detect defects, such as foreign particles adhering to the substrate; a conveying step in which the phase shift reticle is conveyed, when it is confirmed in the defect detecting step that no defect is found on the substrate, to an exposure position in a projection exposure apparatus; and an exposure step in which a substrate to be processed is exposed to exposure light transmitted the phase shift reticle and focused by a focusing optical system and the phase of the light transmitted by the adjacent transparent or translucent film is shifted to prevent interference to form an image of the circuit pattern of the opaque film on the substrate.

The present invention provides a projection exposure method comprising: a first defect detecting step in which the front surface of the transparent or translucent substrate of a phase shift reticle, provided with a circuit pattern of an opaque film and a pattern of a transparent or translucent film is illuminated with a front illuminating light beam projected obliquely on the front surface of the substrate by a front illuminating system, scattered light scattered by the front surface of the substrate and the surfaces of the pattern formed on the substrate is concentrated, the back surface of the substrate is illuminated with a back illuminating light beam projected obliquely on the back surface of the substrate, transmitted-and-diffracted light transmitted and diffracted by the substrate and the pattern formed on the substrate is concentrated, the concentrated scattered light and the concentrated transmitted-and-diffracted light are separated, the scattered light scattered by the pattern and the transmitted-and-diffracted light transmitted and diffracted by the pattern are intercepted with spatial filters disposed on Fourier transform planes, the light transmitted by the spatial filters is focused on a first detector and a second detector, the outputs of the first detector and the second detector are compared to detect defects, such as foreign particles adhering to the substrate; a cover attaching step in which, when it is confirmed in the first defect detecting step that no defect is found in the phase shift reticle, covering means formed by attaching transparent films to frames, respectively, for preventing preventing the adhesion of foreign matters to the phase shift reticle are attached to the opposite surfaces of the phase shift reticle; a second second defect detecting step in which the front surface of the substrate is illuminated through the transparent film of the covering means with a front illuminating light beam projected obliquely on the front surface of the substrate by the front illuminating system, scattered light scattered by the front surface and the surfaces of the pattern formed on the substrate is concentrated, the back surface of the substrate is illuminated through the transparent film of the covering means with a back illuminating light beam projected obliquely on the back surface of the substrate by the back illuminating system, transmitted-and-diffracted light transmitted and diffracted by the substrate and the pattern formed on the substrate is received through the transparent film of the covering means and concentrated, the concentrated scattered light and the concentrated transmitted-and-diffracted light are separated, the scattered light scattered by the pattern and the transmitted-and-diffracted light transmitted and diffracted by the pattern are intercepted with spatial filters disposed on Fourier transform planes, the scattered light and the transmitted-and-diffracted light transmitted by the spatial filters are focused on the first detector and the second detector, respectively, and the outputs of the first detector and the second detector are compared to detect defects, such as foreign particles adhering to the substrate; a conveying step in which the phase shift reticle provided with the covering means is conveyed, when it is confirmed in the second defect detecting step that no defect is found on the substrate, to an exposure position in an projection exposure apparatus; and an exposure step in which a substrate to be processed is exposed to exposure light transmitted by the phase shift reticle and focused by a focusing system and the phase of the light transmitted by the adjacent transparent or translucent film is shifted to prevent interference to form an image of the circuit pattern of the opaque film on the substrate.

The present invention provides a defect detecting apparatus comprising: a front illuminating system that illuminates obliquely the front surface of a transparent of translucent substrate provided with a pattern of an opaque film and a pattern of a transparent or translucent film with a front illuminating light beam; a back illuminating system that illuminates obliquely the back surface of the substrate with a back illuminating light beam; a focusing optical system that concentrates and focuses scattered light, i.e., the front illuminating light beam emitted by the front illuminating system and scattered by the front surface of the substrate and the surface of the pattern and transmitted, and diffracted light, i.e., the back illuminating light beam emitted by the back illuminating system, and transmitted and diffracted by the substrate and the pattern formed on the substrate; spatial filters disposed on Fourier transform image planes to intercept the scattered light scattered by the pattern and the transmitted-and-diffracted light transmitted and diffracted by the pattern; detectors that receive the concentrated scattered light the concentrated transmitted-and-diffracted light transmitted by the spatial filters and provide output signals corresponding to the receive light; and detecting means that compares the output signal of the detector representing the scattered light and the output signal of the detector representing the transmitted-and-diffracted light to detect defects, such as foreign particles adhering to the substrate.

The present invention provides a defect detecting apparatus comprising: a front illuminating system that illuminates obliquely the front surface of a transparent or translucent substrate provided with a pattern of an opaque film and a pattern of a transparent or translucent film with a front illuminating light beam; a back illuminating system that illuminates obliquely the back surface of the substrate with a back illuminating light beam; a focusing optical system that concentrates and focuses scattered light, i.e., the front illuminating light beam emitted by the front illuminating system and scattered by the surface of the substrate and the surface of the pattern formed on the substrate, and transmitted-and-diffracted light, i.e., the back illuminating light beam emitted by the back illuminating system and transmitted and diffracted by the substrate and the pattern formed on the substrate; a separating optical system that separates the scattered light and the transmitted-and-diffracted light; a first spatial filter and a second spatial filter disposed on Fourier transform planes to intercept the scattered light scattered by the pattern and the transmitted-and-diffracted light transmitted and diffracted by the pattern; a first detector and a second detector that receives the scattered light and the transmitted-and-diffracted light focused by the focusing optical system, respectively, and provides output signals; and detecting means that compares the output signal of the first detector representing the scattered light and the output signal of the second detector representing the transmitted-and-diffracted light to detect defects, such as foreign particles adhering to the substrate.

The present invention provides a projection exposure apparatus comprising: a defect detecting means that illuminates obliquely the front surface of the transparent or translucent substrate of a phase shift reticle fabricated by forming a circuit pattern of an opaque film and a pattern of a transparent or translucent film on the front surface of the substrate and provided on the front and the back surfaces of the substrate with covering means formed by attaching transparent films respectively to frames with a front illuminating light beam emitted by a front illuminating optical system through the transparent film of the covering means, concentrates scattered light scattered by the front surface of the substrate and the surface of the pattern, illuminates obliquely the back surface of the substrate with a back illuminating light beam emitted by a back illuminating system through the transparent film of the covering means, concentrates transmitted-and-diffracted light transmitted and diffracted by the substrate and the pattern and traveling through the transparent film of the covering means, separates the concentrated scattered light and the concentrated transmitted-and-diffracted light, intercepting the scattered light scattered by the pattern and the transmitted-and-diffracted light transmitted and diffracted by the pattern with spatial filters disposed on Fourier transform planes, focuses the scattered light and the transmitted-and-diffracted light respectively on a first detector and a second detector, and compares the outputs of the first detector and the second detector to detect defects, such as foreign particles adhering to the substrate; conveying means that conveys the phase shift reticle provided with the covering means, when it is confirmed by the defect detecting means that no defect is found on the substrate, to an exposure position; and a projection exposure means that exposes a substrate to be processed to exposure light transmitted by the phase shift reticle and focused by a focusing optical system and shifts the phase of the light transmitted by the adjacent transparent or translucent film to prevent interference to form an image of the circuit pattern of the opaque film on the substrate.

The present invention provides a projection exposure apparatus comprising: a defect detecting means that illuminates obliquely the front surface of the transparent or translucent substrate of a phase shift reticle fabricated by forming a circuit pattern of an opaque film and a pattern of a transparent or translucent film on the front surface of the substrate with a front illuminating light beam emitted by a front illuminating system, concentrating scattered light scattered by the front surface of the substrate and the surface of the pattern, illuminates obliquely the back surface of the substrate by a back illuminating system, concentrates transmitted-and-diffracted light transmitted and diffracted by the substrate and the pattern, separates the scattered light and the transmitted-and-diffracted light, intercepts the scattered light scattered by the pattern and the transmitted-and-diffracted light transmitted and diffracted by the pattern with spatial filters disposed on Fourier transform planes, focuses the scattered light and the transmitted-and-diffracted light transmitted by the spatial filters on a first detector and a second detector, and compares the outputs of the first detector and the second detector to detect defects, such as foreign particles adhering to the substrate; a conveying means that conveys the phase shift reticle, when it is confirmed by the defect detecting means that no defect is found on the substrate, to an exposure position; and a projection exposure means that illuminates a substrate to be processed with exposure light transmitted by the phase shift reticle located at the exposure position and focused by a focusing optical system and shifts the phase of the light transmitted by the adjacent transparent or translucent film to prevent interference to form an image of the circuit pattern of the opaque film on the substrate.

The present invention provides a projection exposure apparatus comprising: a defect detecting means that illuminates obliquely the front surface of the transparent or translucent substrate of a phase shift reticle fabricated by forming a circuit pattern of an opaque film and a pattern of a transparent or translucent film on the front surface of the substrate with a front illuminating light beam by a front illuminating system, concentrates scattered light scattered by the front surface of the substrate and the surface of the pattern formed on the substrate, illuminates obliquely the back surface of the substrate with a back illuminating light beam by a back illuminating system, concentrates transmitted-and-diffracted light transmitted and diffracted by the substrate and the pattern formed on the substrate, separates the scattered light and the transmitted-and-diffracted light, intercepts the scattered light scattered by the pattern and the transmitted-and-diffracted light transmitted and diffracted by the pattern with spatial filters disposed on Fourier transform planes, focuses the scattered light and the transmitted-and-diffracted light transmitted by the spatial filters on a first detector and a second detector, respectively, and compares the outputs of the first detector and the second detector to detect defects, such as foreign particles adhering to the substrate; a conveying means that conveys the phase shift reticle, when it is confirmed by the defect detecting means that no defect is found on the substrate, to an exposure position; and a projection exposure means that exposes a substrate to be processed to exposure light transmitted by the phase shift reticle located at the exposure position and focused by a focusing optical system and shifts the phase of the light transmitted by the adjacent transparent or translucent film to prevent interference to form an image of the circuit pattern of the opaque film on the substrate.

The present invention provides a projection exposure apparatus comprising: a defect detecting means that illuminates obliquely the front surface of a transparent or translucent substrate of a phase shift reticle fabricated by forming a circuit pattern of an opaque film and a pattern of a transparent or translucent film with a front illuminating light beam emitted by a front illuminating system before and after attaching a covering means to the phase shift reticle, concentrates scattered light scattered by the front surface of the substrate and the surface of the pattern formed on the substrate, illuminates obliquely the back surface of the substrate with a back illuminating light beam emitted by a back illuminating system, concentrates transmitted-and-diffracted light transmitted and diffracted by the substrate and the pattern formed on the substrate, separates the concentrated scattered light and the concentrated transmitted-and-diffracted light, intercepts the scattered light scattered by the pattern and the transmitted-and-diffracted light transmitted and diffracted by the pattern with spatial filters disposed on Fourier transform planes, focuses the scattered light and the transmitted-and-diffracted light transmitted by the spatial filters on a first detector and a second detector, compares the outputs of the first detector and the second detector to detect defects, such as foreign particles adhering to the substrate; a conveying means that conveys the phase shift reticle provided with the covering means, when it is confirmed that no defect is found on the substrate by the defect detecting means, to an exposure position; and a projection exposure means that illuminates a substrate to be processed with exposure light transmitted by the phase shift reticle and focused by a focusing optical system and shifts the phase of the light transmitted by the adjacent transparent or translucent film to prevent interference to form and image of the circuit pattern of the opaque film on the substrate.

Incidentally, in an exposure process employing a reticle or the like for fabricating LSI circuits or printed wiring boards, a circuit pattern formed on the reticle or the like is inspected before printing the circuit pattern on wafers. If the circuit pattern has minute foreign particles having sizes, for example, even on the micron order thereon, the circuit pattern cannot correctly be printed on wafers and, consequently, all the LSI circuits fabricated by using such wafers become defective. Problems attributable to the minute foreign particles adhering to the reticle have become more and more significant with the recent progressive increase in the degree of integration of LSI circuits and the existence of even foreign particles having sizes on the submicron order on the reticle is not permissible.

Increase in frequency of missing finding foreign particles and the like that affect adversely to the fabrication of LSI circuits, which is liable to increase as the size of foreign particles to be found decreases, must be avoided. Recently, a reticle provided with a circuit pattern, and a pattern of a phase shift film or a transparent or translucent film called a phase shifter filling up spaces in the circuit pattern and having a thickness substantially equal to an odd multiple of half the wavelength of exposure light has been developed print a circuit pattern of a metal thin film, such as a chromium thin film, formed on the reticle in an improved resolution. The thickness of this transparent or translucent phase shift pattern is several times that of the circuit pattern on the order of 0.1 μm. Therefore, the intensity of diffracted light diffracted by the edges of the phase shift pattern is several to tens times that of diffracted light diffracted by the edges of the circuit pattern, and such a high intensity of diffracted light reduces the sensitivity of detection of foreign particles remarkably.

(1) Detection of Front/Back Surface Logical Product, Processing Circuit and Switching of Illumination As stated above, it is difficult to discriminate, by the conventional techniques, between the circuit pattern of reticles including the phase shift reticle for fabricating DRAMs of, for example, 64M or above and foreign particles adhering to the reticles and to detect only the foreign particles.

The present invention solves the foregoing problems on the basis of an experimental fact discovered by the inventors of the present invention that the intensity of scattered light scattered by the circuit pattern of a reticle is dependent on the incidence angle of the illuminating light beam, which will be described with reference to FIG. 10.

In FIG. 10, points 701 and 702 indicate detection signals corresponding to the intensity of scattered light scattered by a defect 70, such as a minute foreign particle, of 0.5 μm or below in size, points 864, 874, 865, 875, 866, 876, 867 and 877 indicate detection signals corresponding to the intensities of scattered light scattered by all the corners 82 of 0-degree, 45-degree and 90-degree edges of a circuit pattern, and points 701, 861, 862, 863, 864, 865, 866 and 867 indicate detection signals corresponding to the intensities of scattered light scattered by a minute circuit pattern of a size 84 on the order of 0.5 μm. The points 701, 861, 862, 863, 864, 865, 866 and 867 indicate the detection signals provided when the illuminating light beam projected by a first illuminating system 2 (or 3) of FIG. 1 and scattered by the circuit pattern is detected. The points 702, 871, 872, 873, 874, 875, 876 and 877 indicate the detection signals provided when the illuminating light beam projected by a second illuminating system 20 (or 30) of FIG. 1 and scattered by the circuit pattern is detected. For example, detection signals 861←—→871 are those provided when the illuminating light beam projected by the first illuminating system 2 (or 3) of FIG. 1 and scattered by a portion of the minute circuit pattern is detected and when the illuminating light beam projected by the second illuminating system 20 (or 30) of FIG. 1 and scattered by the same portion of the minute circuit pattern is detected, respectively. As is obvious from FIG. 10, the value of the detection signal provided upon the detection of the defect 70, such as a foreign particle, is less dependent on the direction of projection of the illuminating light beam than the value of the detection signal provided upon the detection of the circuit pattern. In FIG. 10, a dotted line indicate a threshold for detection signals.

As is obvious from FIG. 10, the value of the detection signal provided when a portion of a minute circuit pattern is detect is greatly dependent on the direction of projection of the illuminating light beam and, when a portion of the surface of a reticle 6 is illuminated obliquely with two illuminating light beams traveling respectively in opposite directions, either of the detection signals provided upon the detection of the two illuminating light beams scattered by the illuminated portion is always smaller than the detection signal provided upon the detection of the scattered light scattered by the foreign particle of a size on the submicron order as indicated by solid circles.

Therefore, when a portion of the surface of the reticle 6 is illuminated with both the illuminating light beams traveling respectively in opposite directions as shown in FIG. 1, the detection signal indicating a particle or a circuit pattern is merely the sum of a detection signal provided upon the detection of one of the illuminating light beams scattered by the particle or the circuit pattern and a detection signal provided upon the detection of the other illuminating light beam scattered by the same, and it is difficult to binarize the detection signal by using a threshold. However, when one of the scattered illuminating light beams and the other scattered illuminating light beam are detected respectively by two detectors, and the detection signals provided by the two detectors are binarized by using the threshold 91 respectively by two binarizing circuits, both the detection signals for the foreign particle or the like are "1", and either of the detection signals for the circuit pattern is "1" or both the detection signals for the circuit pattern are "0". Accordingly, the defect 70, such as a foreign particle of a size on the submicron order can be discriminated from the circuit pattern on the basis of the logical product of the binary outputs of the binarizing circuits.

(2) Back Illuminating System, Coherence Length, Balance of Amount of Light, Correction of Optical Path Length, Correction of Illuminated Position As stated above, it is difficult for the conventional techniques to discriminate between the circuit pattern of a reticle, such as a phase shift reticle, to be used for fabricating, for example, a DRAM of 64M or greater and foreign particles adhering to the reticle, and to detect only the foreign particles.

The present invention relates to a foreign particle detecting method of a back illumination system capable of detecting foreign particles adhering to a phase shift reticle without being affected by the phase shifter of the phase shift reticle. When inspecting a photomask, such as a reticle, having a glass substrate foreign particles, this foreign particle detecting method inserts a glass plate having a thickness corresponding to the difference between a standard thickness and the thickness of the glass substrate between the back surface of the reticle and the optical system to adjust the optical path length between the optical system and the front surface of the reticle on which a circuit pattern is formed to a fixed length regardless of the thickness of the reticle to avoid the variation of concentration of the illuminating light beam and the illuminated position according to the thickness of the glass substrate.

(3) Spatial Filter for Observation and Oblique Projection of Laser beam

In some cases, it is difficult to observe foreign particles by an observation optical system using ordinary drop illumination or transmission illumination when the foreign particles have a very small size on the order of, for example, 0.3 μm. Furthermore, such an object cannot be illuminated in a brightness enough for observation by ordinary dark field illumination.

Practically, it is effective to illuminate such an object obliquely with a laser beam and to observe scattered light.

Although it is desirable to use a laser beam for detection for observation, an additional TV camera or the like sensitive to the wavelength of the laser beam will be necessary for observation if the laser beam is not visible radiation. Therefore, a laser illuminating system that emits a laser beam having a wavelength in the wavelength range of visible radiation is used specially for observation. The use of a laser illuminating system employing a laser diode having an oscillation wavelength in the wavelength range of visible radiation will enable the system to be formed in a small, simple construction.

An observation system employing oblique illumination with a laser beam, similarly to a detecting system, is able to eliminate scattered light scattered by a circuit pattern by a spatial filter. Therefore, an observation system capable of incorporating a spatial filter when necessary is able to stress scattered light scattered by defects, such as foreign particles, which facilitate the identification of the defects.

(4) Measurement of the Transmittance of a Pellicle

A pellicle for protecting a circuit pattern formed on a reticle has characteristics, including an antireflection characteristic, to suppress the reduction of the intensity of transmitted exposure light (in most cases, near-ultraviolet light or ultraviolet light). Since the characteristics of the reticle is optimized for use in connection with exposure light, the characteristics are not necessarily optimum for use in connection with illuminating light for inspection and the reticle reduces the intensity of the illuminating light for inspection. Since different pellicles have different illuminating light reducing ratios, the use of a pellicle narrows the allowance of criterion for inspection.

If a light beam travels perpendicularly through a pellicle (scattered light scattered by a sample in this embodiment travels in such a way), the difference in illuminating light reducing ratio between different pellicles is negligibly small. However, a light beam that travels obliquely through a pellicle (an illuminating light projected obliquely on a sample in this embodiment travels in such a way), the transmittance of the pellicle is an important factor. A method of measuring the transmittance of a pellicle which affects the transmission of a light beam that travels obliquely through the pellicle will be described hereinafter.

A detection output correcting method proposed in Japanese Patent Laid-open (Kokai) No. 4-151663 measures the transmittance of a pellicle incorporated into a reticle for the inspection of every and corrects the detection output. This known detection output correcting method projects a laser beam perpendicularly to the pellicle, measures the intensity of regularly reflected light from a chromium film formed over the surface of the substrate of the reticle, and calculates the ratio of the intensity of the regularly reflected light to that of the light before falling on the pellicle to determine the transmittance of the pellicle. Since the measurement is affected by both the reflectivity of the pellicle and that of the substrate of the reticle, the reflectivity of the substrate affects measuring accuracy. When the illuminating light beam for detection is projected obliquely on the reticle as the illuminating light beam is projected in the present invention, the laser beam for measurement must be projected obliquely so as to fall on the surface of the substrate at an incidence angle equal to that at which the illuminating light for detection falls on the surface of the substrate, which is different from the known detection output correcting method.

The present invention projects obliquely a light beam having a wavelength equal to that of the illuminating light beam for detection on the pellicle at an incidence angle equal to that at which the illuminating light beam for detection falls on the pellicle, measures the intensity of reflected light from the pellicle, and determines the reflectivity of the pellicle on the basis of the measured intensity of the reflected light from the pellicle and the intensity of the light emitted by the light source. Supposing that the internal absorbance of the pellicle is negligible, (Intensity of transmitted light)=(Intensity of incident light)−(Intensity of reflected light)

(Transmittance)=(Intensity of transmitted light)/(Intensity of incident light)

Therefore, (Transmittance)= {(Intensity of incident light)−(Intensity of reflected light)}/(Intensity of incident light)

The detection output is corrected by using the calculated transmittance.

(5) Switching of Spatial Filter, Polarizing Plate: Detection of Four-Pixel Maximum Value and Detection of Logical Sum The present invention has been made on the basis of a fact that diffracted/scattered light (hereinafter, "diffracted light"), which is part of an illuminating light projected obliquely on a photomask, such as a reticle, and diffracted by the circuit pattern of the photomask, such as a reticle, is concentrated in a specific area on the Fourier transform plane of a plane including the circuit pattern, particularly, in the linear central area as shown by photographs on the left-hand side of FIGS. 73(A) to 73(C). White portions in these photographs of FIGS. 73(A) to 73(C) are different kinds of diffracted light, i.e., part of an illuminating light beam projected obliquely on and diffracted by different circuit patterns, as observed on the Fourier transform planes of the circuit patterns. Although some kinds of diffracted light form different diffraction patterns, most kinds of diffracted light are concentrated in the central areas of the Fourier transform planes in linear patterns as shown in FIGS. 73(A) to 73(C). Therefore, the scattered light scattered by a foreign particle and traveling through the light-transmissive area of the spatial filter can be detected by intercepting most part of the diffracted light diffracted by the circuit pattern with a spatial filter having a shading portion having an appropriate width selected from among spatial filters having shading portions of different widths, respectively, capable of shading the central areas of the corresponding Fourier transform planes as shown on the right-hand side of FIGS. 73(A) to 73(C), because the scattered light scattered by a foreign particle cannot be concentrated in the central area of the Fourier transform plane.

In a very rare case, a type of a photomask, such as a reticle, does not diffract light so that the diffracted light will not be concentrated in the central area of the Fourier transform plane as shown in FIG. 73(D). For such a reticle, a polarizing filter may be disposed on the Fourier transform plane.

When an operation for the detection and determination of defects, such as foreign particles, is executed by an array type detector, such as a CCD, for each pixel, and a defect, such as a foreign particle, extends over a plurality of pixels, for example, two to four pixels, scattered light from the defect is distributed to a plurality of pixels and the magnitude of the detection signal of each pixel is ½ to ¼ of that of the same when all the scattered light falls thereon, so that the repeatability of inspection is deteriorated. To solve such a problem, a four-pixel addition method proposed in Japanese Patent Laid-open (Kokai) No. 5-2262 reduces each side of the pixel by half (by a factor of four in area), and adds the detection signals of the adjacent four pixels electrically to simulate the detection signal of a desired pixel.

If the size of a foreign particle, for example, 0.5 μm, is small as compared with the size of a detection pixel, for example, 2 μm×2 μm, the detection signal representing the intensity of scattered light from the defect, provided before the four-pixel addition operation and the detection signal obtained through the four-pixel addition operation are equal to each other, because the four-pixel addition operation provides the sum of the detection signals of a plurality of pixels corresponding to the defect. In this case, since the smaller the area (size) of each pixel of the detector, the smaller is the number (or the area) of corners of the circuit pattern corresponding to one pixel, the scattered light from the circuit pattern decreases. Therefore, smaller pixels are more preferable and enables the detection of defects in a higher detection sensitivity. Accordingly, the four-pixel addition method reduces and sacrifices the detection sensitivity for the stabilization of detection. Although any measures need not be taken if the reduced detection sensitivity is high enough, some measures must be taken to make the detection sensitivity effective even if process conditions and exposure method are changed.

This problem may be solved by selectively using either a high-stability detection mode including the four-pixel addition operation or a high-sensitivity detection mode not including the four-pixel addition operation according to required performance.

The present invention provides means capable of achieving both the purposes of the high-stability detection mode and the high-sensitivity detection mode by carrying out the detection of foreign particles before and after the four-pixel addition operation and providing the logical sum of the results of detection in the high-stability detection mode and in the high-sensitivity detection mode on the basis of a fact that both the high-stability detection mode and the high-sensitivity detection mode can be carried out if defects, such as foreign particles, are detected before and after the four-pixel addition operation.

When the two modes are used synchronously, the amount of data to be processed before the four-pixel addition operation is four times that of data to be processed after the four-pixel addition operation, because one piece of data is obtained from four pixels after the four-pixel addition operation. However, if only the maximum detection data among those provided by the four adjacent pixels before the four-pixel addition operation is used, the amount of data is reduced to ¼ and the amount of data to be processed before the four-pixel addition operation and that of data to be processed after the four-pixel addition operation are equal to each other, which facilitates the operation for obtaining the logical sum.

(6) Two-Pixel Addition Method

When an operation for the detection and determination of defects, such as foreign particles, is executed by an array type detector, such as a CCD, for each pixel, and a defect, such as a foreign particle, extends over a plurality of pixels, for example, two to four pixels, scattered light from the defect is distributed to a plurality of pixels and the magnitude of the detection signal of each pixel is ½ to ¼ of that of the same when all the scattered light falls thereon, so that the repeatability of inspection is deteriorated. To solve such a problem, the four-pixel addition method proposed in Japanese Patent Laid-open (Kokai) No. 5-2262 reduces each side of the pixel by half (by a factor of four in area), and adds the detection signals of the adjacent four pixels electrically to simulate the detection signal of a desired pixel.

Since this known method is intended to prevent the reduction of the detection signal indicating the defect extending over a plurality of pixels, the number of pixels of each pixel group may be more than four, two or three provided that the desired object can be achieved.

The present invention uses a rectangular pixel that can be realized by feeding the stage at a high feed speed as compared with data storing time required by the detector for storing data. For example, if the detector has pixels each corresponding to an area of 1 μm×1 μm on a sample, and the stage is moved 2 μm in a data storing time T, each pixel corresponds to an area of 1 μm×2 μm on the sample.

In this case, the addition of the output signals of two pixels corresponds to the output signal of a desired pixel. Although the effect of the two-pixel addition method on preventing the reduction of the detection signal indicating the defect extending over four pixels is lower than that of the four-pixel addition method, the two-pixel addition method improves the inspection speed because the stage feed speed of the two-pixel addition method is higher than that of the four-pixel addition method.

(7) Pellicle/Glass Surface Detecting System

Since the present invention uses a high-resolution detector, it is difficult for the present invention to carryout high-speed defect detection, and the present invention is disadvantageous in respect of inspection time as compared with the conventional method. When a photomask, such as a reticle, is inspected for defects, the back surface of the photomask opposite the front surface of the same on which a circuit pattern is formed, i.e., the surface of a glass plate not provided with any circuit pattern, and the surface of the pellicle must be inspected in addition to the inspection of the circuit pattern, which must be inspected in a high detection sensitivity. Since those surfaces may be inspected in a detection sensitivity far lower than that necessary for inspecting the circuit pattern, the application of a high-resolution high-sensitivity inspecting method to the inspection of those surfaces wastes time uselessly.

An inspecting method proposed in Japanese Patent Laid-open (Kokai) No. 4-273008 employs, instead of increasing the speed, a detection illuminating system for illuminating the sample for the inspection of the surface provided with a circuit pattern, capable of illumination for a large depth of focus, instead of low light concentration, to utilize the time to spare permitted by the low-sensitivity detection.

When a focusing optical system having a large numerical aperture is used, it is usual to change resolution by changing the magnification of the objective. Since the front surface of the substrate provided with a circuit pattern, the back surface of the substrate, and the pellicle extend respectively in different planes, the focus (detection point) must be moved in a range of several millimeters and hence the Z-stage, i.e., a stage that moves along the width of the photomask, such as a reticle, must be moved accurately for the high-accuracy high-resolution inspection of the circuit pattern.

The present invention employs a detecting unit for inspecting the back surface of the reticle and the pellicle at a high detecting speed in a low resolution in addition to a detecting unit for inspecting the front surface of the reticle on which a circuit pattern is formed.

(8) Shading Correcting Method: Detection Wavelength Determining Method: Detection Sensitivity Determining Method

BRIEF DESCRIPTION OF THE DRAWINGS

The above and other objects, features and advantages of the present invention will become more apparent from the following description taken in connection with the accompanying drawings, in which:

FIGS. 4(A), 4(B), 4(C) and 4(D) are views of assistance in explaining a reticle inspecting method in accordance with the present invention;

FIGS. 12(A) and 12(B) are views of assistance in explaining a method of detecting scattered light from a foreign particle by using an optical system having a high NA in accordance with the present invention;

FIG. 20 is a graph showing the respective variations of detection signals provided when a 0.5 μm particle on the chromium pattern is detected and when the chromium pattern is detected, respectively, in the front illumination mode with the wavelength of the illuminating light beam;

FIG. 21 is a graph showing the respective variations of detection signals provided when a 1.0 μm particle on the chromium pattern is detected and when the phase shifter pattern is detected, respectively, in the front illumination mode with the wavelength of the illuminating light beam;

FIG. 22 is a graph showing the respective variations of detection signals provided when a 0.5 μm particle on a glass substrate is detected and when the chromium pattern is detected, respectively, in the back illumination mode with the wavelength of the illuminating light beam;

FIGS. 38(A)–38(C) are sectional views of assistance in explaining the change of illuminating units in accordance with the present invention;

FIGS. 39(A) and 39(B) are sectional views of assistance in explaining the change of illuminating units in accordance with the present invention;

FIGS. 65(A) and 65(B) are block diagrams of a mask fabricating process and a stepper process in accordance with the present invention;

DETAILED DESCRIPTION OF THE PREFERRED EMBODIMENTS

Figure 36:
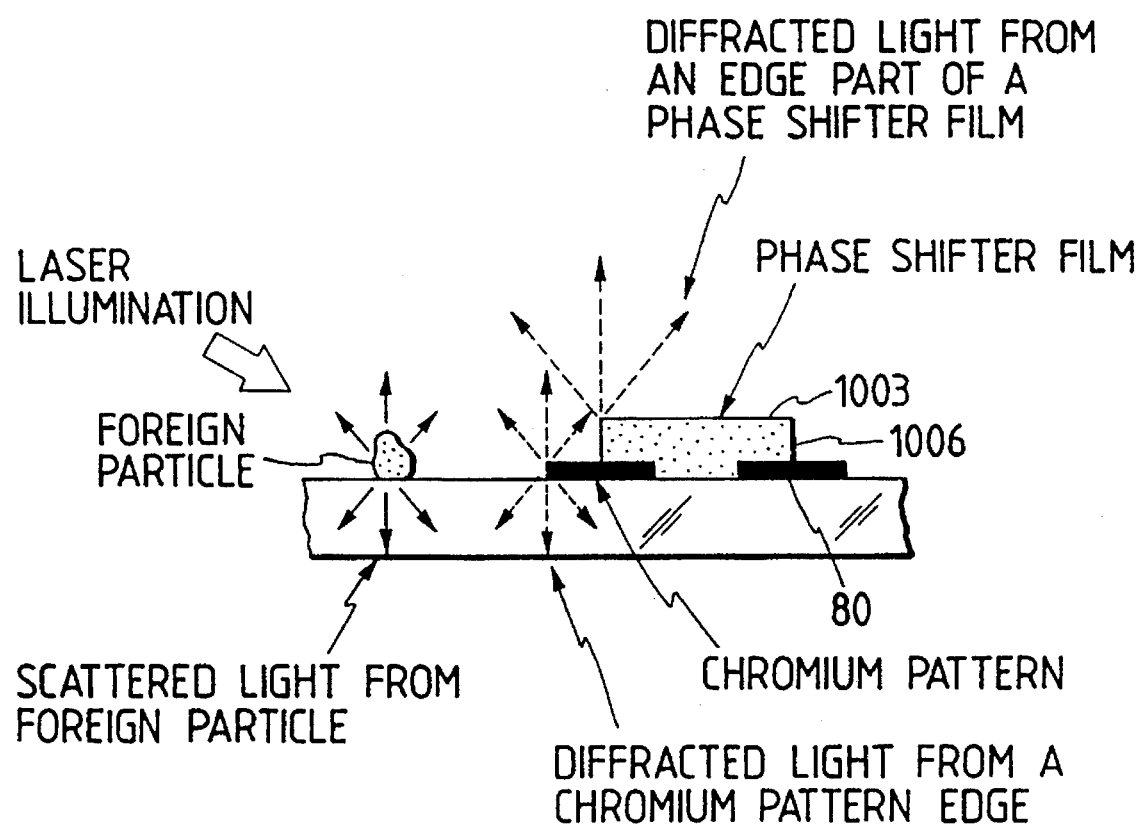
FIG. 36 is a diagrammatic view of assistance in explaining scattered light and diffracted light scattered and diffracted, respectively, by a reticle provided with a phase shifter film.

A reticle as shown in FIG. 36 has been recently developed to improve resolution in transferring a circuit pattern of a metal thin film, such as a chromium thin film (hereinafter referred to as "chromium pattern"). This recently developed reticle will be referred to as "phase shift reticle" hereinafter. The phase shift reticle is provided with a pattern of a transparent or translucent thin film (hereinafter referred to as "phase shift pattern"), which is called a phase shift film or a phase shifter, having a thickness equal to odd times the half of the wavelength of light emitted by an exposure light source. The film forming the phase shift pattern is transparent or translucent and has a thickness several times the thickness on the order of 0.1 µm of the chromium pattern.

Figure 16:
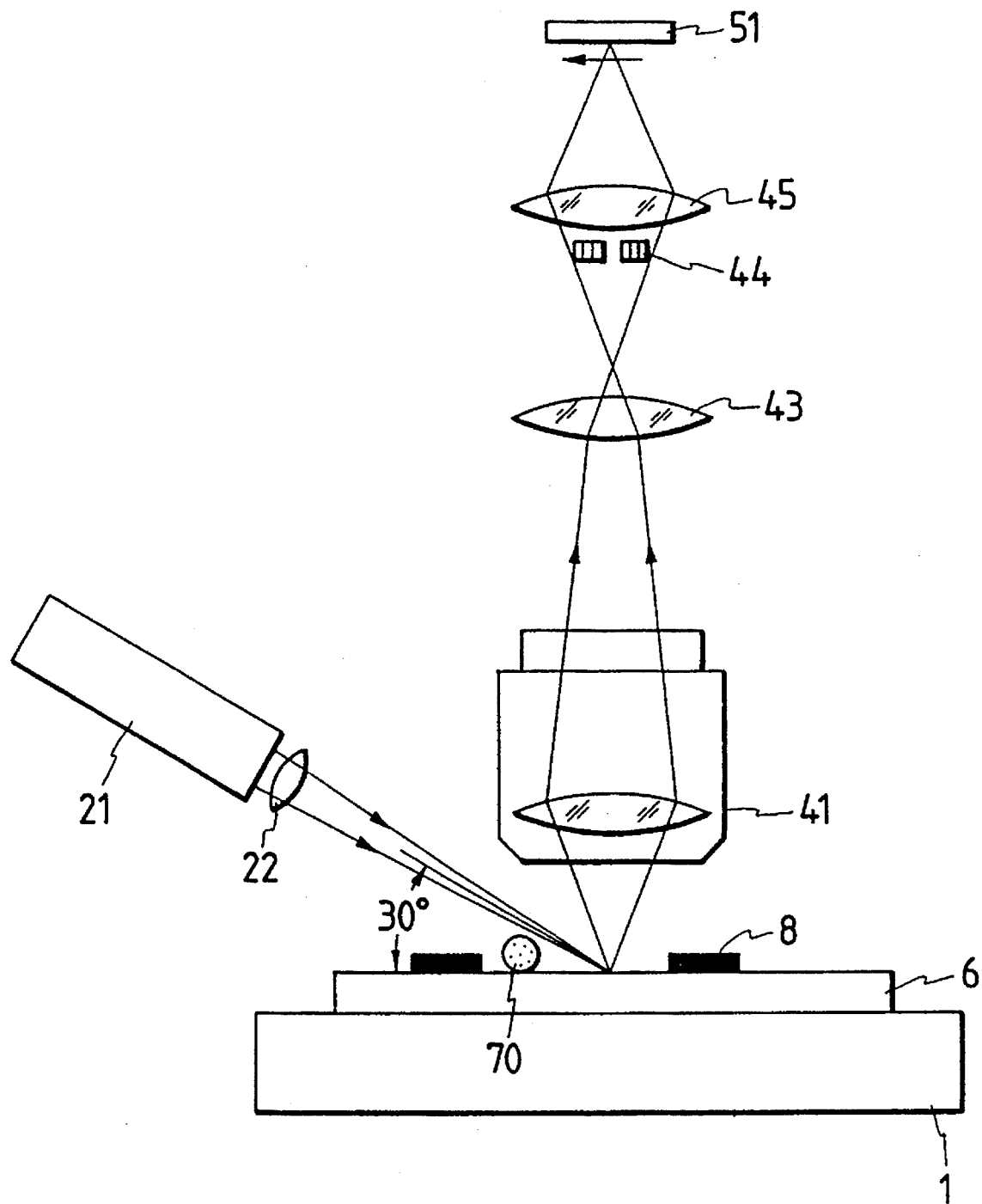
FIG. 16 is a diagrammatic view showing the configuration of a prior art reticle inspecting apparatus.

When inspecting a reticle by the conventional reticle inspecting apparatus, the front surface of the reticle on which the chromium pattern is formed is illuminated and scattered light is gathered by a detection optical system disposed on the side of the front surface (FIG. 16, front illumination mode). When the phase shift reticle is inspected for foreign particles in this front illumination mode, there arises a problem that scattered light scattered by edges of the phase shifter pattern, which is several times to several tens times greater than diffracted light diffracted by edges of the chromium pattern, reduces the foreign particle detection sensitivity greatly.

This invention utilizes a fact that the edges of the phase shifter pattern extend on the chromium pattern of an opaque film to solve the problem. When the illuminating light is projected from the side of the back surface of the reticle and the scattered light is gathered by the detection optical system disposed on the side of the front surface of the reticle (FIG. 17, back illumination mode), the illuminating light traveling toward the edges of the phase shift pattern is intercepted by the chromium pattern of an opaque film of the phase shift reticle and, consequently, the foreign particle detection sensitivity is not reduced because the illuminating light is not scattered by the phase shift pattern.

The back illumination mode is able to detect only foreign particles in the light-transmissive portions, i.e., portions in which any elements of the chromium pattern are not formed. Practically, foreign particles on the chromium pattern needs to be detected. Accordingly, it is desirable to illuminate the reticle in both the front illumination mode and the back illumination mode in combination. The front illumination mode and the back illumination mode will be described hereinafter in terms of foreign particles and the intensity of the scattered light scattered by the front surface of the reticle.

Figure 18:
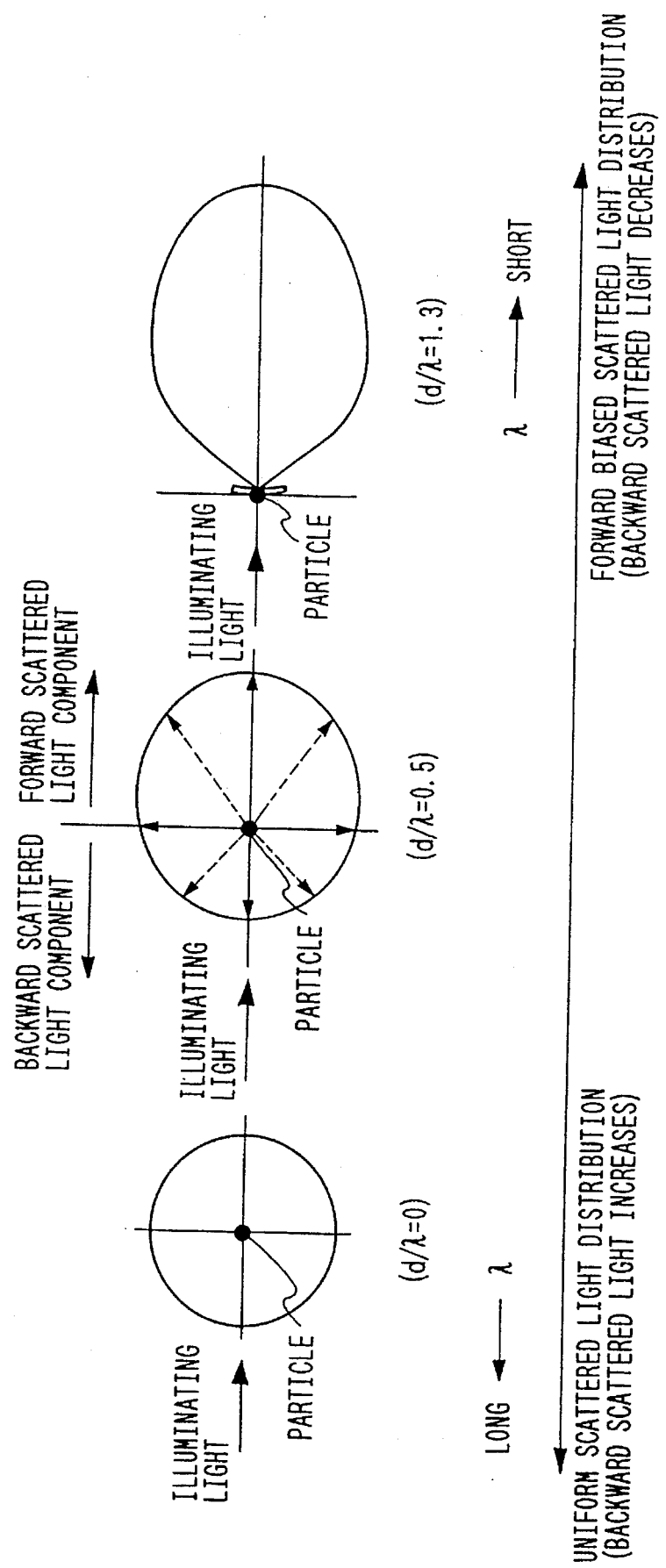
FIG. 18 is a diagrammatic view showing the relation between the distribution of components of scattered light scattered by a particle and $d/\lambda$, where d is the size of the particle and $\lambda$ is the wavelength of the illuminating light beam.

According to the light scattering theory, scattered light scattered by particles is in similar correspondence in respect of the relation between wavelength and particle size. FIG. 18 shows the relation between the distribution of scattered light scattered by a particle and $d/\lambda$ (d: size of the particle, $\lambda$: wavelength of the light emitted by a light source). The light component scattered in the direction of travel of the illuminating light is called a forward scattered light component, and the light component scattered in the direction opposite the direction of travel of the illuminating light is called a backward scattered light component.

When the illuminating light falls on a particle having a certain size, the shorter the wavelength of the illuminating light, the greater is the forward scattered light component, and the longer the wavelength of the illuminating light, the higher is the uniformity of distribution of the scattered light components and the greater is the ratio of the backward scattered light component to all the scattered light components.

Figure 19B:
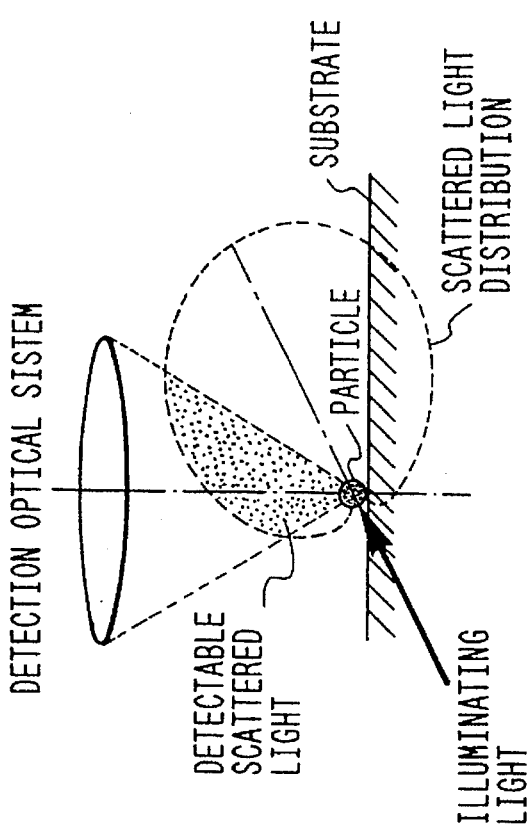
FIGS. 19(A) and 19(B) are diagrammatic views of assistance in explaining the configuration of a reticle inspecting apparatus in accordance with the present invention and scattered light components which can be detected by the same reticle inspecting apparatus.
Figure 19A:
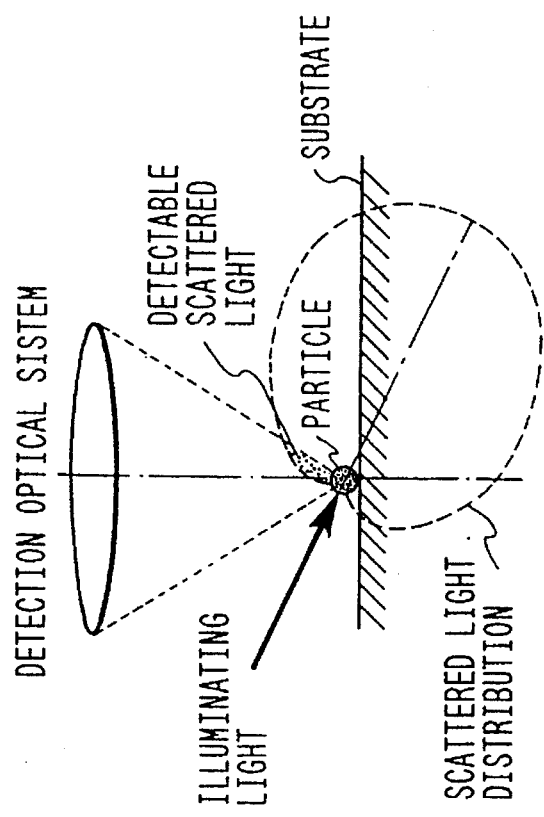

FIG. 19(A) shows the positional relation between the direction of travel of the illuminating light and the detection optical system for the front illumination mode, and FIG. 19(B) shows the positional relation between the direction of travel of the illuminating light and the detection optical system for the back illumination mode. The front illumination mode detects the backward scattered light component, and the back illumination mode detects the forward scattered light component. As shown in FIG. 18, the forward scattered light component is always greater than the backward scattered light component. Therefore, it is effective to detect the forward scattered light component to obtain a high foreign particle detection signal. Thus, it is advantageous to detect the forward scattered light component in the back illumination mode to detect foreign particles in the light-transmissive portions of the reticle whether the reticle is provided with the phase shifter pattern or not.

A reticle inspecting apparatus for inspecting a reticle, such as a photomask, fabricated by forming a circuit pattern of an opaque film on a transparent (or translucent) substrate for foreign particles adhering to the substrate is able to provide high foreign particle detection signals by detecting foreign particles in the opaque portions in the front illumination mode and detecting foreign particles in the light-transmissive portions in the back illumination mode.

In either illumination mode, a maximum foreign particle detection signal can be obtained by using illuminating light having an optimum wavelength. Experiments were conducted to determine illuminating light having an optimum wavelength to obtain a maximum foreign particle detection signal through the examination of the dependence of detecting ability on the wavelength of illuminating light.

In the front illumination mode, the backward scattered light component and hence the foreign particle detection signal increase with the increase of the wavelength of the illuminating light.

FIG. 20 shows the variation of chromium pattern detection signal provided when the chromium pattern is detected and the variation of the particle detection signal provided when a 0.5 µm particle on the chromium pattern (opaque portion) is detected in the front illumination mode with the wavelength of the illuminating light. Laser beams of 830 nm, 780 nm, 633 nm, 532 nm, 515 nm and 488 nm, respectively, in wavelength were used as illuminating light beams. In the wavelength range of 488 nm to 830 nm, the longer the wavelength, the higher is the particle detection signal, and the particle detection signal reaches a peak when the wavelength is 780 nm. The chromium pattern detection signal varies with the wavelength in a comparatively narrow range.

FIG. 21 shows the variation of a shifter pattern detection signal provided when the shifter pattern is detected and the variation of the particle detection signal provided when a 1.0 µm particle on the chromium pattern (opaque portion) is detected in the front illumination mode with the wavelength of the illuminating light. Laser beams of 830 nm, 780 nm, 633 nm, 532 nm, 515 nm and 488 nm, respectively, in wavelength were used as illuminating light beams. In the wavelength range of 488 nm to 830 nm, the longer the wave-length, the higher are both the particle detection signal and the shifter pattern detection signal.

In the back illumination mode, the shorter the wavelength of the illuminating light, the greater is the forward scattered light component and higher is the particle detection signal.

FIG. 22 shows the variation of the particle detection signal provided when a 0.5 µm particle on the glass plate (light-transmissive portion) is detected and the variation of chromium pattern detection signal provided when the chromium pattern is detected in the back illumination mode with the wavelength of the illuminating light. In the back illumination mode, the shifter pattern does not scatter the illuminating light at all. Laser beams of 780 nm, 633 nm, 532 nm, 515 nm and 488 nm, respectively, in wavelength were used as illuminating light beams. The shorter the wavelength, the higher is the particle detection signal. Although the shorter the wavelength, the higher the chromium pattern detection signal, the chromium pattern detection signal varies with the wavelength less sharply than the particle detection signal.

When inspecting a sample provided with a circuit pattern for foreign particles, the relation between the foreign particle detection signal provided when scattered light scattered by a foreign particle is detected and the pattern detection signal provided when scattered light scattered by the circuit pattern is detected must be taken into consideration. This relation is represented by discrimination ratio defined by:

(Discrimination ratio)=(Output of the detector provided when scattered light scattered by a foreign particle is detected)/(Output of the detector provided when scattered light scattered by the pattern is detected)

If the discrimination ratio is greater than "1", the foreign particle can be detected through the comparison (binarization) of the scattered light detection signals by an apparatus having a simple configuration. In a practical apparatus, the detection signal is affected by electrical noise, optical noise, vibrations of the mechanical parts, the variation of sensitivity of the detection system and such. Therefore, there must be a significant difference between the level of scattered light scattered by the foreign particle and that of scattered light scattered by the chromium pattern; that is, the greater the discrimination ratio, the higher is the foreign particle detecting ability.

The foregoing experimental results were examined to determine the wavelengths of illuminating light beams to enhance the detecting abilities of the front illumination mode and the back illumination mode to a maximum.

Figure 23:
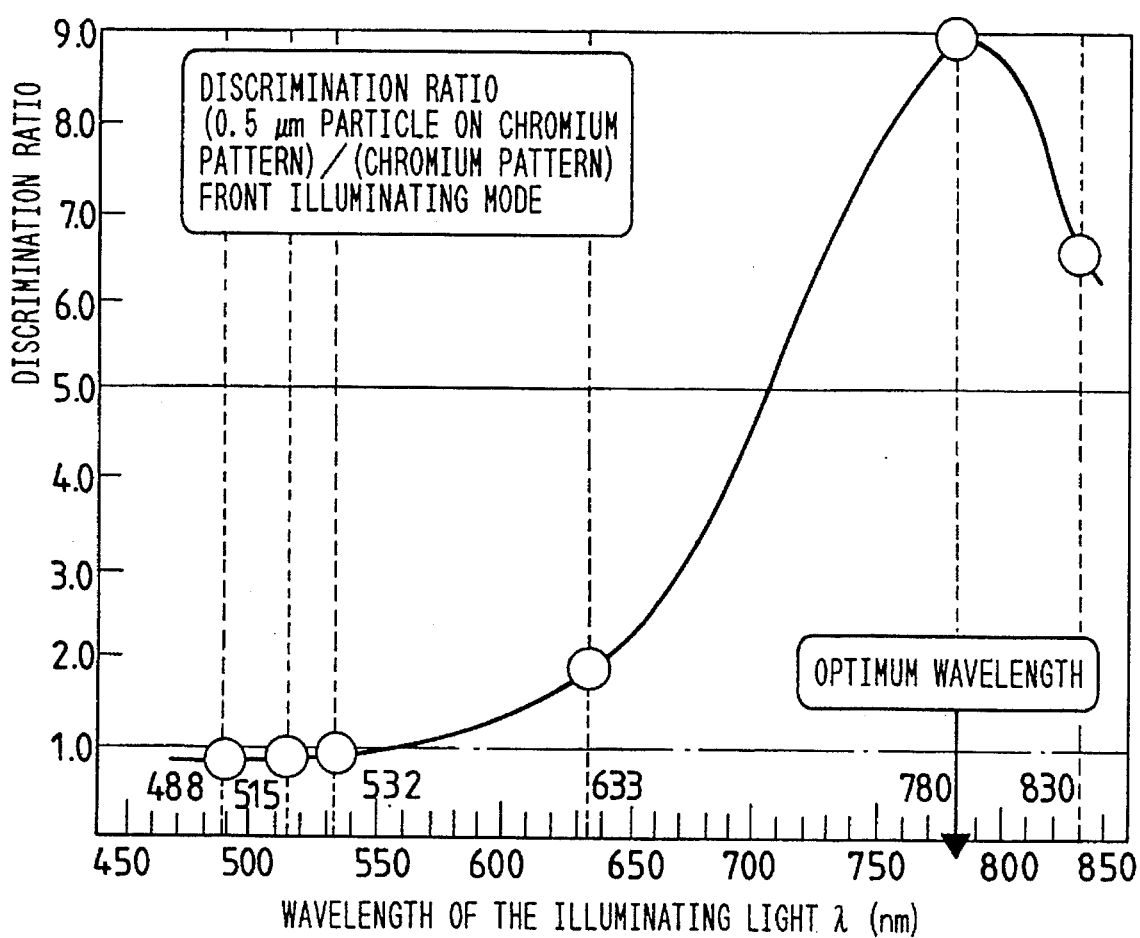
FIG. 23 is a graph showing the variation of the discrimination ratio (0.5 μm particle on the chromium pattern vs the chromium pattern) with the wavelength of the illuminating light beam used in the front illumination mode.
Figure 24:
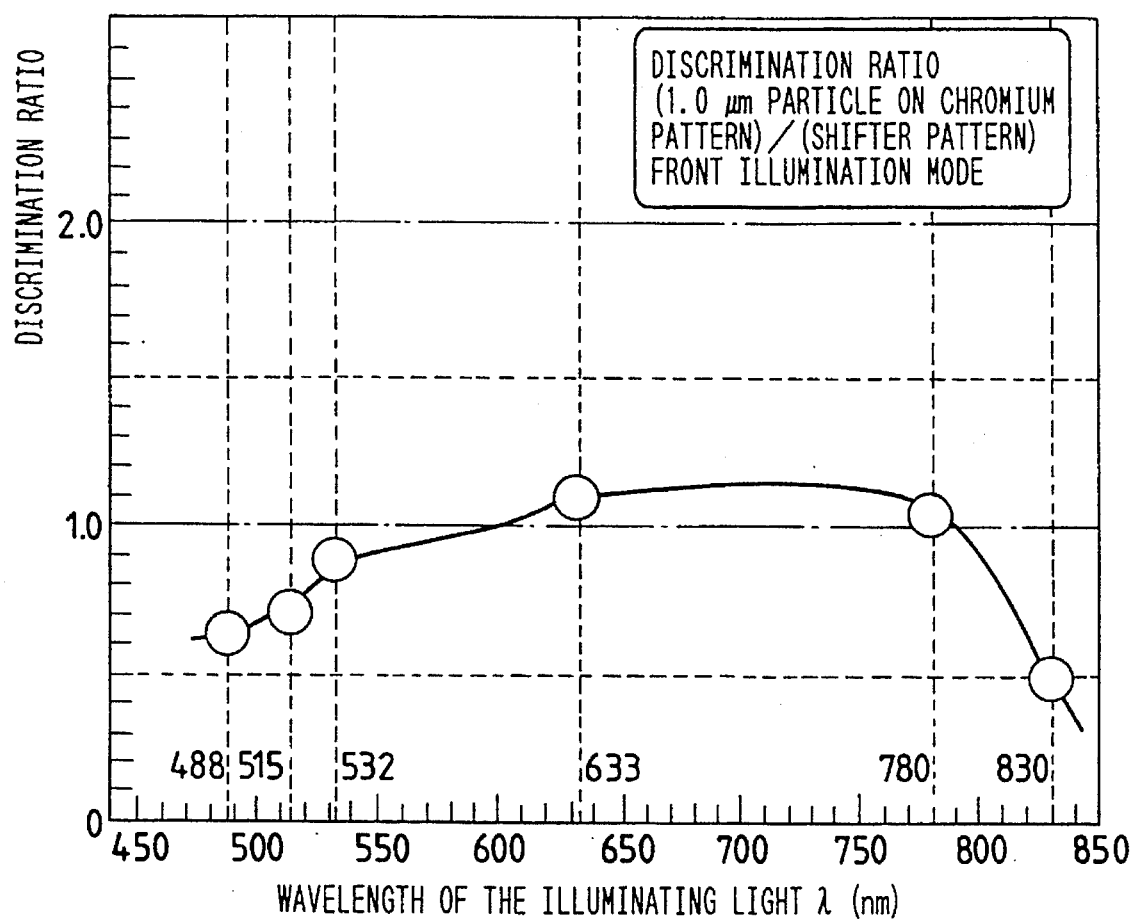
FIG. 24 is a graph showing the variation of the discrimination ratio (1.0 μm particle on the chromium pattern vs the phase shifter pattern) with the wavelength of the illuminating light beam used in the front illumination mode.

FIGS. 23 and 24 shows the variation of the discrimination ratio with the wavelength of the illuminating light beam in the inspection in the front illumination mode.

(1) FIG. 23: A 0.5 µm standard particle on the chromium pattern vs chromium pattern (Maximum value)

(2) FIG. 24: A 1.0 µm standard particle on the chromium pattern vs shifter pattern (Maximum value)

It is known from FIG. 23 that the 0.5 µm standard particle on a reticle not provided with any phase shift film can be most stably detected when an illuminating light beam having a wavelength around 780 nm is used.

It is known from FIG. 24 that the 1.0 µm standard particle on the chromium pattern of a phase shift reticle can be detected by using an illuminating light beam having a wavelength in the range of 600 nm to 800 nm.

From these facts known from FIGS. 23 and 24, it is considered that an illuminating light beam having a wavelength around 780 nm is an optimum illuminating light beam for the front illumination mode.

A light source capable of emitting such an optimum illuminating light beam having a wavelength around 780 nm is a semiconductor laser. It is obvious from FIG. 23 that the discrimination ratio achieved by using this optimum illuminating light beam is higher than that achieved by using a laser beam having a wavelength of 632.8 nm emitted by a red He—Ne laser, which has been widely used, and the optimum illuminating light beam secures stable foreign particle detection.

Figure 25:
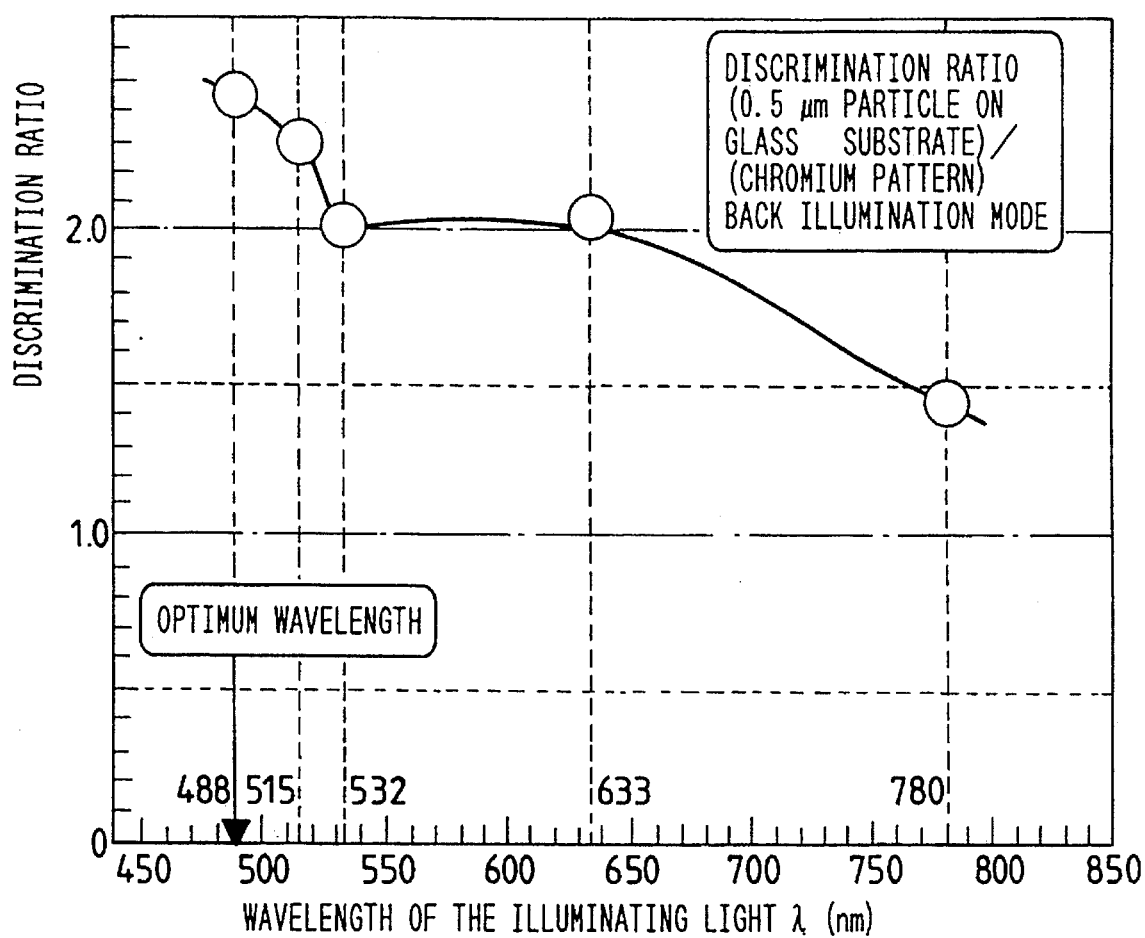
FIG. 25 is a graph showing the variation of the discrimination ratio (0.5 μm particle on the glass substrate vs the chromium pattern) with the wavelength of the illuminating light beam used in the back illumination mode.

FIG. 25 shows the variation of the discrimination ratio with the wavelength of the illuminating light beam in the inspection in the back illumination mode.

(1) FIG. 25: A 0.5 µm standard particle on the glass substrate vs the chromium pattern (Maximum value)

It is known from FIG. 25, the discrimination ratio reaches a maximum when an illuminating light beam having a wavelength of around 488 nm is used in the inspection in the back illumination mode.

A light source that emits light having a wavelength of about 488 nm is the Ar ion laser. The Ar ion laser having a large output capacity can be easily fabricated; an air-cooled Ar ion laser can provide an output as large as several tens of milliwatts and a water-cooled Ar ion laser can provide an output as large as several watts. Therefore, the detection signal when an Ar ion laser beam is used is higher than that when a red He—Ne laser beam is used.

Thus, from the foregoing, the present invention uses oblique illumination by an illuminating light beam having a wavelength of about 780 nm for the front illumination mode and oblique illumination by an illuminating light beam having a wavelength of about 488 nm in combination for the discriminative detection of foreign particles and a circuit pattern on a sample provided with a phase shift film.

The foregoing optimum wavelengths are selected on an assumption that the size of a minimum foreign particle among those to be detected is 0.5 µm. Since the greater the size of foreign particles, the higher is the detection signal, i.e., the amount of scattered light, a wavelength that makes the detection signal provided when a foreign particle having the minimum size a maximum is detected is the optimum wavelength. Since scattering is in similar correspondence in respect of the relation d/λ (d is the size of the particle and λ is the wavelength of the illuminating light beam). Accordingly, from the foregoing experimental results, an optimum wavelength is on the order of 1.6 d for the front illumination mode and on the order of 1.0 d for the back illumination mode, where d is the size of the smallest foreign particle among those to be detected.

Although the backward scattered light component increases if an illuminating light beam having a wavelength greater than the optimum wavelength is used for the front illumination mode, the total amount of scattered light decreases in inverse proportion to the fourth power of the wavelength of the illuminating light beam (Reyleigh scattering), entailing the reduction of the particle detection signal. If an illuminating light beam having a wavelength smaller than the optimum wavelength for the back illumination mode is used for oblique illumination, the forward scattered light component increases excessively and the amount of light that falls on the detection optical system decreases, reducing the particle detection signal. When the size of the smallest foreign particle among those to be detected is 0.5 µm, the wavelength for the front illumination mode must be in the range of 600 nm to 800 nm and the wavelength for the back illumination mode must be in the range of 450 nm to 550 nm.

Figure 1:
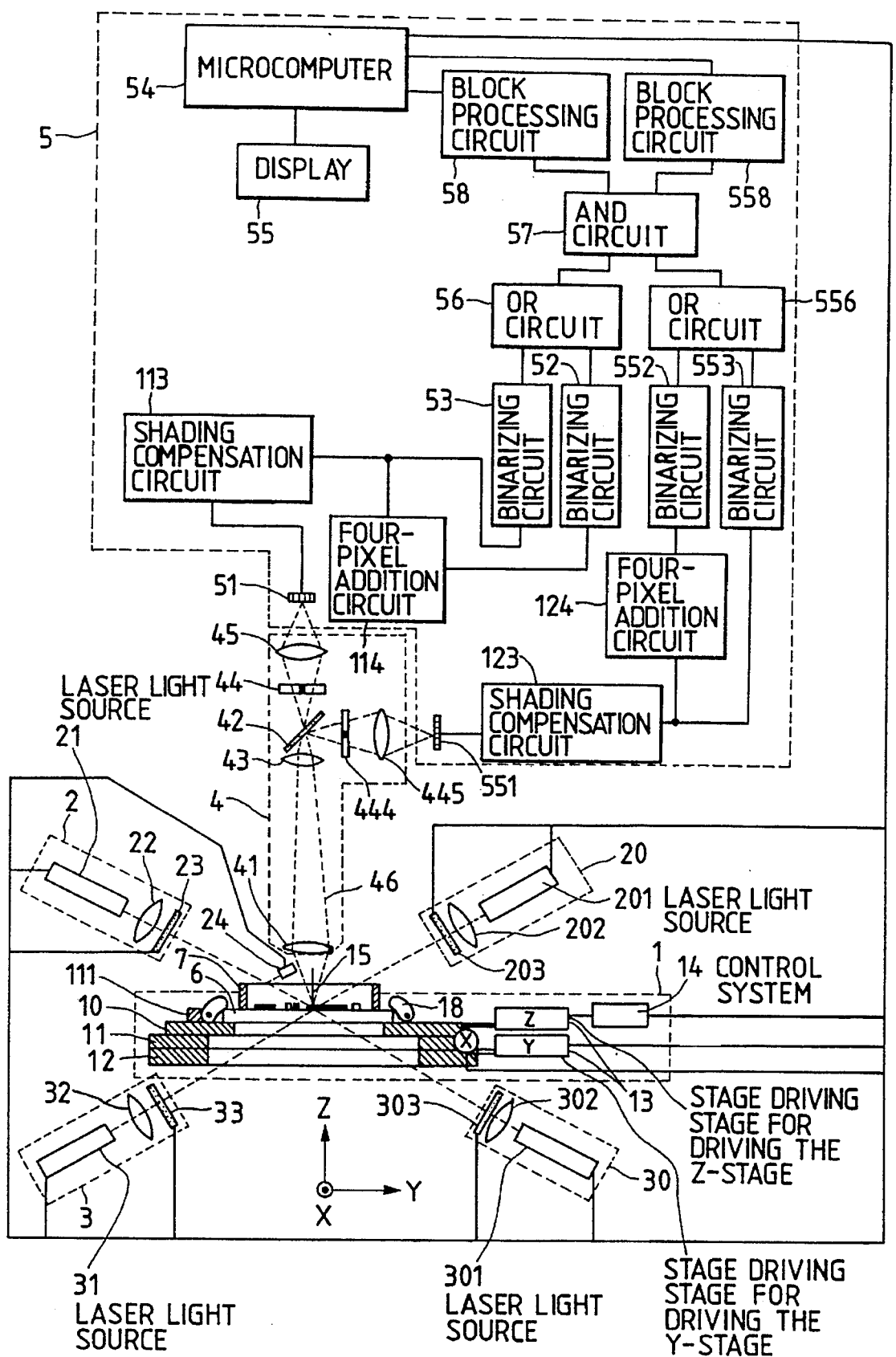
FIG. 1 is a diagrammatic view of a reticle inspecting apparatus in a first embodiment according to the present invention.

Referring to FIG. 1, an inspection stage unit 1 comprises a Z-stage 10 provided with a pellicle 7 and capable of being moved in the Z-direction, a fastening device 18 for fastening a reticle 6 on the Z-stage; an X-stage 11 for moving the Z-stage 10 supporting the reticle 6 in the X-direction; a Y-stage 12 for moving the Z-stage 10 supporting the reticle 6 in the Y-direction, a stage driving system 13 for driving the Z-stage 10, the X-stage 11 and the Y-stage 12 for movement, and a control system 14 for detecting the position of the reticle 6 with respect to the Z-direction to position the reticle 6 for focusing. The stages 10, 11 and 12 are controlled in a necessary accuracy for focusing during the inspection of the reticle 6.

Figure 2:
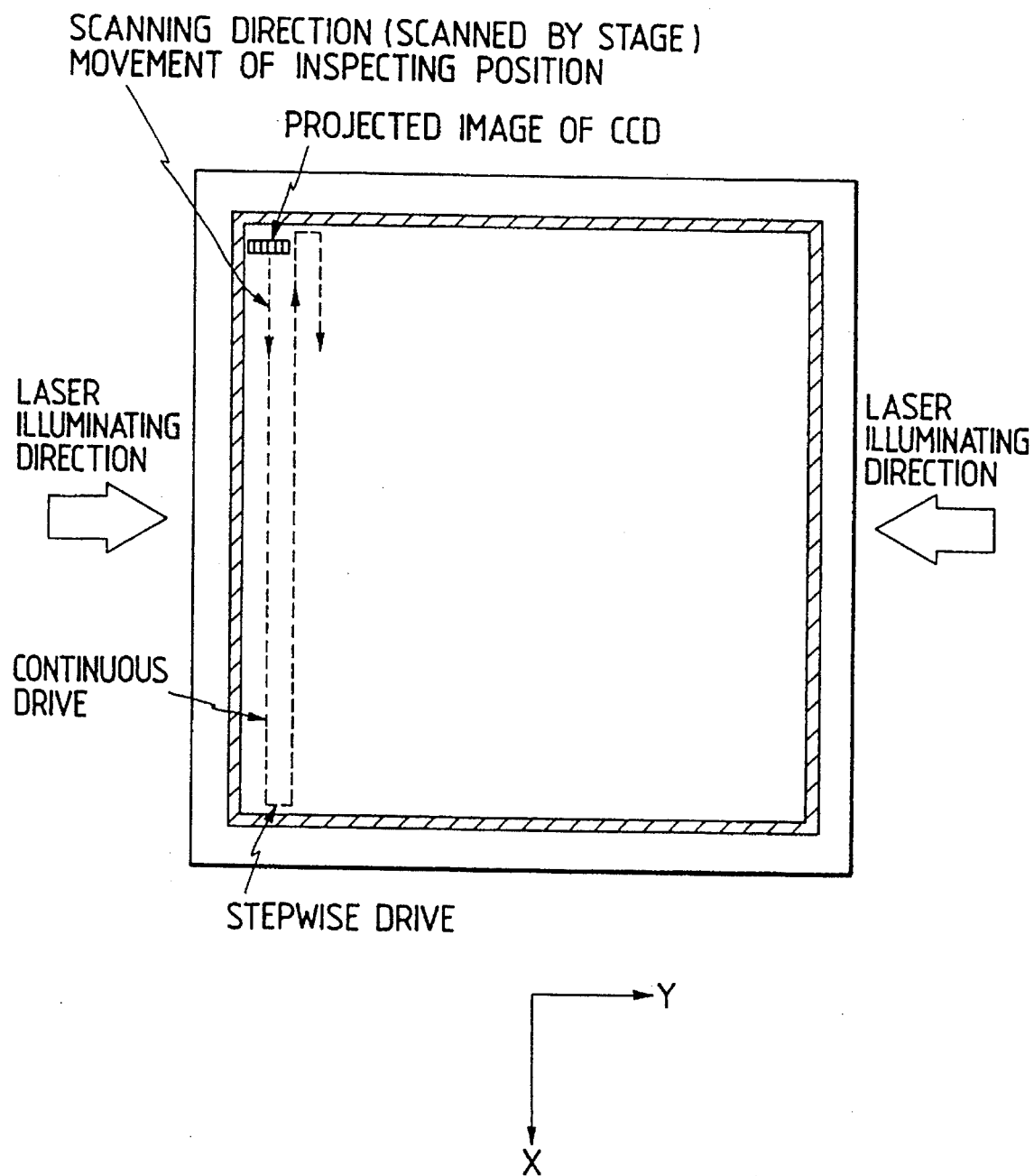
FIG. 2 is a plan view of a reticle for assistance in explaining a reticle scanning method in accordance with the present invention.

The X-stage 11 and the Y-stage 12 are controlled for movement for scanning along scanning lines as shown in FIG. 2 at an optional moving speed. For example, the X-stage is driven for a periodic movement in a half-cycle time of about 0.2 sec for uniformly accelerated motion, 4.0 sec for uniform motion, 0.2 sec for uniformly decelerated motion and about 0.2 for stopping, at a maximum velocity of about 25 mm/sec in an amplitude of 105 mm. The Y-stage 12 is driven for intermittent movement in the Y-direction in synchronism with the uniformly accelerated motion and the uniformly decelerated motion of the X-stage 11 at a step of 0.5 mm. If the Y-stage 12 is moved 200 times at a step of 0.5 mm, the reticle 6 can be moved 100 mm in about 960 sec and an area of 100 mm square can be scanned in about 960 sec.

The stage driving system 13 may be provided with an air micrometer, a laser interferometer or a device employing a stripe pattern to position the reticle 6 for focusing. In FIGS. 1 and 2, the X-direction, the Y-direction and the Z-direction are indicated by the arrows X, Y and Z, respectively.

The reticle inspecting apparatus has a first front illuminating unit 2, a second front illuminating unit 20, a first back illuminating unit 3 and a second back illuminating unit 30, which are individual systems and the same in configuration. The front illuminating units 2 and 20 are provided respectively with laser light sources 21 and 201 which emit light beams of 780 nm in wavelength. The back illuminating units 3 and 30 are provided respectively with laser light sources 31 and 301 which emit light beams of 488 nm in wavelength. Laser beams emitted by the laser light sources 21, 201, 31 and 301 are condensed respectively by condenser lenses 22, 202, 32 and 302 to illuminate a circuit pattern formed on the front surface of the reticle 6. The incidence angle i of each of the light beams emitted by the laser light sources 2, 20, 3 and 30 on the circuit pattern must be greater than about 30° to avoid the collision of the light beam on the objective lens 41 of a detection optical system 4 and must be smaller than about 80° to avoid the collision of the same on the pellicle 7 mounted on the reticle 6. Therefore, about 30°<i<about 80°. The illuminating units are provided respectively with shutters 23, 203, 33 and 303 which open to pass the light beams emitted by the corresponding light sources and close to cut off the same, respectively, and, if necessary, can be operated individually.

Figure 3:
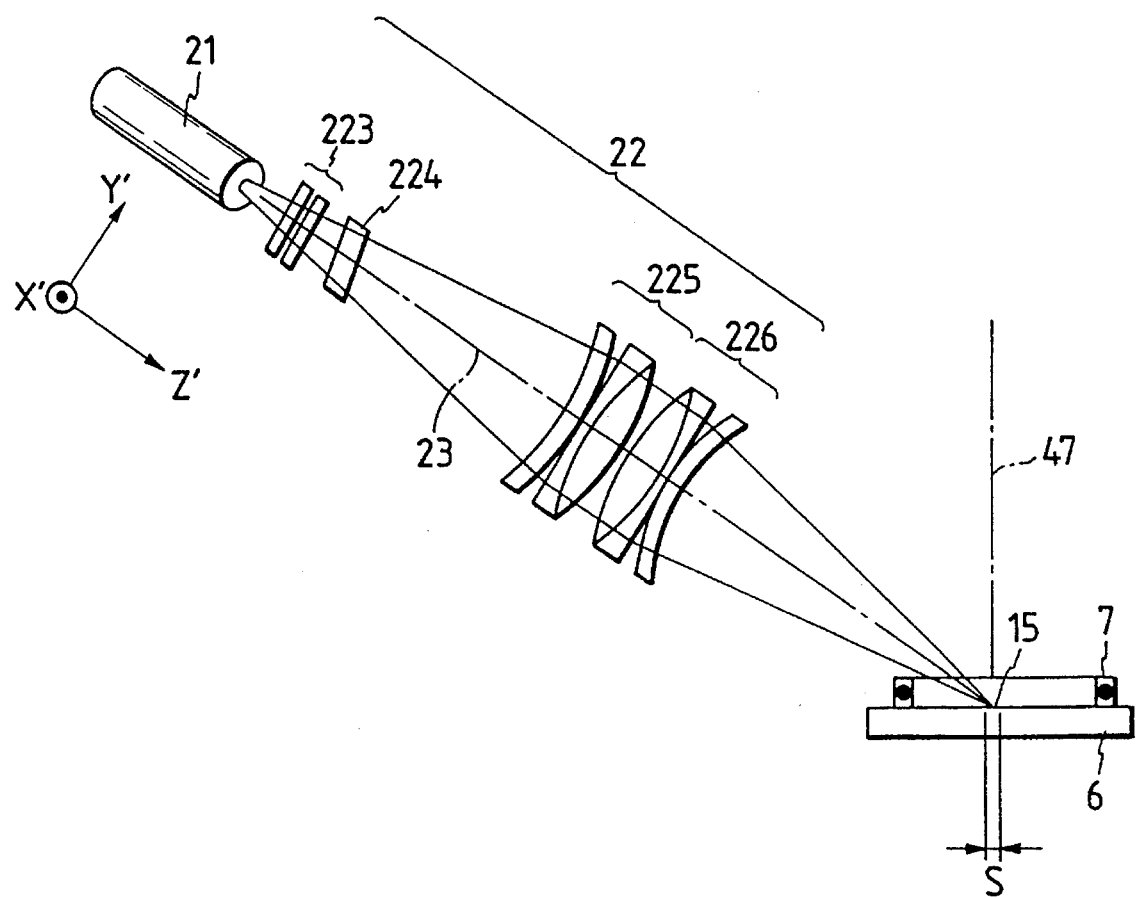
FIG. 3 is a diagrammatic view of one of the symmetrically disposed illuminating units included in the reticle inspecting apparatus of FIG. 1.

Since the first front illuminating unit 2, the second front illuminating unit 20, the first back illuminating unit 3 and the second back illuminating unit 30 are the same in configuration, only the first front illuminating unit 2 will be described with reference to FIG. 3, in which parts like or corresponding to those shown in FIG. 1 are denoted by the same reference characters. The first front illuminating unit 2 is provided with the condenser lens 22 consisting of a convex lens 223, a cylindrical lens 224, a collimator lens 225 and a condenser lens 226.

The laser light sources 21 and 201 of the front illuminating units 2 and 20 are disposed so that light beams emitted by the laser light sources 21 and 201 are linearly polarized light beams (s-polarized light beams) having the electric vector which remains pointing to the X'-direction. The s-polarized light beams are used because the reflectivity of the s-polarized light beams incident on a glass substrate at an incidence angle i of about 60° is about five times greater than that of the p-polarized light beams (linearly polarized light having the electric vector which remains pointing to the Y'-direction) and hence the s-polarized light beams are more suitable for detecting small particles than the p-polarized light beams.

The laser light sources 31 and 301 of the back illuminating units 3 and 30 are disposed so that light beams emitted by the laser light sources 31 and 301 are s-polarized light beams because experiments showed that the discrimination ratio when the s-polarized light beam is used is greater than the discrimination ratio when the p-polarized light beam is used. However, in some cases, the p-polarized light beam is preferred to the s-polarized light beam, taking into consideration the transmittance of the substrate.

The present invention uses spatial filters disposed on the Fourier transform plane of the detection optical system 4 to discriminate between foreign particles and the circuit pattern. The use of a collimated light beam reduces the spread of diffracted light diffracted by the circuit pattern to increase the discrimination ratio. However, the use of gathered light of high intensity will raise the output level of the detector and improve the SN ratio.

If the NA of the converging system is about 0.1 and the diameter of the laser beam is reduced to about 10 μm to increase the intensity of the laser beam emitted by each of the illuminating units 2, 20, 3 and 30, the depth of focus is as small as about 30 μm, which is smaller than the size (500 μm) of the entire area S of an inspection field (FIG. 3) and the entire area S of the inspection field 15 cannot be brought into focus. In this reticle inspecting apparatus, the cylindrical lens 214 is turned about the X'-axis as shown in FIG. 3 to bring the entire area S of the inspection field 15 into focus when the incidence angle i is, for example, 60°. Accordingly, even if the detectors 51 and 551 of a signal processing system 5 are one-dimensional solid-state imaging devices and the inspection area of the inspection field 15 has a linear shape, the linear inspection area can be uniformly illuminated in a high illuminance.

When the cylindrical lens 224 is turned about both the X'-axis and the Y'-axis (FIG. 3), the entire area S of the inspection field 15 can be uniformly and linearly illuminated in a high illuminance even if the light beam is projected from an optional direction so as to fall on the reticle at an incidence angle i of 60°.

Figure 37:
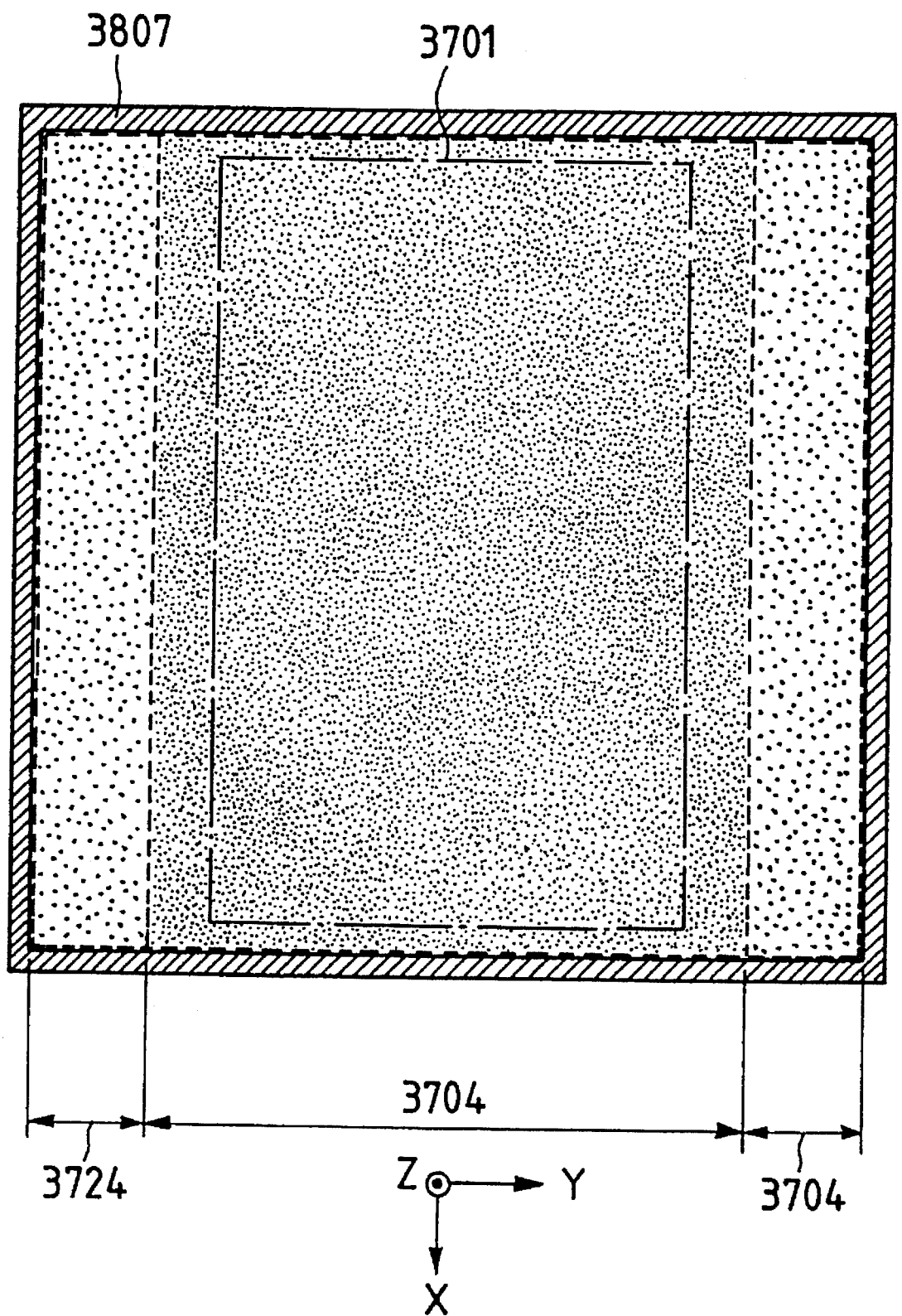
FIG. 37 is a plan view of assistance in explaining the change of illuminated units in accordance with the present invention.

The shutters 23 and 203 intercept the light beams emitted by the laser light sources 21 and 201, respectively, when necessary. The following cases need the control of the light beams by the shutters. FIGS. 38(A) to 38(C) show the relation between the reticle 6, the pellicle 7, the oblique illuminating light beam 3802 projected by the illuminating unit 2, an oblique illuminating light beam 3820 projected by the illuminating unit 20, an oblique illuminating light beam 3803 projected by the illuminating unit 3, an oblique illuminating light beam 3830 projected by the illuminating unit 30 and an inspection field 15, i.e., an illuminated position. When the stage is moved in the positive direction along the Y-axis from the position shown in FIG. 38(B), the illuminating light beam 3820 projected by the illuminating unit 20 is intercepted by the frame 3807 of the pellicle 7 mounted on the reticle 6 upon the arrival of the stage at a position shown in FIG. 38(A). When the stage is moved in the negative direction along the Y-axis from the position shown in FIG. 38(B), the illuminating light 3802 projected by the projected by the illuminating unit 2 is intercepted by the frame 3807 of the reticle 7 upon the arrival of the stage at a position shown in FIG. 38(C). When the stage is at the position shown in FIG. 38(A) or 38(C), part of the illuminating light is obstructed, the illuminance in the inspection field 15 is reduced and the degree of reduction varies every moment, which makes stable illumination impossible. Moreover, part of the obstructed illuminating light beams become stray light which affects adversely to defect detection. Therefore, the illuminating light beam 3820 (3802) must be cut off by the shutter 203 (23) before the same is obstructed. Thus, the illuminated area which can be illuminated by the illuminating system 2 (20) is dependent on the relation between the incidence angle of the illuminating light beam 3802 (3820) and the frame 3807. Referring to FIG. 37 showing illuminated areas, an area 3704 is illuminated in an illuminating mode shown in FIG. 38(B), an area 3724 is illuminated in an illuminating mode shown in FIG. 38(C), an area 3704 is illuminated in an illuminating mode shown in FIG. 38(A), when the frame 3807 is 102 mm long, 102 mm wide and 6.3 mm high, and the angle between the optical axis of each illuminating unit and the front surface of the reticle 6 provided with the circuit pattern is 30°. As shown in FIG. 37, the entire area 3701 of the surface of a chip for a 64M DRAM is included in the area 3704.

The same illuminating modes as the foregoing illuminating modes concerning the front illuminating units 2 and 20 occur to the back illuminating units 3 and 30 when the same frame 3807 holding a pellicle is attached to the back surface of the reticle 6.

Figure 54:
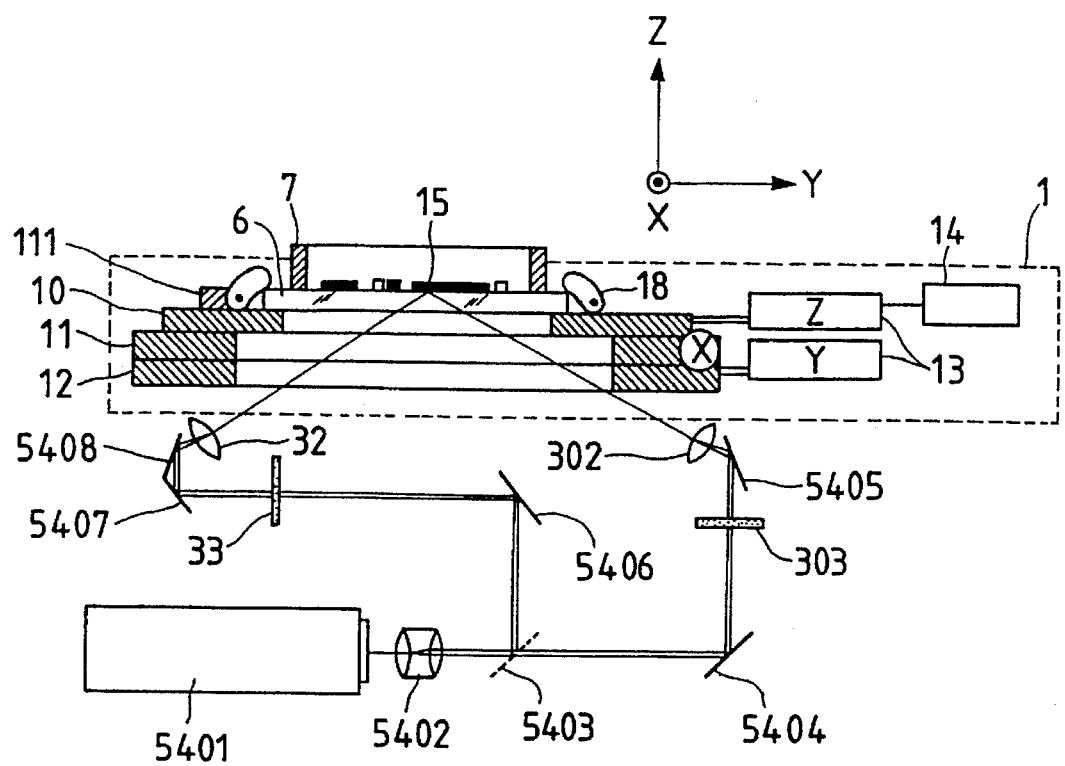
FIG. 54 is a schematic sectional view of a back illuminating system in accordance with the present invention.
Figure 55:
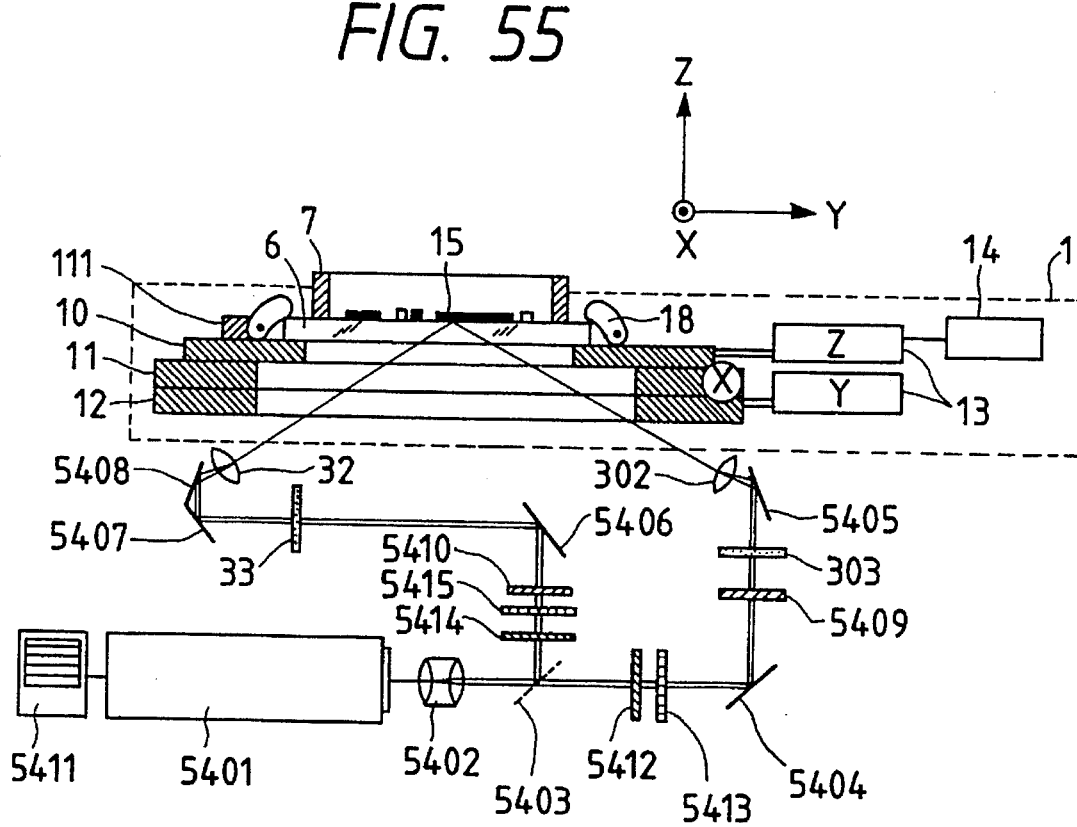
FIG. 55 is a schematic sectional view of a back illuminating system in accordance with the present invention.

Although the back illuminating units 3 and 30 of the reticle inspecting apparatus of FIG. 1 are provided respectively with the small laser light sources 31 and 301 having a comparatively small output capacity, the two small laser light sources 31 and 301 may be substituted by a single large laser light source having a comparatively large output capacity and the laser beam emitted by the large laser light source may be divided into two laser beams as shown in FIG. 54. A back illuminating unit shown in FIG. 54 corresponds to the back illuminating units 3 and 301 shown in FIG. 1. Since the laser beam emitted by a single laser light source 5401 is divided into two laser beams, the back illuminating unit shown in FIG. 54 has a comparatively long optical path length and, consequently, the laser beam emitted by the laser light source 5401 is liable to be disturbed and to expand while traveling along the long optical path. Therefore, the laser beam is expanded by a beam expander 5402 to increase its diameter, and then the expanded laser beam is divided into two laser beams by a beam divider 5403 so that the two laser beams travel along two optical paths, respectively. One of the optical paths corresponds to the back illuminating unit 3 of FIG. 1, and a shutter 33, reflecting mirrors 5406, 5407 and 5408, and a condenser lens 32 are arranged on the optical path. The laser light beam is guided by the reflecting mirrors 5406, 5407 and 5408 to the condenser lens 32, and then the condenser lens 32 concentrates the laser beam on a reticle 6. This back illuminating unit is only an example and may be substituted by any suitable back illuminating unit of another configuration. When the laser beam is a linearly polarized laser beam, the reflecting mirrors arranged on the optical path must be such as will not affect adversely to the plane of polarization of the laser beam. The beam divider 5403 may be of a transmittance division type, a polarization division type or, if the laser light source is such as is capable of emitting light having a plurality of wavelengths, such as an argon laser, a wavelength division type. Desirably, the laser beam emitted by the laser light source 5401 is divided into two laser beams having equal intensities. When it is difficult to divide the laser beam into two equal laser beams, the intensities of the two laser beams as divided may be adjusted to equal intensities by variable ND filters 5409 and 5410 provided respectively on the branch optical paths as shown in FIG. 55. When the laser beam is divided by polarization, half-wave plates 5414 and 5412 are provided respectively on the two branch optical paths as shown in FIG. 55 in order that the respective planes of polarization of the two laser beams on the surface of the reticle 6 are the same. The purity of polarization of the two laser beams may be improved by polarizers 5415 and 5413.

When the laser beam emitted by the single laser light source is divided into two laser beams, the two laser beams are transmitted along two branch optical paths, and an inspection field is illuminated with the two laser beams, the two laser beams interfere with each other on the surface of the reticle 6 to form interference fringes and, consequently, the inspection field is illuminated very irregularly. In such a case, the two branch optical paths are formed so that the optical path difference between the two branch optical paths is not shorter than the coherence length, for example a length in the range of several millimeters to several meters, for the laser beam emitted by the laser of the laser light source. When the beam divider of a wavelength division type is employed, the two laser beams do not interfere with each other and hence the influence of interference between the two laser beams traveling along the two branch optical paths need not be taken into consideration. If the oscillation wavelengths of 488 nm and 515 nm among those of an argon laser are used, detection sensitivities with 488 nm and 515 nm are not greatly different from each other because the difference between 488 nm and 515 nm is small, and irregular detection sensitivity caused by the effect of interference, which is difficult to analyze, can be obviated by a minute wavelength difference caused by the shape of a defect, such as a foreign particle.

Figure 56:
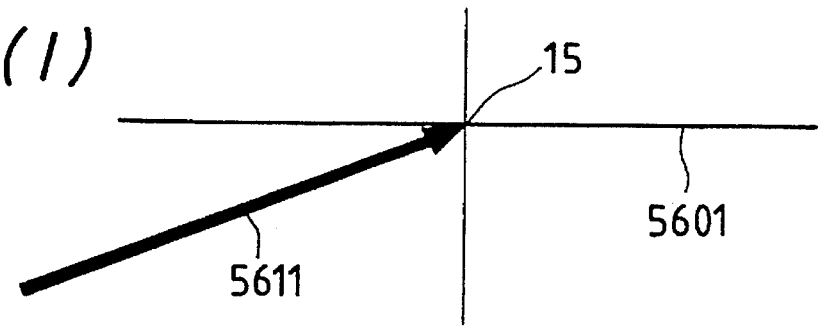
FIGS. 56(1) to 56(4) are diagrammatic views of assistance in explaining problems in a back illuminating system.
Figure 56:
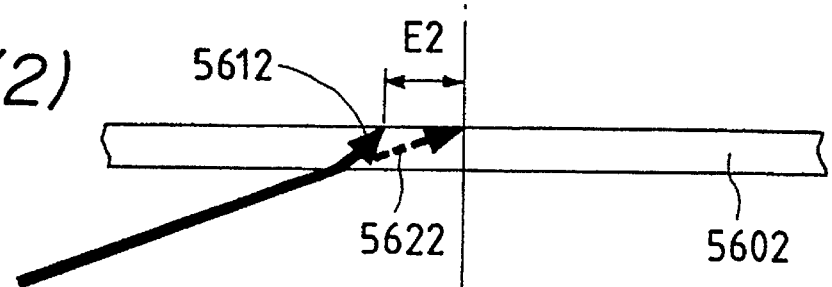
Figure 56:
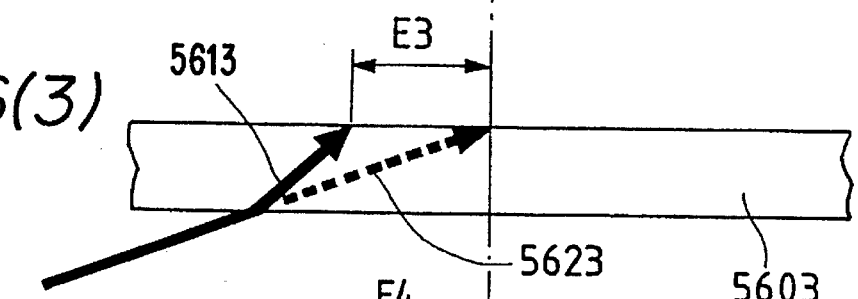
Figure 56:
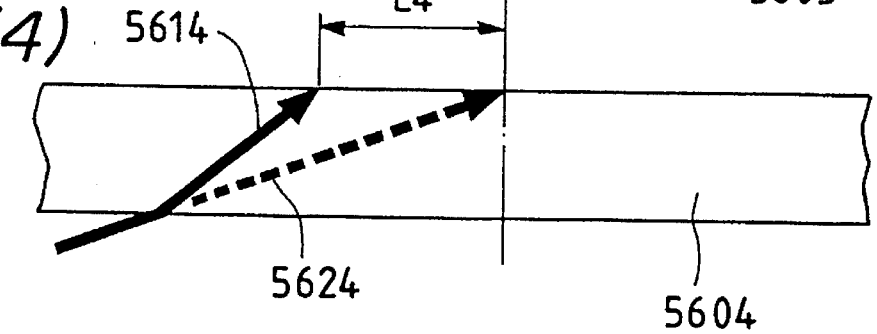

In the back illuminating mode, the optical path length of an optical path along which the illuminating light beam travels is dependent on the thickness of the glass plate, i.e., the substrate of the reticle. Even if the optical path is formed so that the illuminating light beam falls on the inspection field 15 on a reticle 5601 of substantially zero in thickness as shown in FIG. 56(1), the illuminating light beam travels through a reticle 5602 having a comparatively small thickness along a path 5612 deviating from a path 5622 reaching the inspection field 15 and illuminates an illuminated position dislocated by an error E2 from the inspection field 15 as shown in FIG. 56(2). Similarly, the illuminating light beam travels through a reticle 5603 having a middle thickness along a path 5613 deviating from a path 5623 reaching the inspection field 15 and illuminates an illuminated position dislocated by an error E3 as shown in FIG. 56(3), and the illuminating light beam travels through a reticle 5604 having a comparatively large thickness along a path 5614 deviating from a path 5624 reaching the inspection field 15 and illuminates an illuminated position dislocated by an error E4 as shown in FIG. 56(4). Since photomasks, such as reticles are formed on substrates having different thicknesses, such as 2.3 mm, 4.6 mm and 6.3 mm, effective measures must be taken to prevent the dislocation of an illuminated position from a desired inspection field.

Figure 57:
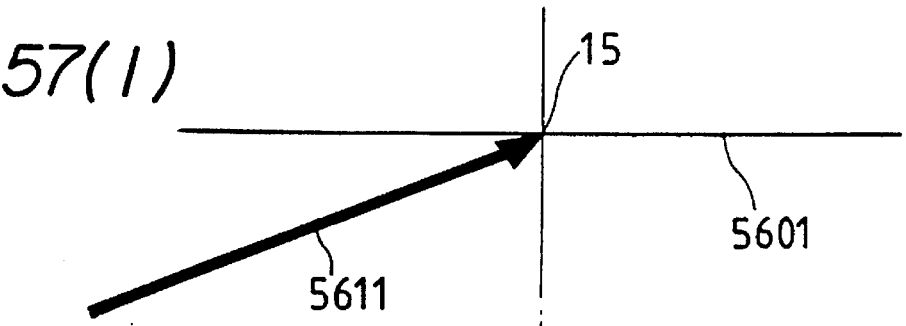
FIGS. 57(1) to 57(4) are diagrammatic views of assistance in explaining a principle on which problems in a back illuminating system are solved.
Figure 57:
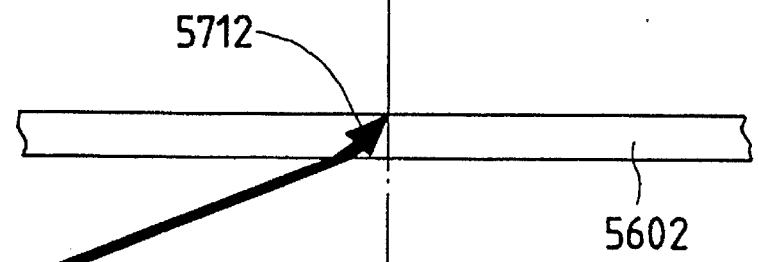
Figure 57:
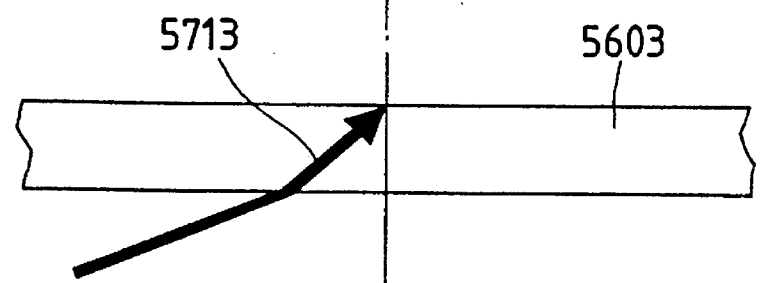
Figure 57:
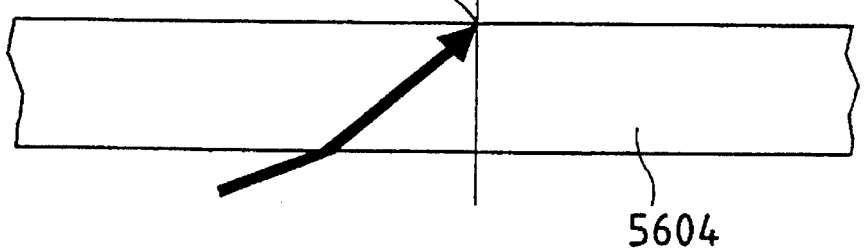
Figure 58:
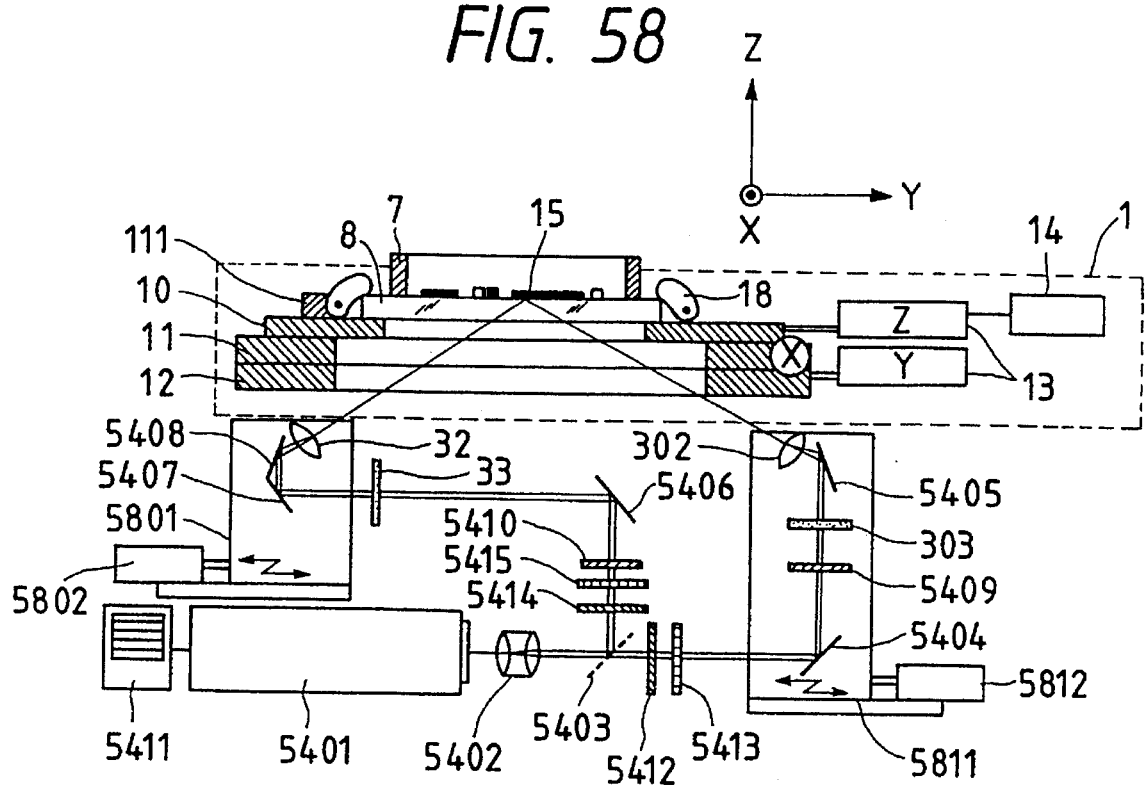
FIG. 58 is a schematic sectional view of a back illuminating system in accordance with the present invention.
Figure 59:
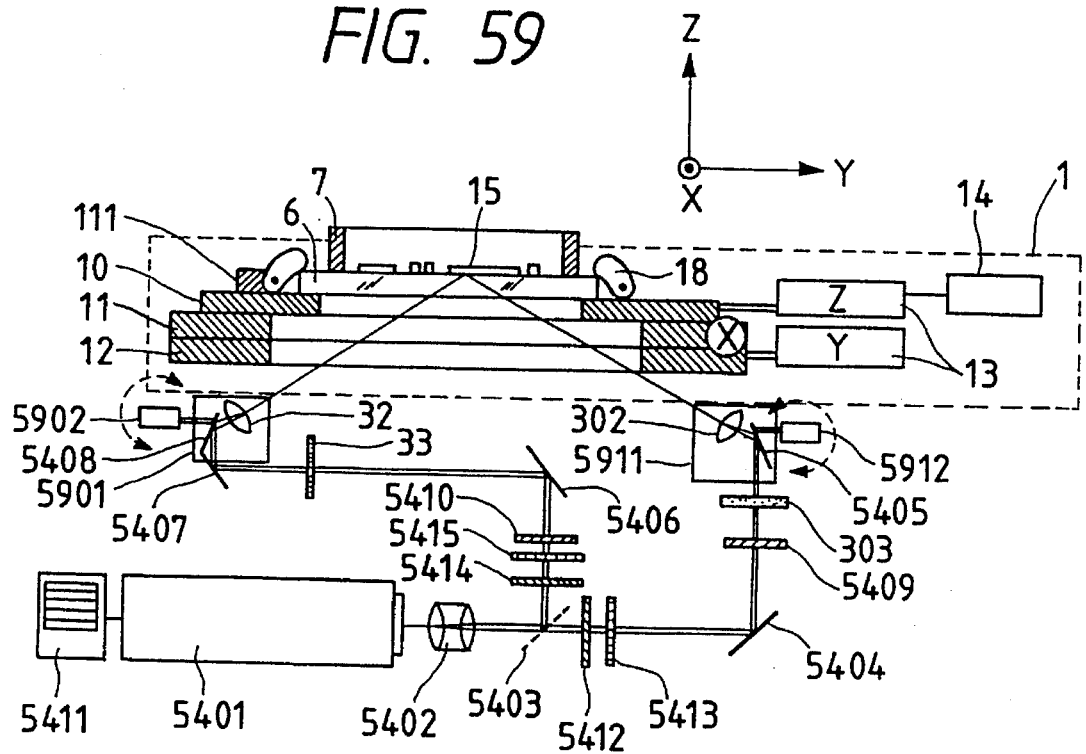
FIG. 59 is a schematic sectional view of a back illuminating system in accordance with the present invention.

Although the dislocation of the illuminated position from the inspection field 15 attributable to the effect of the thickness of the substrate is not any problem if an illuminating light beam capable of illuminating a wide area on the reticle including the errors E2 to E4 is used, the use of such an illuminating light beam reduces the illuminance of the inspection field and reduces the S/N ratio. FIGS. 57(1) to 57(4) shows means for illuminating the inspection field 15 regardless of the thickness of the reticle. An illuminating light beam is transmitted so as to travel through the reticle 5602 along an optical path 5712 as shown in FIG. 57(2), through the reticle 5603 along an optical path 5713 as shown in FIG. 57(3) and through the reticle 5604 along an optical path 5714 as shown in FIG. 57(4) so that the illuminating light beam falls on a inspection field corresponding to the inspection field 15 on a reticle of virtually zero in thickness on which the illuminating light beam will fall when the illuminating light beam travels along a straight optical path 5611. FIG. 58 shows a back illuminating unit provided, in addition to the components of the back illuminating unit of FIG. 55, with optical path shifting devices 5801 and 5811, and driving mechanisms 5802 and 5812 for driving the optical path shifting devices 5801 and 5811 to shift the optical paths according to the thickness of the reticle. FIG. 59 shows a back illuminating unit provided, in addition to the components of the back illuminating unit of FIG. 55, with angular position changing devices 5901 and 5911 for changing the angular positions of the reflecting mirrors 5408 and 5405, and driving mechanisms 5902 and 5912 for driving the angular position changing devices 5901 and 5911 to change the illuminating angle according to the thickness of the reticle.

Figure 60:
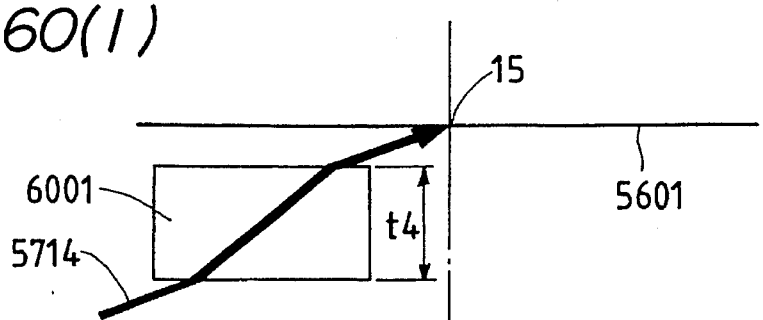
FIGS. 60(1) to 60(4) are diagrammatic views of assistance in explaining a principle on which problems in a back illuminating system are solved.
Figure 60:
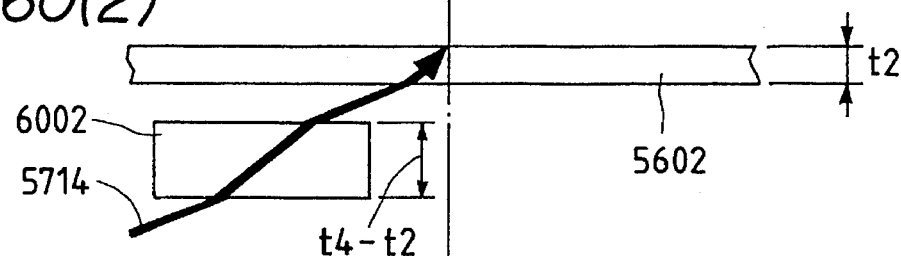
Figure 60:
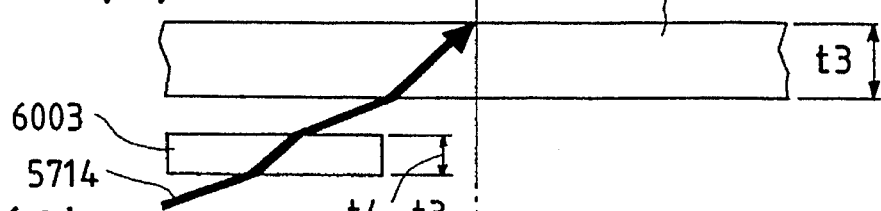
Figure 60:
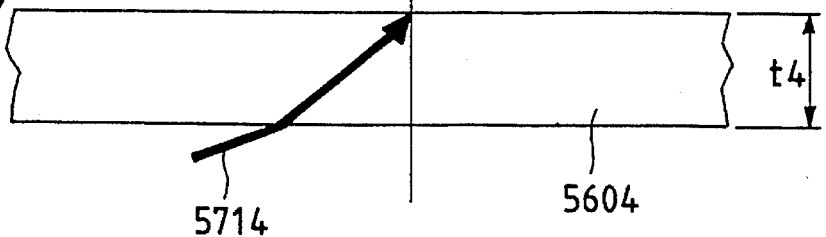
Figure 61:
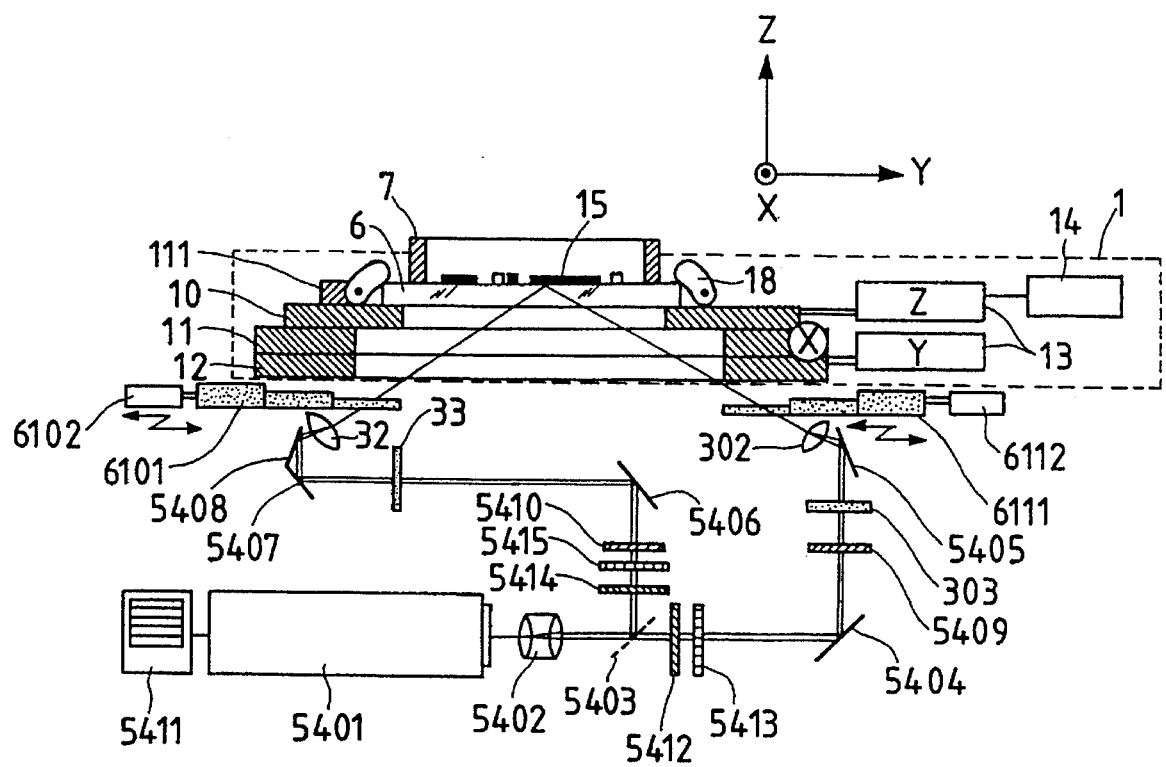
FIG. 61 is a schematic sectional view of a back illuminating system in accordance with the present invention.

The influence of the difference in the thickness of the reticle on the optical path is dependent on the difference in refractive index between the substrate of the reticle and the optical path (the influence disappears if the difference in refractive index is zero). The difference in refractive index brings about optical path difference in the focusing system of the illuminating unit. That is, when focusing an illuminating light beam the difference in thickness of the reticle affects focusing and, if the depth of focus of the focusing system is not sufficiently large, focus must be adjusted to adjust the focusing position, which requires a complicated apparatus. However, if the change in the optical path length due to the difference in thickness of the reticle is corrected by some means, the optical path shifting device and the angular position changing devices as shown in FIGS. 58 and 59 are unnecessary. FIGS. 60(1) to 60(4) illustrates a principle of correcting optical path length. When illuminating reticles respectively of 0, t2, t3 and t4 in thickness, an optical path length correcting plate of t4 in thickness is disposed under the reticle of 0 in thickness, an optical path length correcting plate of (t4–t2) is disposed under the reticle of t2 in thickness, an optical path length correcting plate of (t4–t3) in thickness is disposed under the reticle of t3 in thickness, and no optical path length correcting plate is disposed under the reticle of t4 in thickness, so that all the optical path lengths respectively for the reticles of 0, t2, t3 and t4 in thickness are equal to each other, and the illuminated positions and focal positions on all the reticles correspond exactly to each other. FIG. 61 shows a back illuminating unit provided, in addition to the components of the back illuminating unit of FIG. 55, with optical path length correcting units 6101 and 6111 each provided with a plurality of optical path length correcting plates of different thicknesses, and driving mechanisms 6102 and 6112 for driving the optical path length correcting units 6101 and 6111. The optical path length correcting units may be such as are provided with liquid means capable of being deformed, or are capable of continuously changing optical path length by an electrooptic means.

The reticle inspecting apparatus of FIG. 1 is provided with a detection optical system 4 for measuring the transmittance of the pellicle. The transmittance of the pellicle is affected slightly by the thickness of the pellicle and the antireflection film coating the pellicle. The influence of the thickness and the antireflection film on the transmittance is insignificant with light that penetrates the pellicle perpendicularly, such as the scattered light from the reticle. However, in some cases, the influence of the thickness and the antireflection film on the transmittance is significant with light that penetrates the pellicle obliquely, such as the illuminating light beam for illuminating the reticle. This problem can be solved by measuring the transmittance of the pellicle of each reticle and correcting the results of detection by using the measured transmittance of the pellicles. However, the transmittance of the pellicle cannot directly be measured because the pellicle is mounted on the reticle. Therefore, the detection optical system 4 measures the intensity of the illuminating light beam projected by the illuminating unit and reflected from the pellicle and that of the illuminating light beam as emitted by the light source, determines the reflectance of the pellicle on the basis of the measured data, and calculates transmittance by using: (Transmittance)=1–(Reflectance). Then, the results of detection are corrected by using the calculated transmittance of the pellicle.

Referring again to FIG. 1, the detection optical system 4 comprises the objective lens 41 disposed opposite to the front surface of the reticle 6, a field lens 43 disposed near the focal point of the objective lens 41, and a wavelength separating mirror 42. The light incident on the detection optical system 4 is separated into a scattered light component and a diffracted light of the front illuminating units 2 and 20, and those of the back illuminating units 3 and 30. The separated light components travel through spatial filters 44 and 444 disposed on Fourier transform planes with respect to the inspection field 15 on the reticle 6 and each having a band-like screening portion and light-transmissive portions on the opposite sides of the band-like screening portion, and focusing lenses 45 and 445 and form images of the inspection field 15 on the reticle 6 on the detectors 51 and 551 of the signal processing system 5, respectively. The field lens 43 forms an image of a focus position 46 above the objective lens 41 on the spatial filters 44 and 444.

Figure 17:
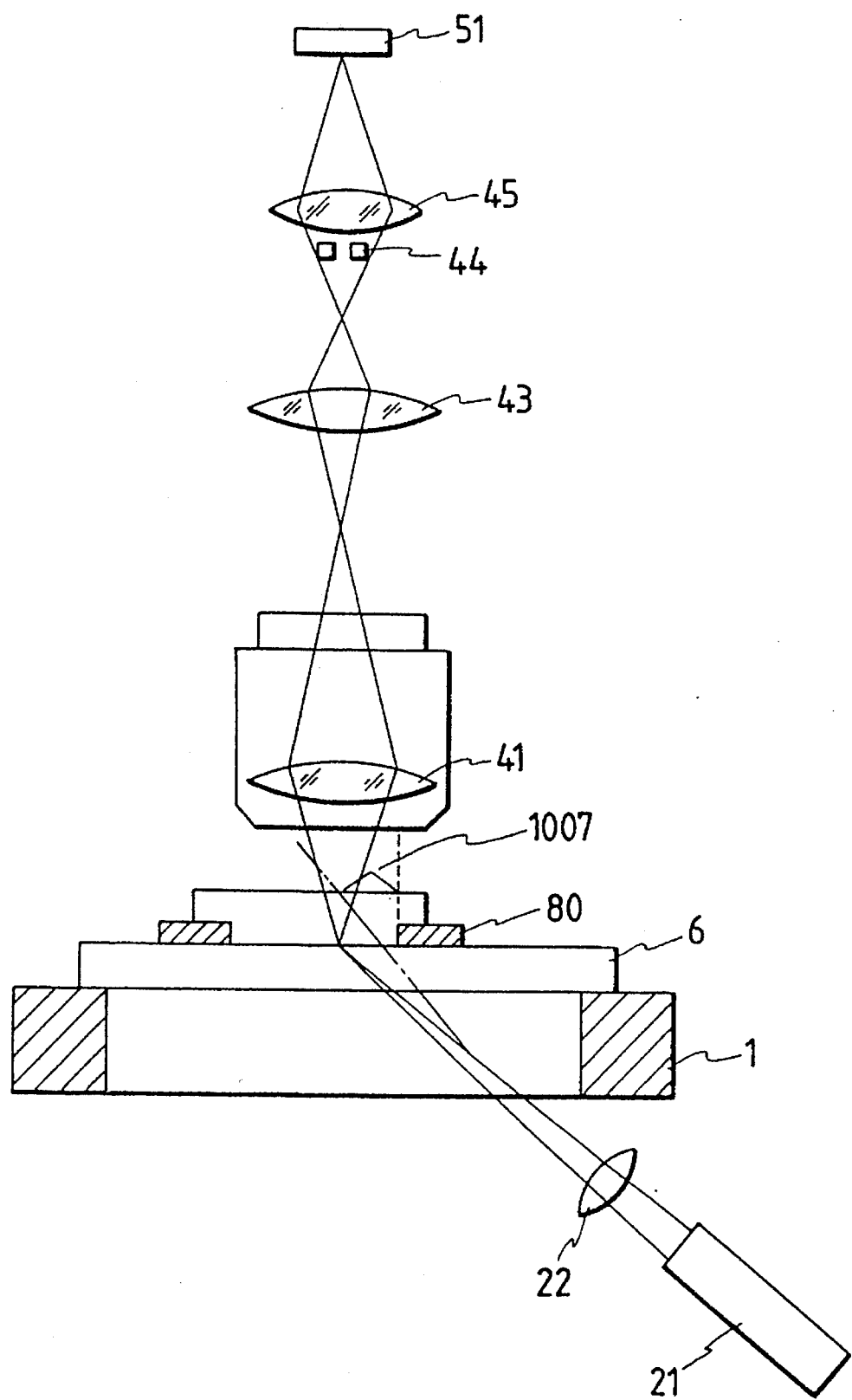
FIG. 17 is a diagrammatic view showing the configuration of a reticle inspecting apparatus embodying the present invention.
Figure 34:
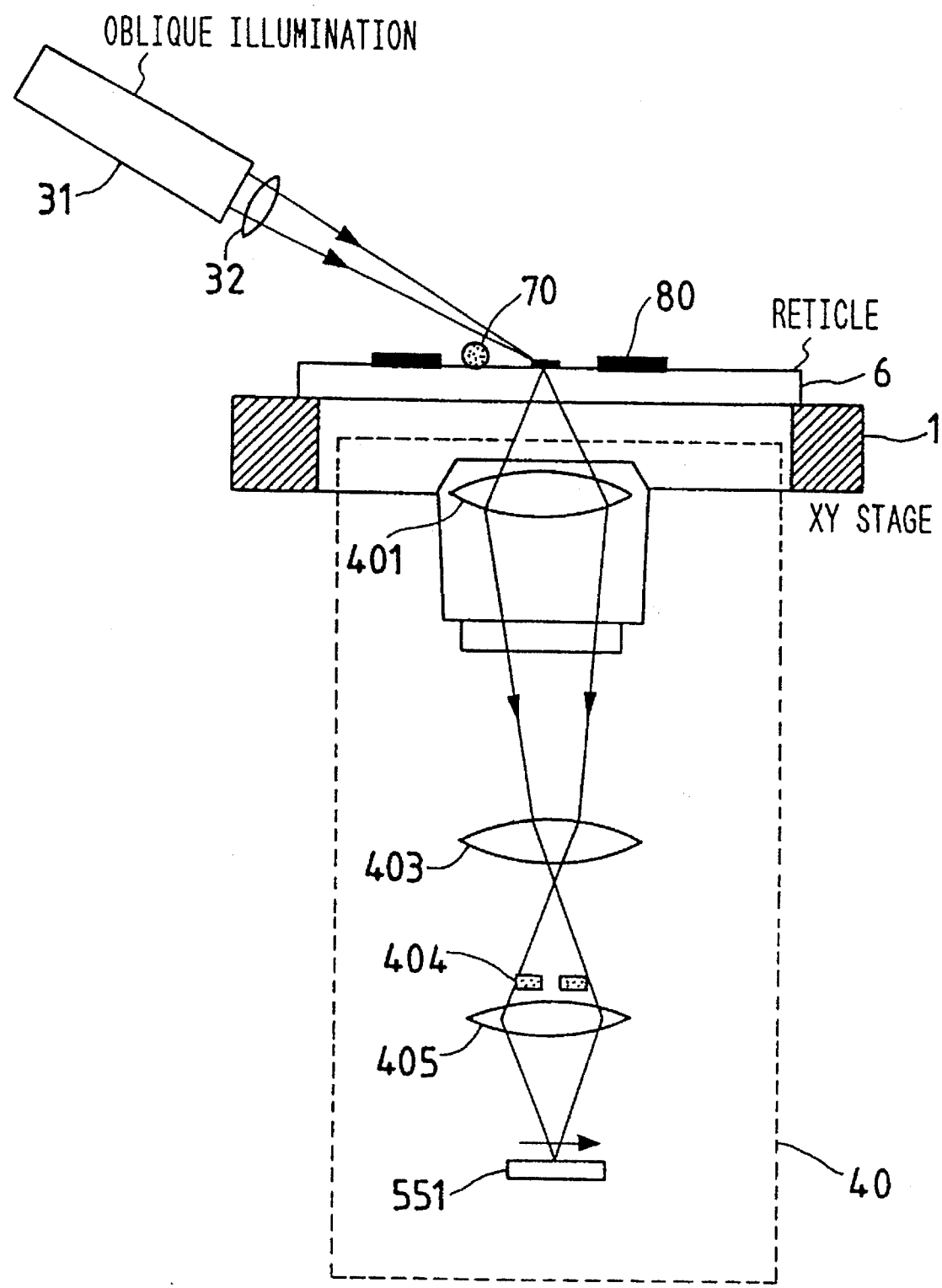
FIG. 34 is a diagrammatic view of a reticle inspecting apparatus in a second embodiment according to the present invention.

FIG. 17 shows a reticle inspecting apparatus of the back illuminating unit. The respective positions of an illuminating unit 3 and a detection optical system 4 included in the reticle inspecting apparatus may be interchanged with respect to the reticle 6. FIG. 34 shows another reticle inspecting apparatus of the back illuminating unit, in which the respective positions of an illuminating unit 31 and a detection optical unit 40 with respect to the reticle 6 are reverse to those of the illuminating unit 3 and the detection optical system 4 of the reticle inspecting apparatus of FIG. 17. The reticle inspecting apparatus of FIG. 17 detects scattered light scattered by a foreign particle on the transparent substrate of the reticle 6, and the reticle inspecting apparatus of FIG. 34 detects scattered by a foreign particle and transmitted through the transparent substrate of the reticle 6. When the scattered light transmitted through the transparent substrate of the reticle 6 as in the reticle inspecting apparatus of FIG. 34, the resolution is deteriorated by aberration caused by the substrate of the reticle 6, which makes the stable detection of the foreign particle difficult. Therefore, the image forming optical system of the reticle inspecting apparatus of FIG. 34 needs to be provided with a lens capable of compensating the aberration caused by the substrate of the reticle 6.

Figure 35:
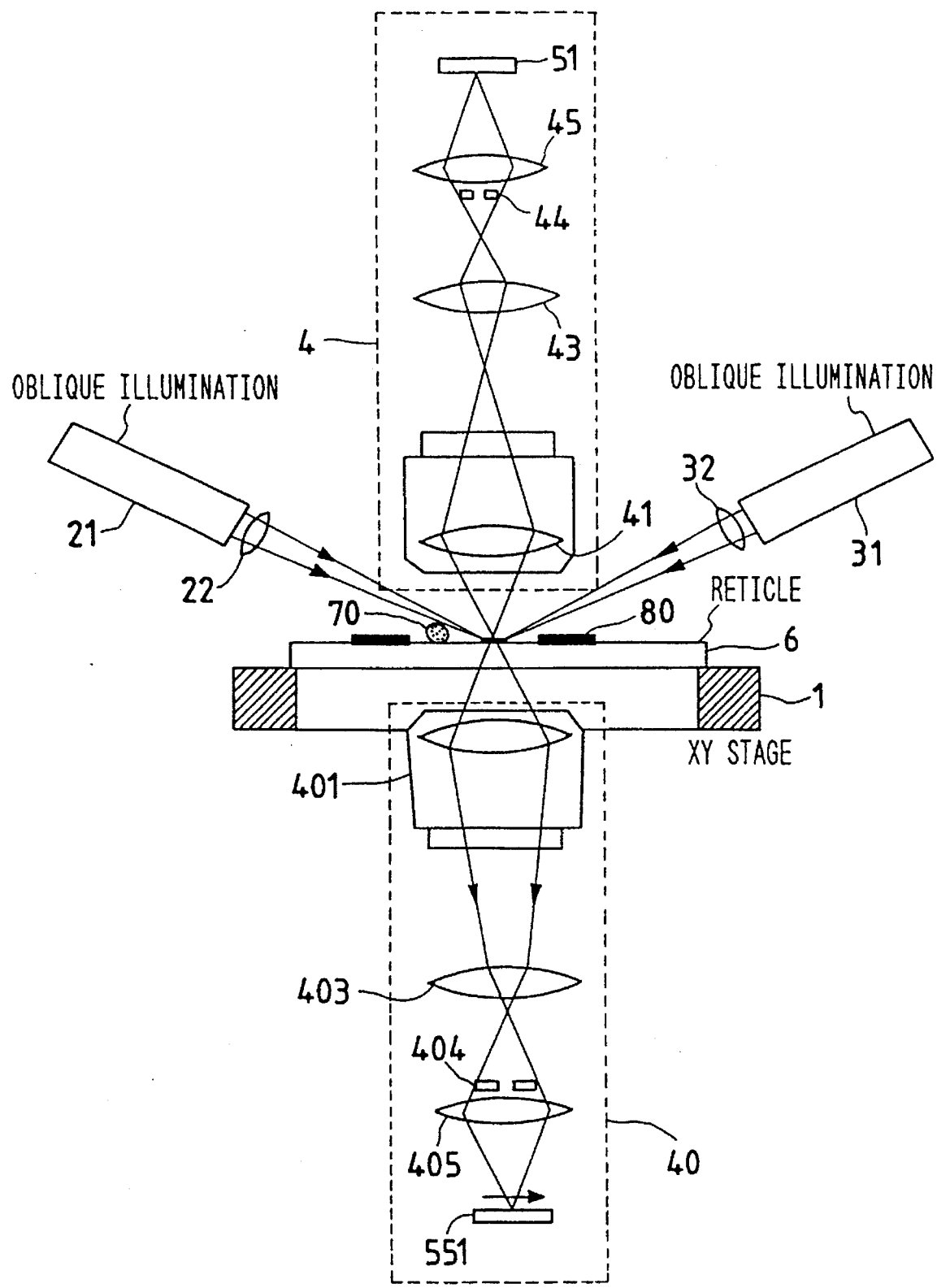
FIG. 35 is a diagrammatic view of a reticle inspective apparatus in a third embodiment according to the present invention.

A reticle inspecting apparatus shown in FIG. 35 analogous with the reticle inspecting apparatus shown in FIG. 34 in configuration. The reticle inspecting apparatus of FIG. 35 is suitable for inspecting the entire surface of the reticle 6. The reticle inspecting apparatus shown in FIG. 35 comprises a first front illuminating unit 21, a second front illuminating unit 31, which are disposed on the side of the front surface of the reticle 6, a front detection optical system 4 disposed on the side of the front surface of the reticle 6, and a back detection optical system 40 disposed on the side of the back surface of the reticle 6. The front detection optical system 4 detects scattered light scattered by opaque portions of the reticle 6, i.e., reflected light, and the back detection optical system 40 detects scattered by light-transmissive portions of the reticle 6, i.e., transmitted light. The front detection optical system 4 and the back detection optical system 40 must be provided respectively with appropriate wavelength filters to detect only reflected light and only transmitted light, respectively.

Foreign particles on the chromium pattern, i.e., the opaque film, of the reticle do not cause defects when an image of the reticle is printed by a photographic process. Foreign particles on exposed portions of the glass substrate cause defects in a photographically printed image of the reticle. Accordingly, foreign particles which may migrate from the chromium pattern to positions outside the chromium pattern, migratory foreign particles, must be detected.

Defects, such as foreign particles, on the chromium pattern must be detected in addition to the migratory foreign particles in the following cases.

In some cases, foreign particles on the chromium pattern cause problems when fabricating a phase shift reticle. Generally, when fabricating a phase shift reticle, a circuit pattern of a chromium film, i.e., a chromium pattern, is formed on the front surface of a substrate, a phase shift film is formed over the entire area of the front surface of the substrate by coating or sputtering, and then the phase shift film is etched to form a phase shift pattern. If there are foreign particles on the chromium pattern in forming the phase shift film, voids and breaks are formed in the phase shift film and, in some cases, the voids and breaks cause faulty printing. Therefore, the entire area of the substrate including the surface of the chromium pattern must be inspected before forming the phase shift film. The reticle inspecting method in accordance with the present invention is capable of detecting defects, such as voids and breaks, as well as foreign particles.

The entire surface of a transparent or translucent substrate not provided with a circuit pattern can be inspected by the reticle inspecting apparatus shown in FIG. 17 or 34. Since there is no circuit pattern and hence no diffracted light diffracted by a circuit pattern, the reticle inspecting apparatus need not be provided with the spatial filter 44. When the front scattered light is detected by this reticle inspecting apparatus, the magnitude of a detection signal provided upon the detection of a foreign particle is higher than that of a detection signal provided by a reticle inspecting apparatus of a reflection illumination system. If the spatial filter 44 is omitted, the stage may be moved for XY scanning or rotational scanning.

Figure 63:
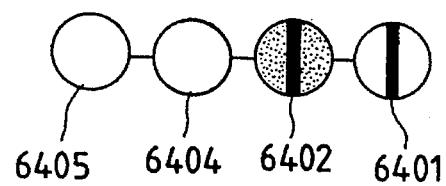
FIG. 63 is a plan view of spatial filters employed in the present invention.
Figure 64:
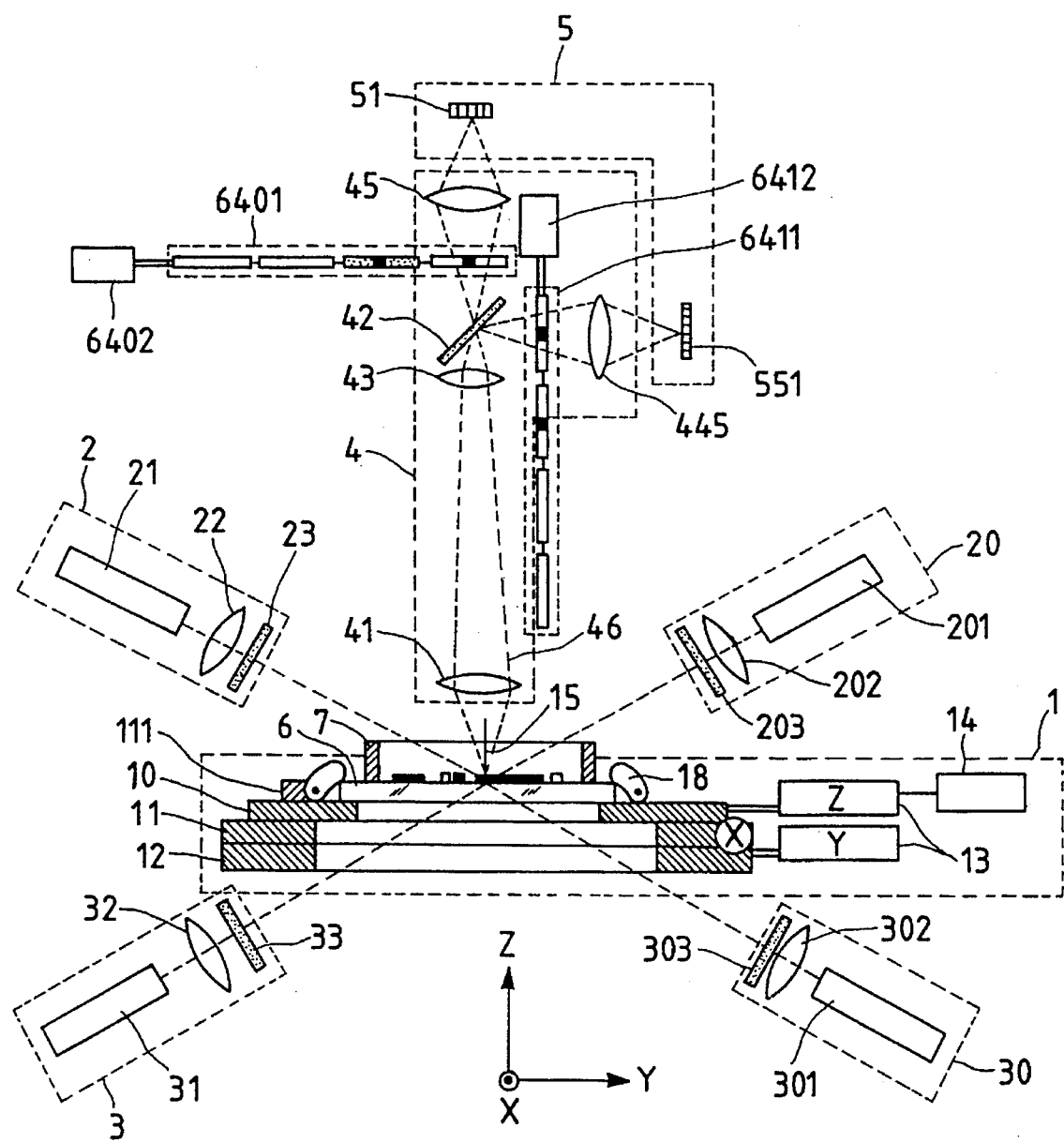
FIG. 64 is a schematic sectional view of assistance in explaining the condition of spatial filters in a reticle inspecting apparatus in accordance with the present invention.

Accordingly, it is desirable to provide the reticle inspecting apparatus with a mechanism capable of setting the spatial filter at the working position when necessary. The reticle inspecting apparatus may be provided with a spatial filter unit having a plurality of spatial filters capable of being selectively set at the working position one at a time. FIG. 63 shows a filter unit provided with a slot holding a linear spatial filter, a slot holding a combination of a linear spatial filter and a polarizing plate and two spare slots. A reticle inspecting apparatus shown in FIG. 64 is provided with filter units 6401 and 6411, which are similar to the filter unit of FIG. 63, and driving mechanisms 6402 and 6412 respectively for moving the filter units 6401 and 6411 to locate a selected spatial filter at a working position. In FIG. 64, a signal processing unit is omitted.

To inspect an object, such as a reticle, in which the circuit pattern forming condition and required sensitivity for detection change in each process, a reticle inspecting apparatus capable of changing sensitivity for detection for each process is used.

A signal processing system 5 as shown in FIG. 1, for example, comprises detectors 51 and 551, shading compensating circuits 113 and 123 for correcting the output signals of the detectors 51 and 551, four-pixel addition circuits 114 and 124, binarizing circuits 52, 53, 552 and 553, OR circuits 56 and 556, an AND circuit 57, block processing circuits 58 and 558, a microcomputer 54 and a display 55.

Each of the detectors 51 and 551 is, for example, a one-dimensional solid-state imaging device of a charge transfer type. When a defect, such as a foreign particle, is found in the inspection field 15 while the circuit pattern of the reticle 6 is scanned by moving the X-stage 10, the level of the light signal representing the circuit pattern, i.e., the intensity of the incoming light, increases and, consequently, the outputs of the detectors 51 and 551 increases. The one-dimensional solid-state imaging device is advantageous because the inspection field 15 can be expanded without reducing the resolution. The detectors 51 and 551 may be two-dimensional solid-state imaging devices or solid-state image sensors.

A binarizing threshold is set for the binarizing circuits 52 and 552. When the binarizing circuits 52 and 552 receive outputs of the detectors 51 and 551 exceeding a level corresponding to the intensity of reflected light corresponding to a size of a foreign particle to be detected, the binarizing circuits 52 and 552 provide logical "1". The outputs of the detectors 51 and 551 are provided together with the logic level, i.e., the result of binarization, to use the outputs for estimating the size and the like or to facilitate setting a threshold for binarization.

Shading compensating circuits 113 and 123 and 4-pixel addition circuits 114 and 124 will be described later. A blocking circuit 112 receives the output signals of the binarizing circuits 52 and 552 and prevents the double count of the two signals, which will be described later.

Upon the reception of a logical "1" from the blocking circuit 112, the microcomputer 54 decides that a defect is found, stores defect data including information about the respective positions of the X-stage 10 and the Y-stage 11, information about the position of the defect determined by calculation on the basis of the pixels, i.e., the solid-state image sensors, of the detectors 51 and 551 corresponding to the defect, and the values of the outputs of the detectors 51 and 551, and displays the defect data on the display 55. The microcomputer 54 controls the mechanisms of the reticle inspecting apparatus and serves also as an interface between the operator and the reticle inspecting apparatus.

Figure 62:
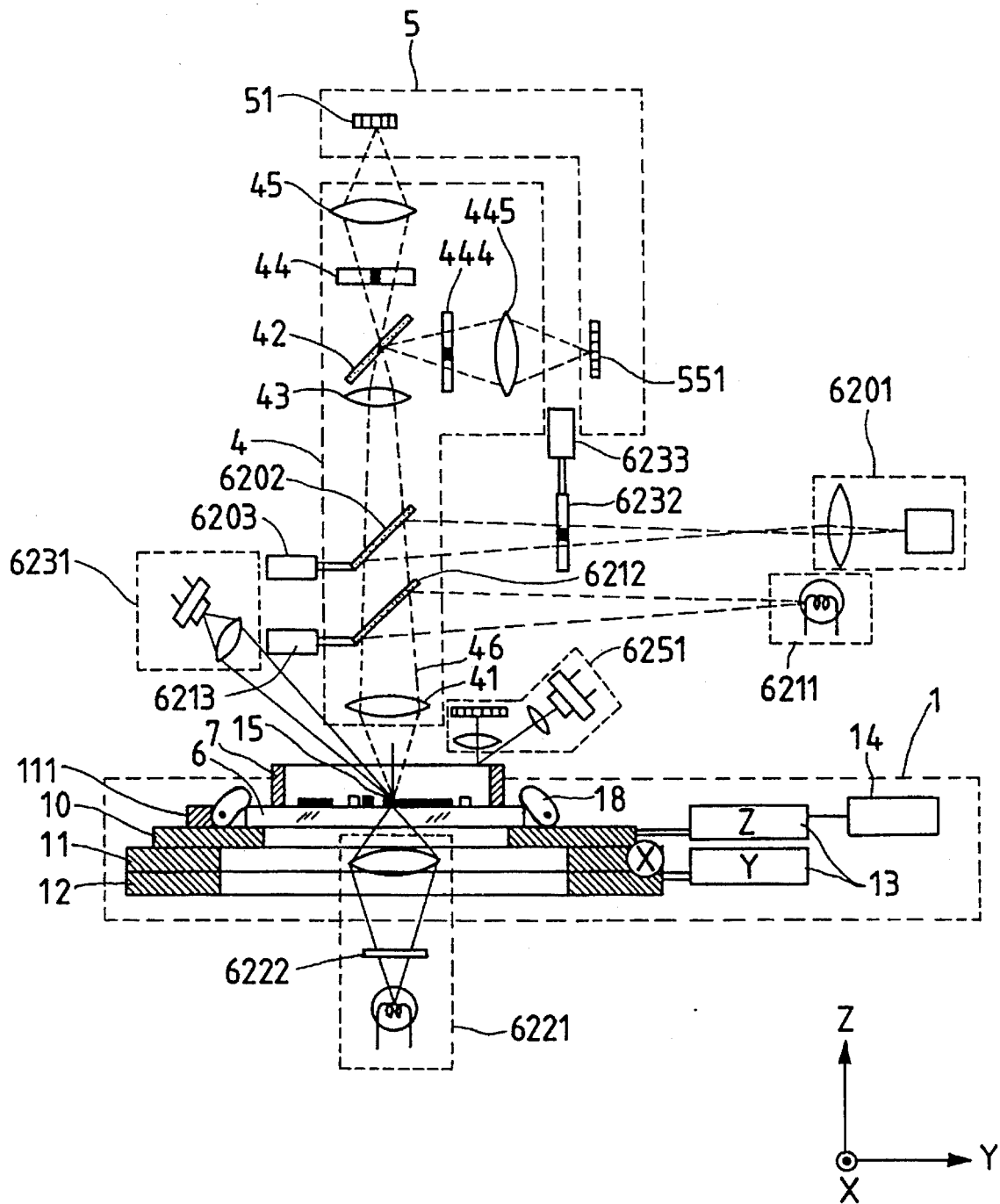
FIG. 62 is a schematic sectional view of an observation system in accordance with the present invention.

The results of inspection are displayed, and the position of the detected defect determined on the basis of the results of inspection are transferred to an observation unit to enable the operator to recognize the defect. Since the reticle, i.e., a photomask, is an original plate for fabricating LSI circuits, there must not be even a single defect, such as a foreign particle, that will adversely affect correct printing of an image of the circuit pattern of the reticle on a wafer by photographic processes on the reticle. Therefore, it is important to enable the operator to decide whether or not the detected defect, such as a foreign particle, affects the printing of an image of the circuit pattern on a wafer adversely. The results of inspection is transferred to the observation unit to enable the operator to examine the results of inspection. A reticle inspecting apparatus shown in FIG. 62 is provided with an observation unit. In this reticle inspecting apparatus, the optical path of a detection optical system is changed to give optical information for examination to the observation unit. When this reticle inspecting apparatus is used, any separate observation apparatus is not necessary, the reticle can accurately and efficiently be examined, and the contamination of the reticle during transportation can be obviated because the reticle need not be transported to a separate observation apparatus. In FIG. 62, a signal processing system and illuminating units for inspection are omitted. An observation illuminating system for observation comprises a transmission illuminating unit 6221 provided with a shutter 6222, a top illuminating unit 6211 having a half mirror 6212 and a driving mechanism 6213 for driving the half mirror 6212, and an oblique illuminating unit 6231 provided with a laser light source. The oblique illuminating unit 6231 may be omitted when the front illuminating units for inspection, i.e., the front illuminating units 2 and 20 in FIG. 1, project laser beams having wavelengths in those of visible radiation, and either the first front illuminating unit or the second front illuminating unit may be used for observation. These observation illuminating units are used selectively or in combination. Light reflected from a defect, such as a foreign particle, is concentrated by an objective lens 41 and is reflected by a reflecting mirror 6202 located at the working position by the driving mechanism 6202 to form an image by an observation device 6201, such as a TV camera, for observation. When necessary, a spatial filter 6232 is inserted in the optical path by a driving mechanism 6233 during observation.

Also shown in FIG. 62 is a pellicle inspecting unit 6251. Since sensitivity for the inspection of the pellicle and the back surface of the reticle not provided with the circuit pattern need not be as high as that for the inspection of the front surface of the reticle on which the circuit pattern is formed, the use of a low-sensitivity, simple, quick-operating inspection unit for the inspection of the reticle and the back surface of the reticle curtails the time necessary for inspection and simplifies the construction of the reticle inspecting apparatus. The reticle inspecting apparatus may be provided with a substrate inspecting unit having a simple configuration for inspecting a substrate having mirror-finished surfaces before forming a circuit pattern thereon, such as a glass plate or a glass substrate having only a surface coated with a metal thin film, because the surfaces not provided with any circuit pattern can be inspected for defects quickly in a high sensitivity by a substrate inspecting unit having a simple configuration.

Figure 5:
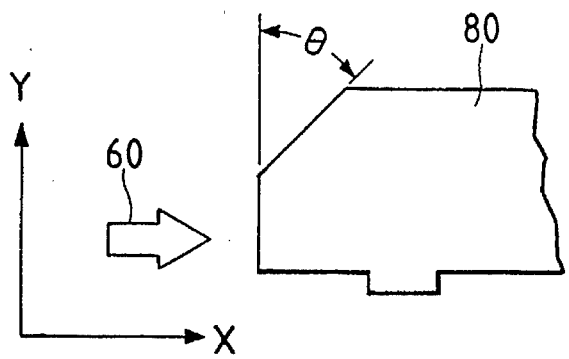
FIG. 5 is a plan view of assistance in explaining an angular circuit pattern.
Figure 6A:
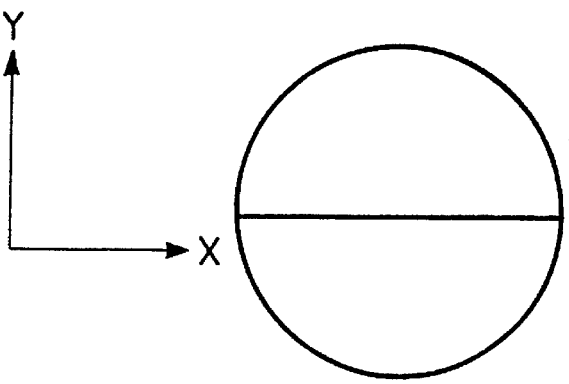
FIGS. 6(a), 6(b) and 6(c) are views showing the distribution of scattered light and that of diffracted light on a Fourier transform plane.
Figure 6B:
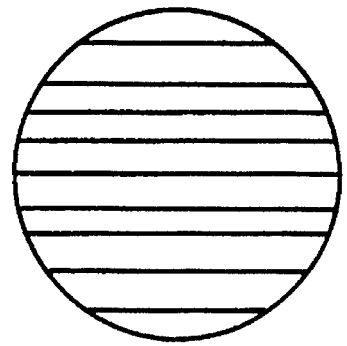
Figure 6C:
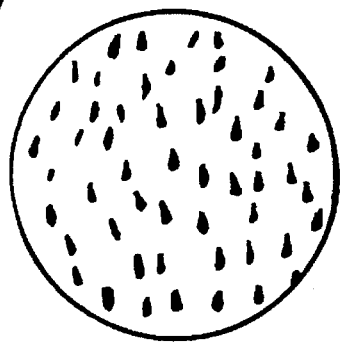
Figure 7A:
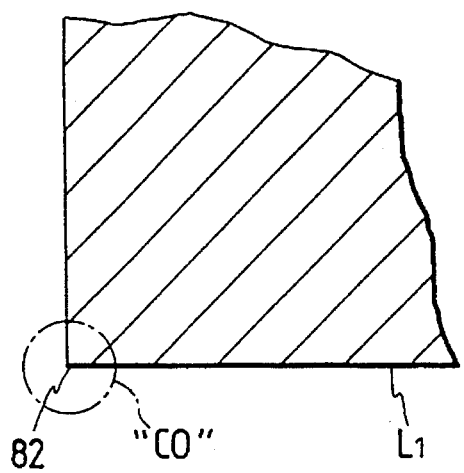
FIGS. 7(A) and 7(B) are a fragmentary plan view of a corner of a circuit pattern and an enlarged view of a portion CO of FIG. 7(A), respectively.
Figure 7B:
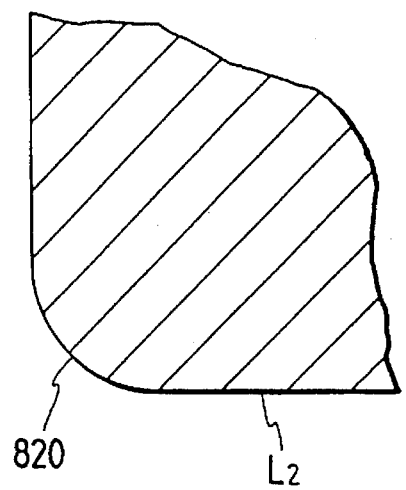
Figure 8:
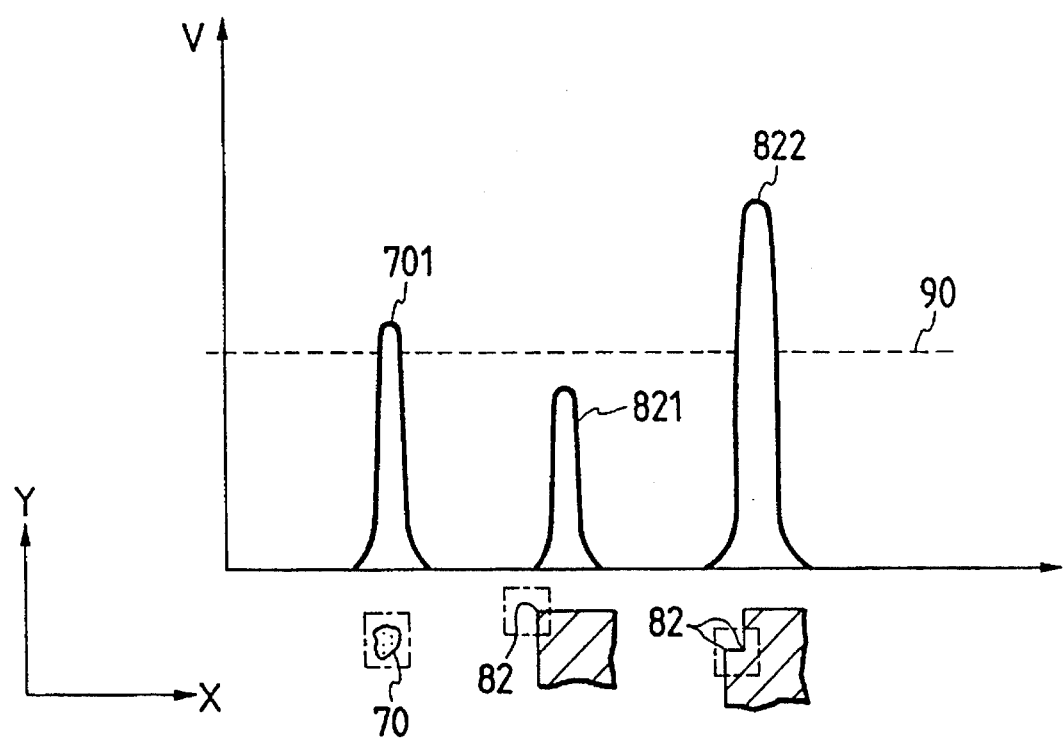
FIG. 8 is a graph of assistance in explaining the relation between a scattered light detection signal provided when scattered light scattered by a foreign particle is detected and a detection signal provided when a circuit pattern is detected.
Figure 9:
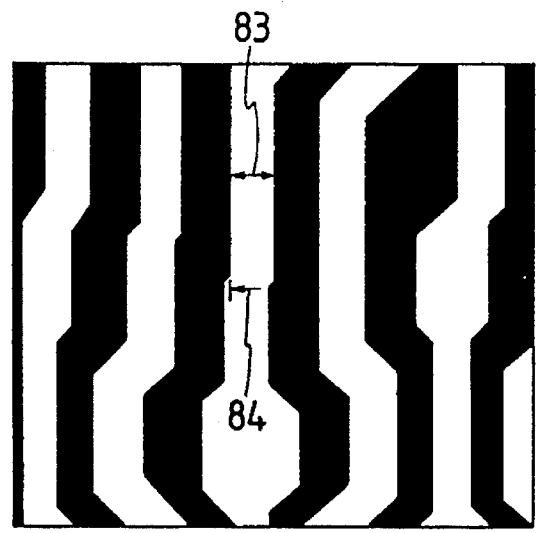
FIG. 9 is a plan view of a minute circuit pattern to be inspected for defects by the reticle inspecting apparatus of the present invention.
Figure 10:
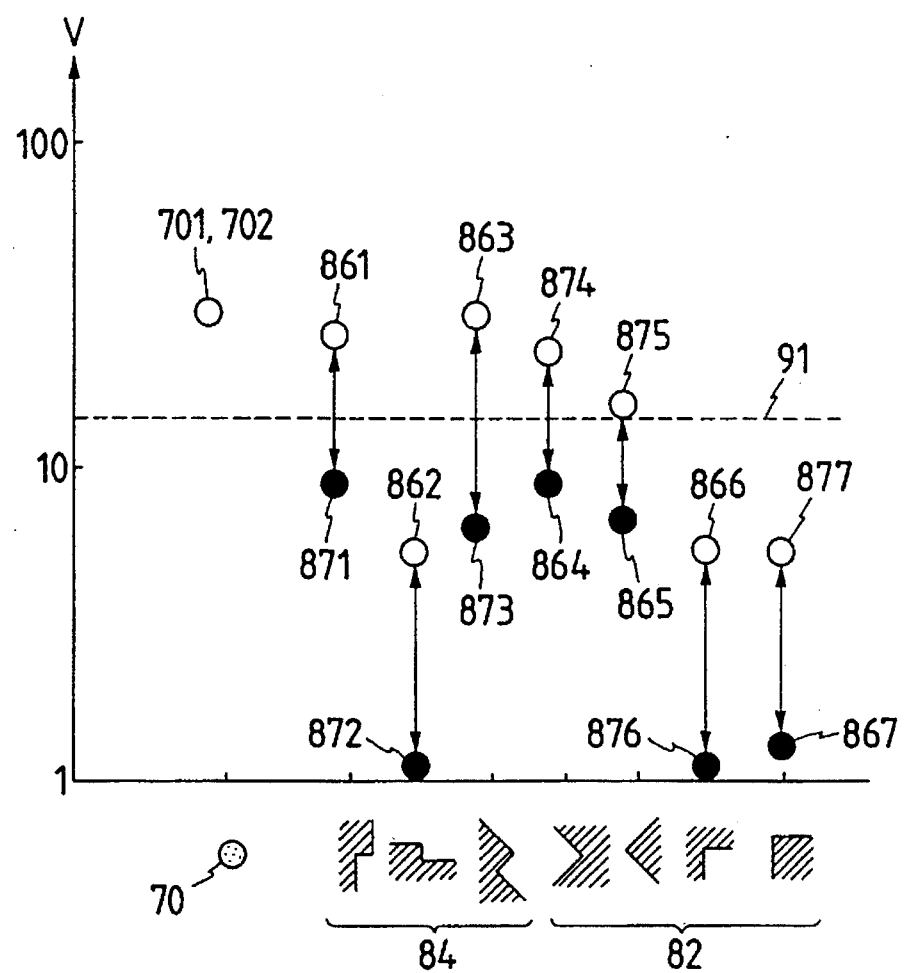
FIG. 10 is a graph showing the levels of detection signals provided when a foreign particle and corners of a circuit pattern are detected.

The operation of the reticle inspecting apparatus will be described with reference to FIGS. 4 to 10, in which parts like or corresponding to those shown in FIG. 1 are denoted by the same reference characters. FIG. 2 is a view of assistance in explaining a reticle scanning method, FIG. 5 is a plan view of assistance in explaining an angular portion of the circuit pattern, FIGS. 6(a)–(c) are views showing the distribution of scattered light and that of diffracted light on the Fourier transform plane, FIG. 7(A) is a fragmentary plan view of a corner of a circuit pattern and FIG. 7(B) is an enlarged view of a portion CO of FIG. 7(A), FIG. 8 is a graph of assistance in explaining the relation between a scattered light detection signal provided when scattered light scattered by a foreign particle is detected and a detection signal provided when a circuit pattern is detected, FIG. 9 is a plan view of a minute circuit pattern, and FIG. 10 is a graph showing the levels of detection signals provided when a foreign particle and corners of the circuit pattern are detected.

Figure 11:
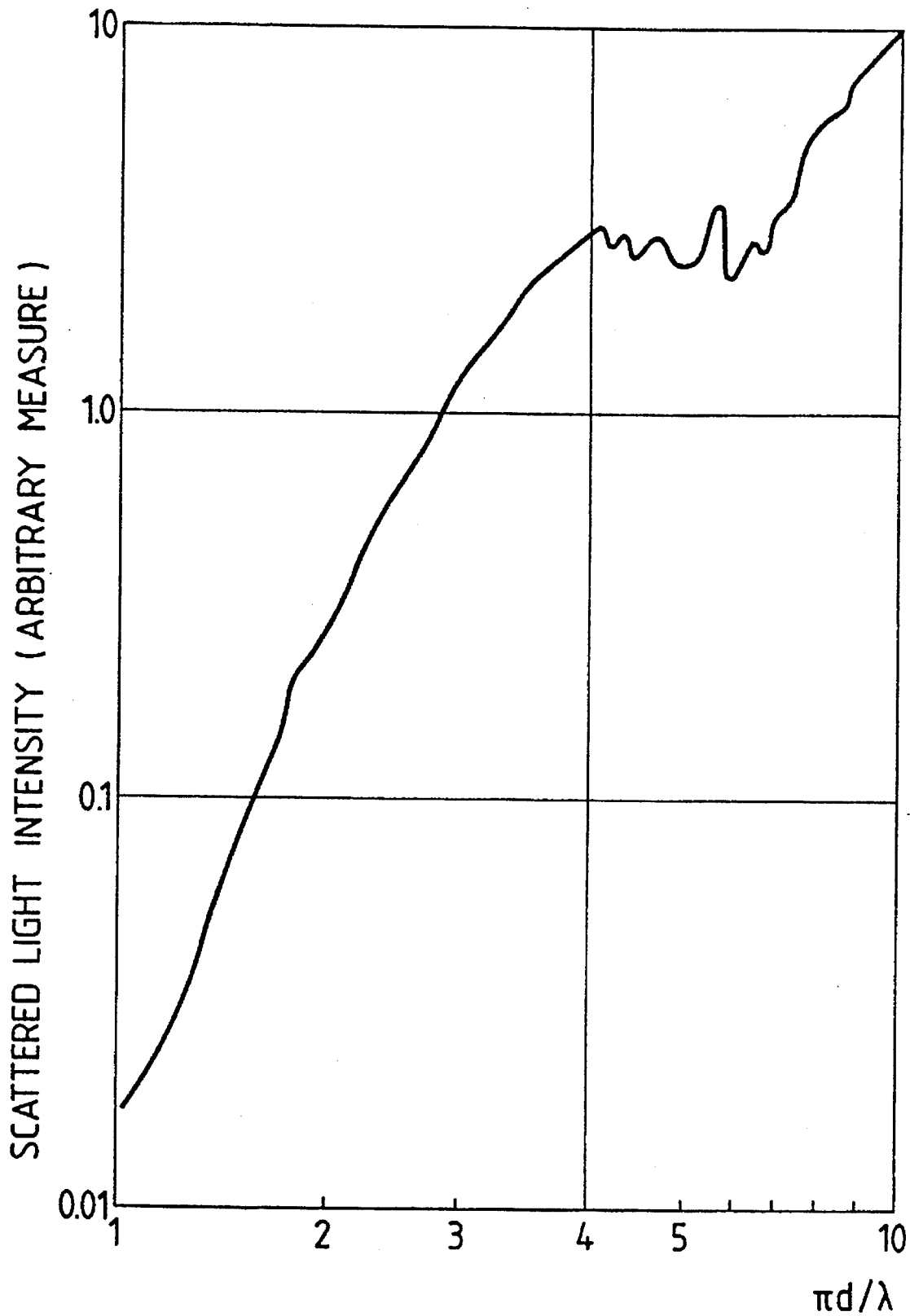
FIG. 11 is a graph showing the relation between the theoretical intensity of scattered light scattered by particles and a nondimensional value $\pi d/\lambda$, where d is the size of the particle and $\lambda$ is the wavelength of the illuminating light beam.
Figure 13:
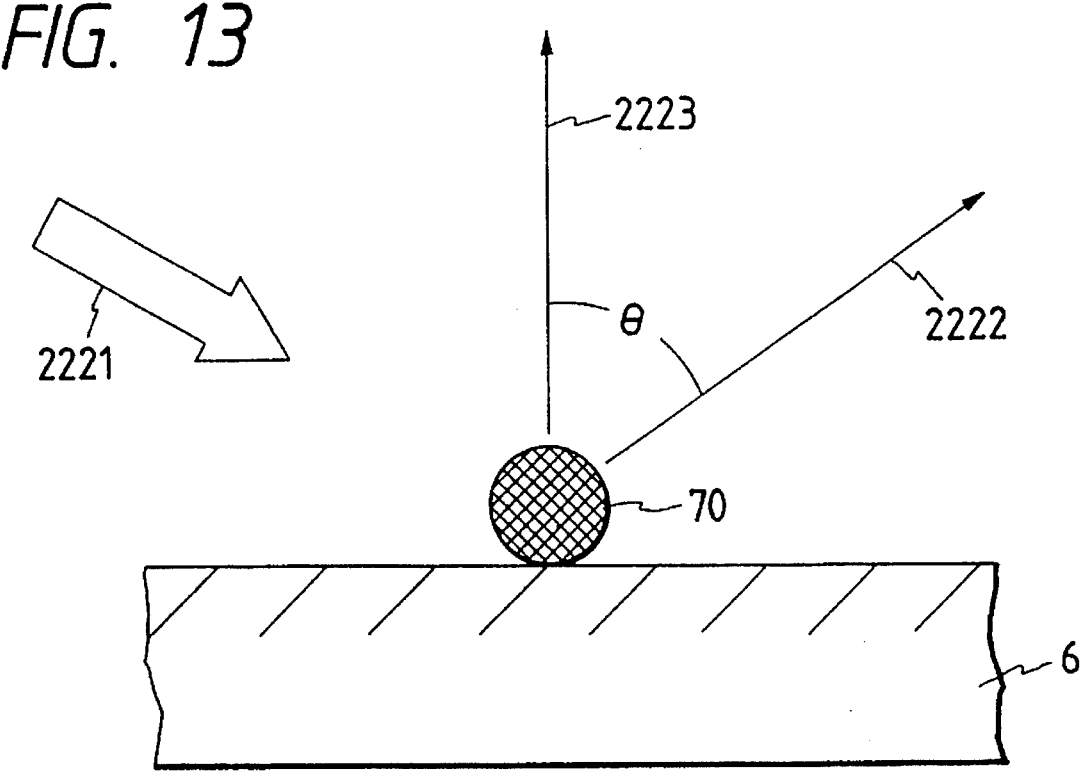
FIG. 13 is a diagrammatic view showing the direction of travel of diffracted light diffracted by a foreign particle.
Figure 14:
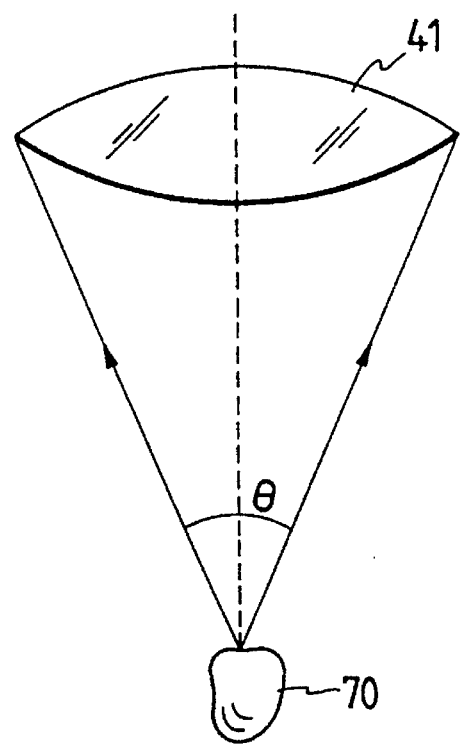
FIG. 14 is a diagrammatic view of assistance in explaining the definition of the NA of an optical system in accordance with the present invention.
Figure 15:
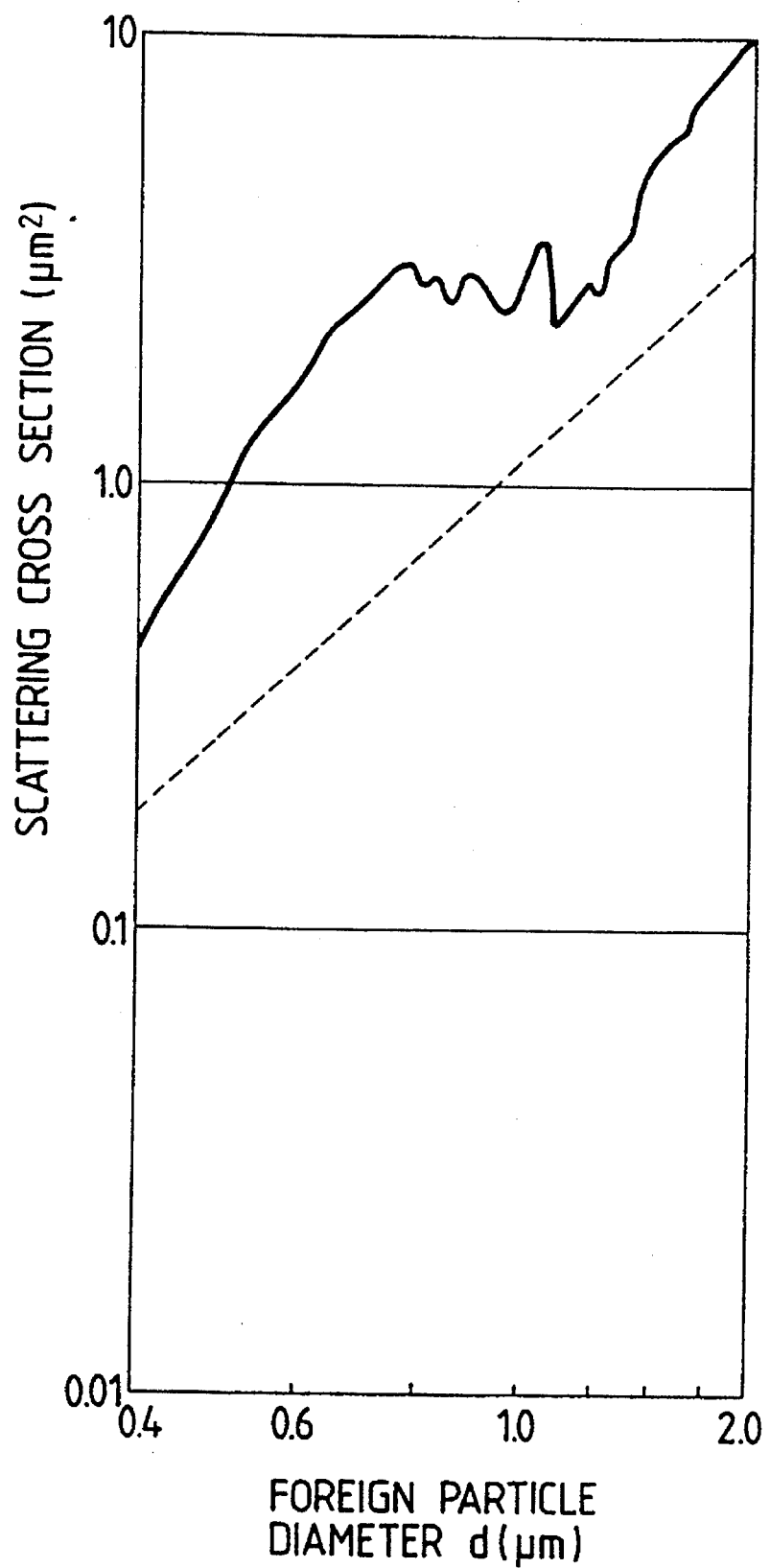
FIG. 15 is a graph showing the relation between the sectional area of scattered light proportional to the intensity of the scattered light scattered by a foreign particle and the diameter d of the foreign particle.

FIG. 11 is a graph showing the relation between the theoretical intensity of scatted light scattered by particles and a non-dimensional value $\phi d/\lambda$, where d is the size of the particle and $\lambda$ is the wavelength of the illuminating light beam. FIGS. 12(A) and 12(B) are vies of assistance in explaining a method of detecting scatted light from a foreign particle by using an optical system having a high NA in accordance with the present invention. FIG. 13 is a diagrammatic view showing the direction of travel of diffracted light 2222 and 2223 from illumination of light 2221 applied to the defect 70 such as a foreign particle on the reticle 6. FIG. 14 is a diagrammatic view of assistance in explaining the definition of the NA of the optical system utilizing an objective lens 41. FIG. 15 is a graph showing the relation between the sectional area of the scattered light proportional to the intensity of the scattered light scattered by foreign particle and the diameter d of the foreign particle.

Shown in FIG. 4(A) are a foreign particle 70 on the reticle 6 fastened to the Z-stage 10 by the fastening device 18, a straight portion 81 of a circuit pattern 80, and a corner 82 of the circuit pattern 80.

The reticle 6 is illuminated obliquely by the illuminating unit 2 (or any one of the illuminating units 20, 3 and 30). Directly reflected light and directly transmitted light are not gathered. Only scattered light and diffracted light are gathered by the objective lens 41. Only the diffracted light diffracted by an edge of the circuit pattern 80 extending at an angle $\theta=0°$ to a direction perpendicular to the horizontal component 60 of the direction of travel of the illuminating light emitted by the illuminating unit 2 (or any one of the illuminating units 20, 3 and 30), which is called a 0-degree edge, is focused in a band as shown in FIG. 6(a) on the Fourier transform plane of the objective lens 41. The angle $\theta$ of the edges of the circuit pattern 80 is 0°, 45° or 90°. Diffracted light (b) diffracted by a 45-degree edge and diffracted light (c) diffracted by a 90-degree edge do not fall on the objective lens 41 as shown in FIG. 4(A) and do not affect the inspection of the reticle. Scattered light scattered by the foreign matter 70 is scattered over the entire area of the Fourier transform plane as shown in FIG. 6(c). Therefore, the foreign matter 70 can be discriminated from the circuit pattern 80 by intercepting the diffracted light (a) diffracted by the 0-degree pattern shown in FIG. 4(A) by the spatial filters 44 and 44 disposed on the Fourier transform planes and each having a band-shaped screening portion and light-transmissive portions on the opposite sides of the opaque portion.

Since Fourier transform planes exist behind the objective lens 41 and on the plane of the entrance pupil of the objective lens 41 as shown in FIG. 4(A), the spatial filter may be disposed immediately before the objective lens. In this arrangement, aberration attributable to the different wavelengths of the component of the inspecting light beam does not occur because the inspecting light beam is not transmitted by the lens system and hence Fourier transform planes for all the wavelength coincide.

The defect is not detected directly on the Fourier transform plane because the defect can be detected in a high sensitivity when the defect is detected on an image plane determined through the inverse Fourier transformation of a Fourier transform image in a reduced inspection field. However, since inverse Fourier transformation is a mathematical operation, the detection may be made by directly determining the amplitude and the phase difference of a Fourier transform image on the Fourier transform plane and executing an inverse Fourier operation by a computer, which increases the degree of freedom of space filtering.

Thus, this detection optical system 4 has a large NA. When NA=0.5, the aperture area of the detection optical system 4 is about twenty times the aperture area of the conventional detection optical system having a small NA (NA=0.1). Scattered light scattered by a corner portion (FIG. 4(D)) of the circuit pattern 80 cannot completely be intercepted by the linear spatial filter. Therefore, when 10×20 $\mu m^2$ detecting pixels are used for detection (FIG. 4(B)), scattered light scattered by a plurality of corner portions fall on the pixels and the detection of only the foreign particle is impossible.

Accordingly, the present invention uses 2×2 $\mu m^2$ pixels for higher resolution (FIG. 4(C)) to eliminate the influence of the scattered light and diffracted light scattered and diffracted, respectively, by the circuit pattern 80 as perfectly as possible. The size of the pixels need not necessarily 2×2 $\mu m^2$. The pixels may be of any size, provided that the size is smaller than the size L of the smallest portion of the circuit pattern 80. When the reticle is exposed by a stepper having a reduction ratio of 1/5 when fabricating a 0.8 $\mu m$ process LSI, pixels of 0.8×5=4 $\mu m^2$ or below serve the purpose, and pixels of 0.5×5=2.5 $\mu m^2$ or below serve the purpose when fabricating a 0.5 $\mu m$ process LSI.

Practically, the size of the pixels may be greater or smaller than the above-mentioned sizes as long as the pixels are able to reduce the influence of the scattered light scattered by the corner portions of the circuit pattern to the negligibly small extent. Concretely, a desirable size of the pixels is nearly equal to the size of the smallest portion of the circuit pattern. When the size of the pixels is on the order of the size of the smallest portion of the circuit pattern, only less than two corner portions correspond to each pixel, and as is obvious from the results of experiment shown in FIG. 10, the size of the pixels is small enough. Pixels having a size in the range of 1 to 2 $\mu m^2$ are desirable for inspecting a reticle for fabricating a 64M DRAM.

Since a corner 82 of the circuit pattern 80 shown in FIG. 7(A) has a continuously curved edge 820 as shown in FIG.

7(B), diffracted light (d) diffracted by the corner 82 is scattered on the Fourier transform planes as shown in FIG. 6(*b*) and the spatial filters 44 and 444 are unable to intercept the diffracted light (d) completely. Consequently, the output V of the detector 51 (551) increases as shown in FIG. 8 and the foreign matter 70 cannot be discriminated from the circuit pattern 80 if diffracted light diffracted by a plurality of corners 82 falls on the detector 51 (551). As shown in FIG. 8, the output 822 of the detector 51 (551) provided when a plurality of corners 82 are detected is higher than the output 821 of the same provided when a single corner 82 is detected. If the output of the detector 51 (551) is binarized by using a binarizing threshold 90 indicated by a dotted line, the output 701 of the detector 51 (551) representing the foreign particle 70 cannot be discriminated from the output 822 of the detector 51 (551) representing the plurality of corners 82.

To solve the problem described with reference to FIG. 8, the present invention forms an image of the inspection field 15 on the detectors 51 and 551 by means of the objective lens 41 and the focusing lenses 45, determines the sizes of the detectors 51 and 551 and image forming magnification selectively to determine the size of the inspection field 15 (for example, 2 μm×2 μm) optionally in order to obviate the simultaneous incidence of diffracted light diffracted by a plurality of corners 82 on the detectors 51 and 551. However, this arrangement is not sufficiently effective to discriminate a foreign particle of a size on the submicron order from a corner 82 of the circuit pattern 80. Furthermore, since the behavior of diffracted light diffracted by a portion of a size 84 on the submicron order, which is smaller than the size 83 of other portions of the circuit pattern 80 as shown in FIG. 9, is similar to that of scattered light scattered by the foreign particle 70, it is difficult to discriminate the foreign particle 70 from such a minute circuit pattern.

The reticle inspecting apparatus of the present invention is capable of detecting the foreign particle 70 in such a minute circuit pattern having portions of a size 84 on the submicron order. In FIG. 10, 701 and 702 indicate a detection signal provided upon the detection of scattered light scattered by a minute foreign particle 70 of a size on the submicron order, 864, 874, 865, 875, 866, 876, 867 and 877 indicate detection signals provided upon the detection of scattered light scattered by all the corners 82 of the 0-degree, 45-degree and 90-degree edges, and 861, 871, 862, 872, 863 and 873 indicate detection signals provided upon the detection of scattered light scattered by minute portions of sizes 84 on the submicron order. The detection signals 701, 861, 862, 863, 864, 865, 866 and 867 are provided by the detector when the illuminating light beam projected by the first front illuminating unit 2 (or the first back illuminating unit 3) and scattered by the minute circuit pattern is detected, and the detection signals 702, 871, 872, 873, 874, 875, 876 and 877 are provided by the detector when the illuminating light beam projected by the second front illuminating unit 20 (or the second back illuminating unit 30) and scattered by the minute circuit patter is detected. For example, the detection signals 861←→871 are those provided when the illuminating light beam projected by the first front illuminating unit 2 (or the first back illuminating unit 3) and scattered by a portion of the minute circuit pattern is detected by the detector and when the illuminating light beam projected by the second front illuminating unit 20 (or the second back illuminating unit 30) and scattered by the same portion of the minute circuit pattern is detected by the detector, respectively. As is obvious from FIG. 10, the value of the detection signal provided upon the detection of the foreign particle 70 is less dependent on the direction of projection of the illuminating light beam than that of the detection signal provided upon the detection of a portion of the minute circuit pattern. In FIG. 10, a dotted line 91 represents the threshold for binarization.

As is obvious from FIG. 10, the value of the detection signal provided by the detector upon the detection of a portion of the minute circuit pattern is greatly dependent on the direction of projection of the illuminating light beam and, when a portion of the surface of the reticle 6 is illuminated obliquely by two illuminating light beams which travel respectively along paths which are symmetrical with respect to a normal to the surface of the reticle 6 at the illuminated portion, either of the detection signals provided upon the detection of the two illuminating light beams scattered by the illuminated portion is necessarily smaller than the detection signal provided upon the detection of the scattered light scattered by the foreign particle of a size on the submicron order as indicated by solid circles. When the illuminating light beams are projected obliquely by both the first front illuminating unit 2 and the second front illuminating unit 20 which are disposed symmetrically with respect to a normal to the surface of the reticle 6 at the illuminated position or by both the first back illuminating unit 3 and the second back illuminating unit 30 which are disposed symmetrically with respect to a normal to the surface of the reticle 6 at the illuminated position, the detection signal is the sum of the detection signal provided upon the detection of the scattered illuminating beam projected by one of the two front (back) illuminating units and scattered by the foreign particle or a portion of the circuit pattern and the detection signal provided upon the detection of the scattered illuminating beam projected by the other front (back) illuminating unit and scattered by the same foreign particle or the same portion of the circuit pattern. Thus, the foreign particle can be illuminated in an illuminance higher than an illuminance in which the circuit pattern is illuminated, whereby the foreign particle 70 of a size on the submicron order can be discriminated from the circuit pattern 80.

When the scattered light scattered by the foreign particle 70 is detected, the microcomputer 54 stores foreign particle data including information about the respective positions of the X-stage 10 and the Y-stage 11, information about the position of the foreign particle 70 calculated on the basis of the position of the corresponding pixel, and the detection signals of the detectors 51 and 551 in a storage device and displays the foreign particle data on the display 55, such as a CRT.

As explained above with reference to FIG. 10, the value of the detection signal provided by the detector upon the detection of a portion of the circuit is greatly dependent on the direction of projection of the illuminating light beam and, when a portion of the surface of the reticle 6 is illuminated obliquely by two illuminating light beams which travel respectively in opposite directions, either of the detection signals provided upon the detection of the two illuminating light beams scattered by the illuminated position is always smaller than the detection signal provided upon the detection of a defect, such as a foreign particle as indicated by solid circles in FIG. 10.

Accordingly, when the surface of the reticle 6 is illuminated obliquely by two illuminating light beams traveling respectively in two opposite directions, each of the detection signals provided upon the detection of a foreign particle and the circuit pattern is merely the sum of the detection signals and it is difficult to binarize the detection signal by the threshold. However, when the scattered opposite illuminating light beams are detected by two separate detectors and the respective output signals of the two detectors are binarized by the threshold 91, both the outputs of the binarizing circuit are "1" when the illuminating light beams scattered by a foreign particle are detected, and both the outputs of the binarizing circuits are "0" or one of the outputs of the same is "1" when the illuminating light beams scattered by the circuit patter are detected. Thus, the foreign particle 70 of a size on the submicron order can be discriminated from the circuit pattern by determining the logical product of the outputs of the binarizing circuits through logic operation.

The scattered illuminating light beams projected respectively along opposite directions must be detected separately for the detection of a foreign particle by means of the AND circuit. The front illuminating units 2 and 20 are provided respectively with light sources capable of emitting illuminating light beams differing from each other in wavelength, respectively, to enable wavelength separation (color separation) or of emitting illuminating light beams differing from each other in polarization characteristic, respectively, to enable polarization separation for the discrimination of a foreign particle from the circuit pattern by using the AND circuit. Since the illuminating light beams are intercepted by the frame holding the pellicle, the entire front surface of the reticle cannot be illuminated with illuminating light beams traveling respectively in opposite directions by the front illuminating units 2 and 20; that is, the areas 3724 and 3704 in FIG. 37 cannot be illuminated with illuminating light beams traveling respectively in opposite directions. The present invention utilizes the following facts: (1) a high sensitivity for detection is necessary for the detection of foreign particles in light-transmissive areas, i.e., exposed portions of the surface of the glass substrate, in the surface of the reticle because the output signal of the detector representing the intensity of scattered light scattered by a foreign particle in a light-transmissive area is low, and the calculation of logical product is not necessary for the detection of a foreign particle on the opaque, metal thin film, such as a chromium film, because the output signal of the detector representing the intensity of scattered light scattered by a foreign particle on the opaque, metal thin film is high; (2) the light sources of the front illuminating units and those of the back illuminating units are different in wavelength from each other; and (3) the entire surface of the reticle can be illuminated without being obstructed by the frame holding the pellicle by using the front illuminating unit and the back illuminating unit, which will be described later.

The present invention illuminates a reticle to detect a foreign particle in a light-transmissive area on the reticle by the first front illuminating unit 2 and the second back illuminating unit 30 or by the second front illuminating unit 20 and the first back illuminating unit 3, separates the scattered light beams by wavelength separation, and binarizes the output signals of the detectors.

FIGS. 71(A)–71(C) and 72(A)–72(C) are sectional views of assistance in explaining the effect. Shown in FIGS. 71(A)–71(C) and 72(A)–72(C) are a glass substrate 6901, a front illuminating light beam 6904 having a wavelength λ1 for obliquely illuminating the circuit pattern formed on the front surface of the glass substrate 6901, a back illuminating light beam 6905 having a wavelength λ2 and traveling in a direction opposite the direction in which the front illuminating light beam 6904 travels, for illuminating the circuit pattern from the side of the back surface of the glass substrate 6901, edges 6902 and 7002 of the circuit pattern, scattered front illuminating light 6942, which is part of the front illuminating light beam 6904 scattered by the edge 6902 of the circuit pattern, scattered back illuminating light 6952, which is part of the back illuminating light beam 6905 scattered by the edge 6902 of the circuit pattern, scattered front illuminating light 7042, which is part of the front illuminating light beam 6904 scattered by the edge 7002 of the circuit pattern, scattered back illuminating light 7052, which is part of the back illuminating light beam 6905 scattered by the edge 7002 of the circuit pattern, standard particles 6903 and 7003 of a size on the order of 0.3 μm, i.e., typical models of foreign particles, scattered front illuminating light 6943, which is part of the front illuminating light beam 6904 scattered by the standard particle 6903, scattered back illuminating light 6953, which is part of the back illuminating light beam 6905 scattered by the standard particle 6903, scattered front illuminating light 7043, which is part of the front illuminating light beam 6904 scattered by the standard particle 7003, and scattered back illuminating light 7053, which is part of the back illuminating light beam 6905 scattered by the standard particle 7003.

The intensity of the scattered light is greatly dependent on the incidence angle of the illuminating light beam on the circuit pattern when the illuminating light beam is projected obliquely on the circuit pattern having a thickness, which is very small though. For example, in FIG. 71, the intensity of the scattered back illuminating light is comparatively high and the intensity of the scattered front illuminating light is comparatively low. The intensities of the scattered front illuminating light and the scattered back illuminating light scattered by a minute foreign particle not having distinct anisotropy are not very different from each other.

As shown in graphs of FIG. 71 showing detection signals (V) corresponding to the intensities of the different kinds of scattered illuminating light, the intensity of the scattered back illuminating light 6952 scattered by the edge of the circuit pattern is higher than that of the scattered back illuminating light 6953 scattered by the standard particle 6903. If a threshold Th2 for simple binarization is used, a foreign particle cannot be discriminated from the edge of the circuit pattern. However, the intensity of the scattered front illuminating light 6943 scattered by the standard particle is higher than that of the scattered front illuminating light 6942 scattered by the edge of the circuit pattern and hence a foreign particle can be discriminated from the edge of the circuit pattern by using the threshold Th1 for simple binarization. When the circuit pattern has the edge 6902 as shown in FIG. 71, the scattered front illuminating light 6942, i.e., part of the front illuminating light beam 6904 scattered by the edge 6902, may be detected. FIG. 72 shows the edge 7002 facing in a direction different from that in which the edge 6902 faces relative to the direction of the front illuminating light beam 6904.

As shown in FIG. 72, the intensity of the scattered front illuminating light 7042, i.e., part of the front illuminating light beam 6904 scattered by the edge 7002, is comparatively high and the intensity of the scattered back illuminating light 7052, i.e., part of the back illuminating light beam 6905 scattered by the edge 7002, is comparatively low, and the difference between the intensities of the scattered front illuminating light 7043 and the scattered back illuminating light 7053 scattered by a minute particle not having distinct anisotropy is not very large.

As shown in FIG. 72, the intensity of the scattered front illuminating light 7042 scattered by the edge 7002 is higher than that of the scattered front illuminating light 7043 scattered by the standard particle. Therefore, if the threshold Th1 for simple binarization is used, a foreign particle cannot be discriminated from the edge. On the other hand, the intensity of the scattered back illuminating light beam 7053 scattered by the standard particle is higher than that of the scattered back illuminating light 7052 scattered by the edge 7002 of the circuit pattern, and a foreign particle can be discriminated from the edge of the circuit pattern by using the threshold Th2 for simple binarization. When edges of the circuit pattern face in the same direction as that in which the edge 7002 shown in FIG. 72 faces, foreign particles can be discriminated from the edges by detecting the scattered back illuminating light, i.e., part of the back illuminating light beam 6905. However, an actual circuit pattern has both edges like the edge 6902 shown in FIG. 71 and edges like the edge 7002 shown in FIG. 2, and hence it is ineffective to detect either the scattered front illuminating light or the scattered back illuminating light selectively. When the reticle is inspected by a reticle inspecting method in accordance with the present invention, the intensities of the scattered front illuminating light, i.e., part of the front illuminating light beam 6904 and the scattered back illuminating light, i.e., part of the back illuminating light beam 6905 are higher than both the threshold Th1 and Th2 for binarization, and the intensities of both the scattered front illuminating light beam and the scattered back illuminating light scattered by the edges (FIGS. 71 and 72) are always lower than both the threshold Th1 and Th2 for binarization. Therefore, only the scattered light scattered by foreign particles can be detected by detecting the intensities of the scattered front illuminating light, i.e., part of the front illuminating light beam 6904, and the back illuminating light, i.e., part of the back illuminating light beam 6905, binarizing the intensities by using the threshold Th1 and Th2 for binarization, and carrying out an AND operation between the binarized intensities.

The scattered front illuminating light and the scattered back illuminating light can easily be separated with a color separation filter or the like and the front illuminating light beam 6904 and the back illuminating light beam 6905 can be used simultaneously, when the respective wavelengths of the front illuminating light beam 6904 and the back illuminating light beam 6905 are different from each other, which enables real-time reticle inspection.

Figure 40:
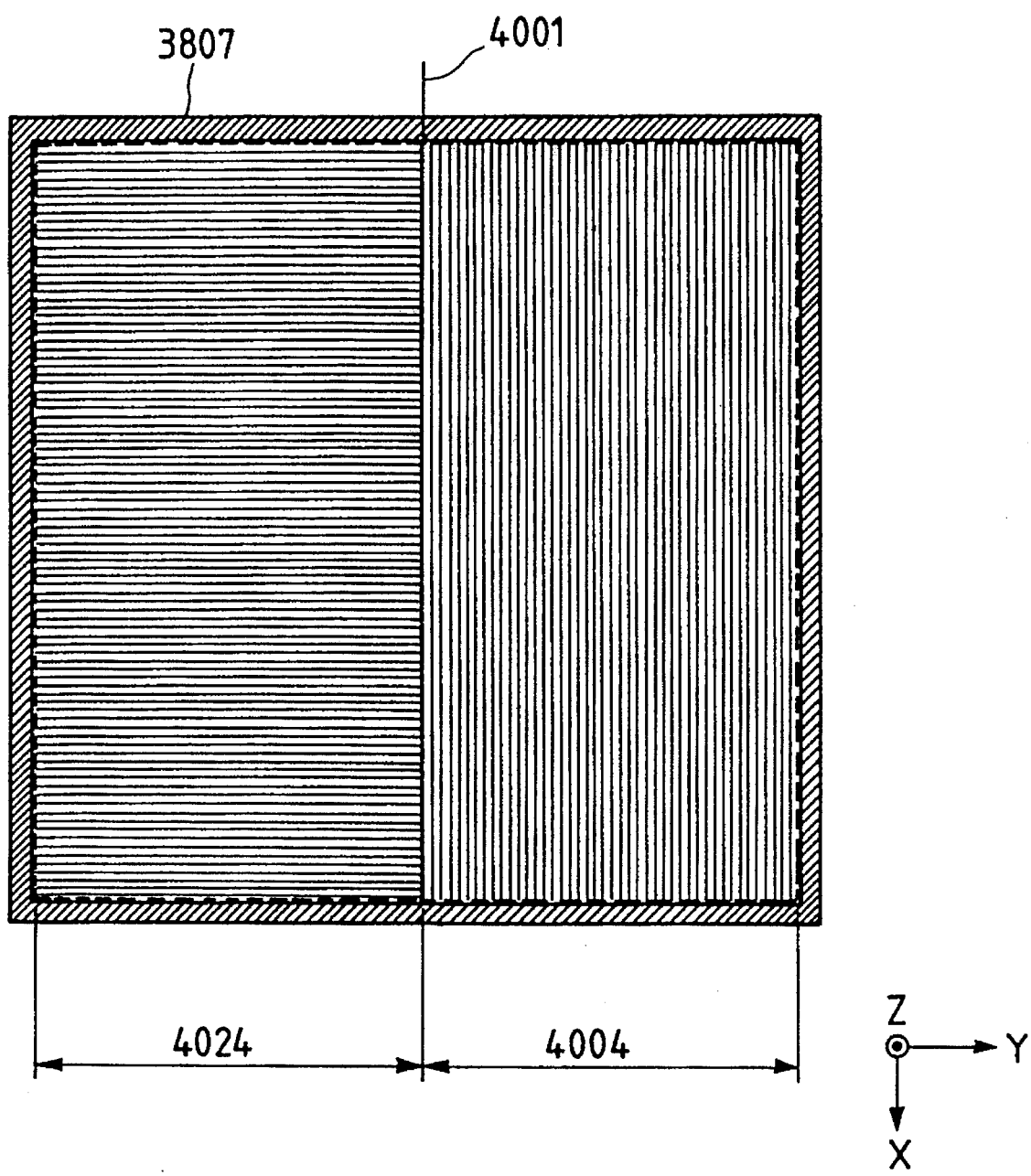
FIG. 40 is a plan view of assistance in explaining the change of illuminating units in accordance with the present invention.

FIGS. 39(A) and 39(B), similarly to FIGS. 38(A) to 38(C), shows the positional relation between the reticle 6, the pellicle 7, the oblique illuminating light beam 3802 projected by the first front illuminating unit 2, the oblique illuminating light beam 3820 projected by the second illuminating unit 20, the oblique illuminating light beam 3803 projected by the first back illuminating unit 3, the oblique illuminating light beam 3830 projected by the second back illuminating unit 30 (FIG. 1) and the inspection field 15, i.e., the illuminated position. FIG. 39(A) shows a first illuminating mode for inspecting an area 4024 on the left side of the center line 4001 of the frame holding the pellicle 7 (FIG. 40) by using the oblique illuminating light beams 3820 and 3803 projected respectively by the second illuminating unit 20 and the first back illuminating unit 3. FIG. 49(B) shows a second illuminating mode for inspecting an area 4004 on the right side of the center line 4001 by using the oblique illuminating light beams 3802 and 3830 projected respectively the the first front illuminating unit 2 and the second back illuminating unit 30. These illuminating modes are used to prevent the interception of the illuminating light beam by the frame 3807 and the first illuminating mode need not necessarily be changed for the second illuminating mode when the inspection field 15 moves across the center line 4001.

Figure 41:
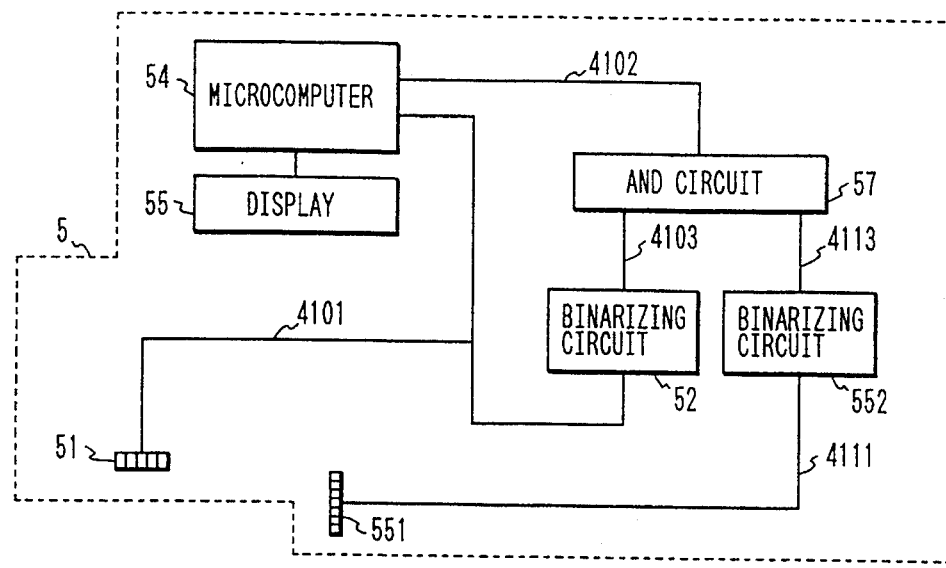
FIG. 41 is a block diagram of a signal processing unit in accordance with the present invention.

FIG. 41 is a block diagram of part of the signal processing system 5 of FIG. 1 for processing the detection signals provided by the detectors in the reticle inspecting operation in the aforesaid illuminating modes. In FIG. 41, parts corresponding to those shown in FIG. 1 are denoted by the same reference characters.

Referring to FIG. 41, scattered back illuminating light, i.e., part of the illuminating light beam emitted by the first back illuminating unit 3, not shown, or the second back illuminating unit 30, not shown, travels through the wavelength separation mirror 42, not shown, and falls on the detector 51, while scattered front illuminating light beam, i.e., part of the illuminating light beam projected by the first front illuminating unit 2, not shown, or the second front illuminating unit 20, not shown, is reflected by the wavelength separation mirror 42 and falls on the detector 551.

The binarizing circuits 52 and 552 receive the respective detection signals 4101 and 4111 of the detectors 51 and 551, execute logic operation to convert the detection signals 4101 and 4111 into corresponding logical values 4103 and 4113, respectively, and give the logical values 4103 and 4113 to the AND circuit 57. The AND circuit 57 carries out the logical AND operation between the logical values 4103 and 4113 to provide the logical product of the logical values 4103 and 4113. The output 4102, i.e., the logical product, is the results of detection of a defect, such as a foreign particle. As mentioned, it is desirable to provide the detection signals in addition to the logical level of the output 4102 of the AND circuit 57, which applies also to the following cases.

Figure 69:
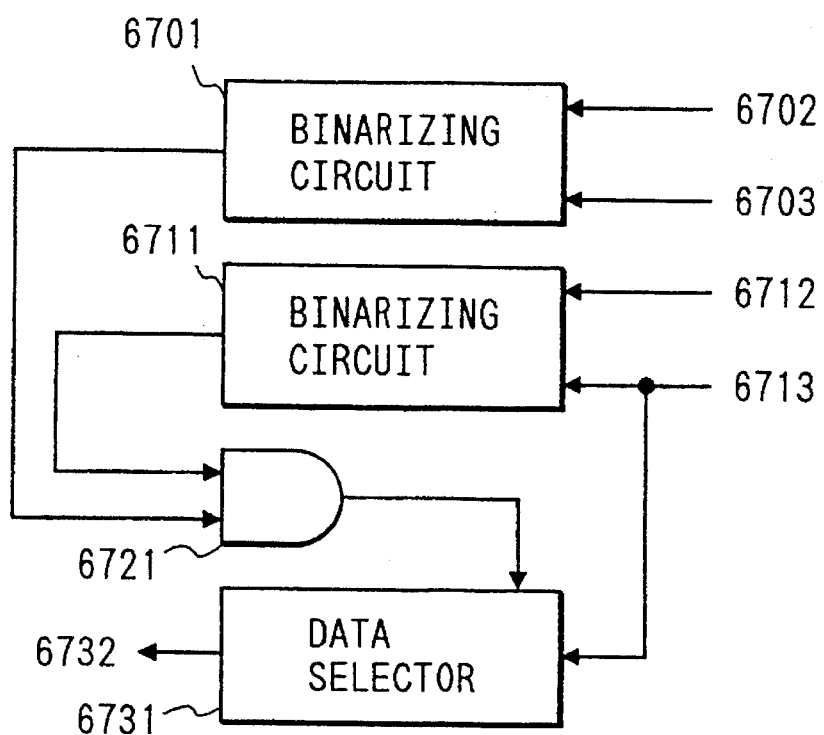
FIG. 69 is a block diagram of a detection circuit which provides a detection output on the basis of the result of an AND operation, included in a signal processing system in accordance with the present invention.

Referring to FIG. 69 showing a configuration for such a case, a threshold 6702 for binarizing detection signals provided upon the detection of scattered back illuminating light (back illuminating light detection) is set beforehand for a binarizing circuit 6701, and a threshold 6701 for binarizing detection signals provided upon the detection of scattered front illuminating light (front illuminating light detection) is set beforehand for a binarizing circuit 6701. A detection signal 6703 obtained by back illuminating light detection is given to the binarizing circuit 6701, and a detection signal 6713 obtained by front illuminating light detection is given to the binarizing circuit 6711. An AND device 6721 carries out an AND operation between the outputs of the binarizing circuits 6701 and 6711. When the output of the AND device 6721 is logical "1", a data selector 6731 selects the detection signal provided by back illuminating light detection and provides an output 6732. The output 6732 may be equal to the detection signal obtained by back illuminating light detection.

Although the foregoing procedure is effective on detecting foreign particles in the transparent area of the photomask, such as a reticle, the procedure entails the following problems in detecting foreign particles in the opaque area of the photomask. Since a foreign particle in the opaque area cannot be illuminated with the back illuminating light beam, the foreign particle does not scatter the back illuminating light beam. For example, when there is a large foreign particle, which must be detected, in the opaque area, the front illuminating light beam is scattered by the foreign particle and scattered front illuminating light having a high intensity is detected while the back illuminating light beam is not scattered and, consequently, the output of the binarizing circuit 6701 is logical "0", while the output of the binarizing circuit 6711 is logical "1". Accordingly, even if the output of the binarizing circuit 6711 (FIG. 69) is logical "1", it is not decided that there is a large foreign particle on the reticle.

To prevent such erroneous foreign particle detection, it is necessary to decide that there is a foreign particle on the reticle when the intensity of the scattered front illuminating light is high, even if no scattered back illuminating light is detected. Although this signal processing procedure is incapable of detecting minute foreign particles, scattered front illuminating light beam scattered by which has a low intensity, in the opaque area, an image of such a minute foreign particle in the opaque area is not printed on the wafer as mentioned above, and only large foreign particles which are liable to migrate from the opaque area to the transparent area need to be detected. Therefore, this signal processing procedure does not cause practical problems.

Figure 74:
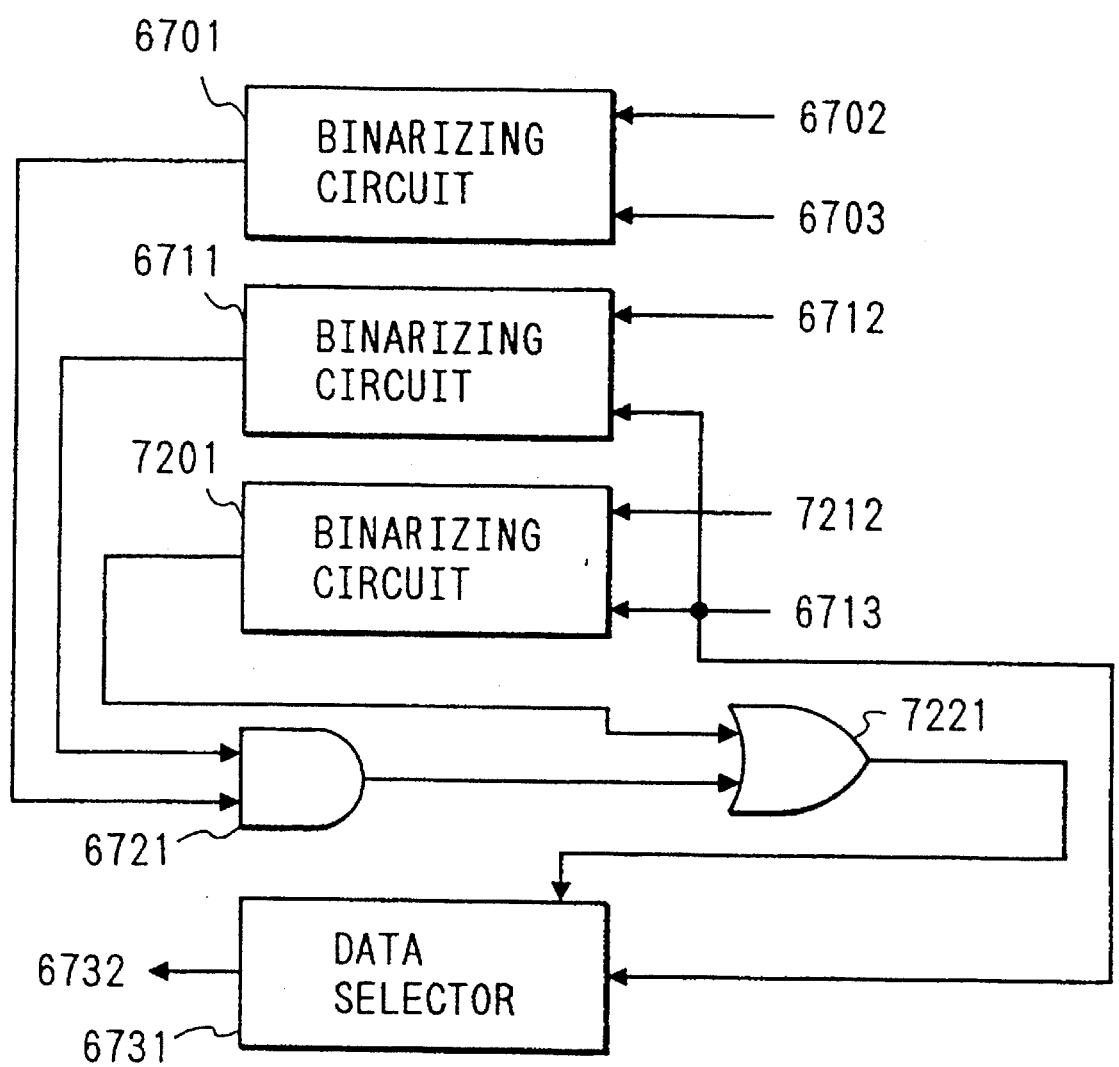
FIG. 74 is a block diagram of a detection circuit which provides a detection output on the basis of the result of AND operation, included in a signal processing system in accordance with the present invention.

FIG. 74 shows a signal processing system capable of carrying out such a signal processing procedure. The signal processing system shown in FIG. 74 is provided, in addition to the components of the signal processing system of FIG. 69, a binarizing circuit 7201 for binarizing a detection signal provided upon the detection of scattered front illuminating light, and an OR circuit 7221. A threshold 7212 is set beforehand for the binarizing circuit 7201. The threshold 7212 is greater than the threshold 6712; that is the threshold 7212 is greater than the level of the detection signal representing the intensity of scattered light scattered by the circuit pattern. When a detection signal of a level exceeding the threshold 7212 is provided, the output of the binarizing circuit 7201 is logical "1". The OR circuit 7221 carries out an OR operation between the output of the binarizing circuit 7201 and the output of the AND circuit 6721. When the output of the OR circuit 7221 is logical "1", the data selector 6731 provides an output 6732 corresponding to a detection signal 6732 obtained by front illuminating light detection. In this case, only the detection signal obtained by front illuminating light detection is provided because foreign particles in the opaque area cannot be illuminated with the back illuminating light beam.

Figure 46:
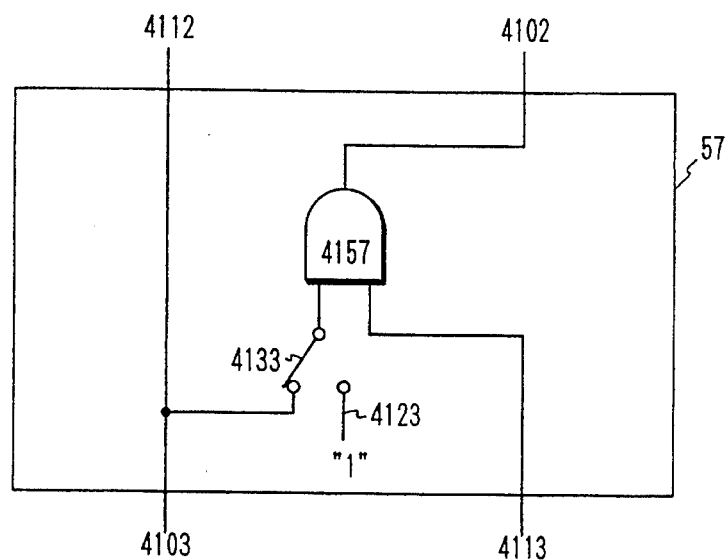
FIG. 46 is a block diagram of a signal processing unit in accordance with the present invention.
Figure 47:
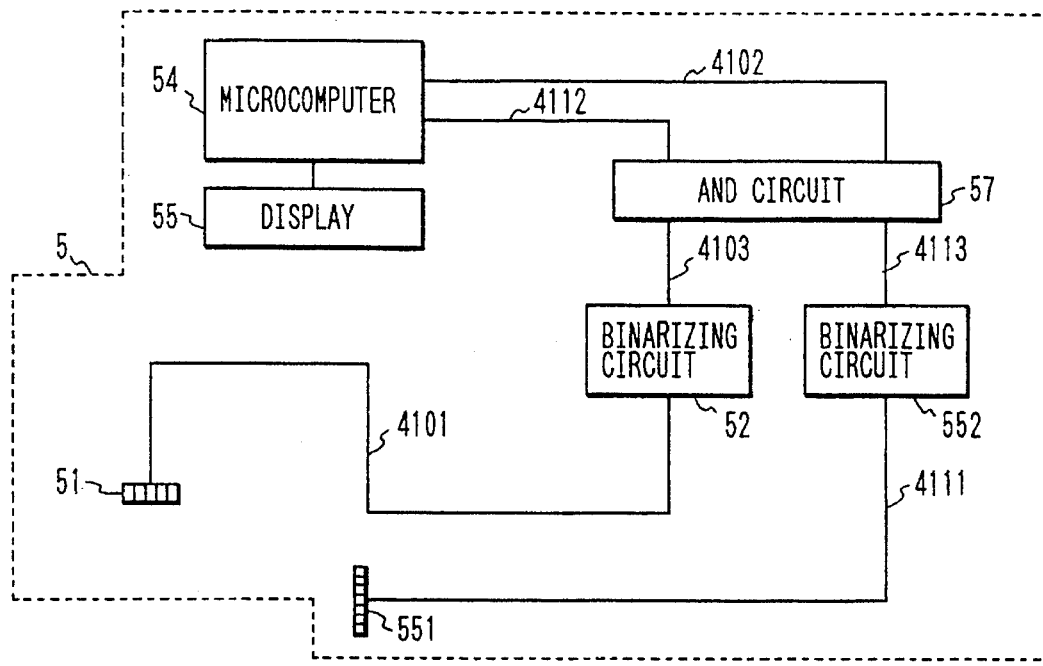
FIG. 47 is a block diagram of a signal processing unit in accordance with the present invention.

In the AND circuit 57 or the peripheral of the AND circuit 57 formed in a configuration as shown in FIG. 46, the result of the logical AND operation appears at the output 4102 of the AND circuit 57 when a detection signal 4103 is applied through a switching device 4133 to one of the inputs of the AND circuit 4157, and results of detection of a detection system not using an AND system appear at the outputs 4102 and 4112 of the AND circuit 57 when an input 4123 of logical "1" is applied through the switching device 4133 to the same input of the AND circuit 57. Thus, the detection mode of the reticle inspecting apparatus can selectively be determined. In such a case, a circuit shown in FIG. 47 is used instead of the circuit shown in FIG. 41. Since the purpose of use of the circuit shown in FIG. 46 is to enable the selective determination of the detection mode of the reticle inspecting apparatus, suitable software or the like may be employed instead of the circuit shown in FIG. 47.

When it is decided that scattered light scattered by a defect, such as a foreign particle 70, is detected, defect data indicating the positions of the X-stage 10 and the Y-stage 11 at the moment of detection of the foreign particle 70, the position of the foreign particle 70 calculated on the basis of the positions of the pixels received the scattered light among those of the detectors 51 and 651, and the respective detection signals 4101 and 4111 provided by the detectors 51 and 551 is stored in a storage device controlled by the microcomputer 54, the contents of the storage device are processed and the processed contents of the storage device are displayed on the display 55, such as a CRT.

Detection and identification of a foreign particle on the basis of the output of each pixel of a detector of an array type entails the following problems.

Suppose that a detector having pixels of 2×2 $\mu m^2$ is used for the detection and identification of a foreign particle.

Figure 26:
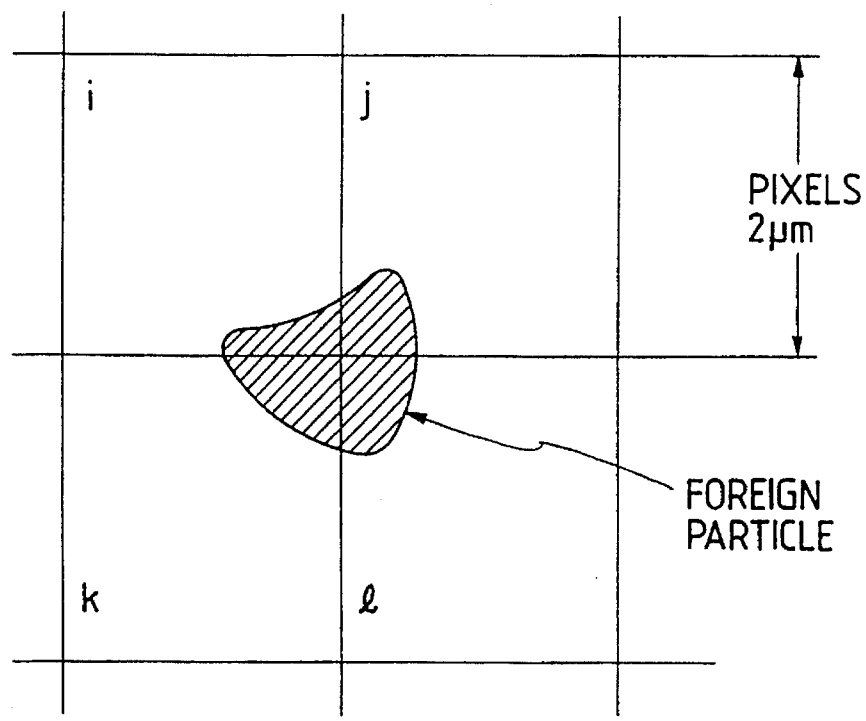
FIG. 26 is a diagrammatic view of assistance in explaining the detection of a foreign particle by a process using a 2×2 μm pixel instead of a four-pixel addition process.

Then, if the foreign particle is detected by four pixels as shown in FIG. 26, the scattered light scattered by the foreign particle is distributed to the plurality of pixels and the output of each pixel is in the range of ½ to ¼ (practically about ⅓ due to crosstalk between the pixels) of the output which may be obtained when the foreign particle is detected by a single pixel and, consequently, the detection probability is reduced. Furthermore, the positional relation between the pixels of the detector and the minute foreign particle is delicate and very liable to change and changes every time the inspection is made, which deteriorate the repeatability of the inspection. Such problems arise also when the foreign particle is detected by two pixels or three pixels as well as when the foreign particle is detected by four pixels.

Figure 27:
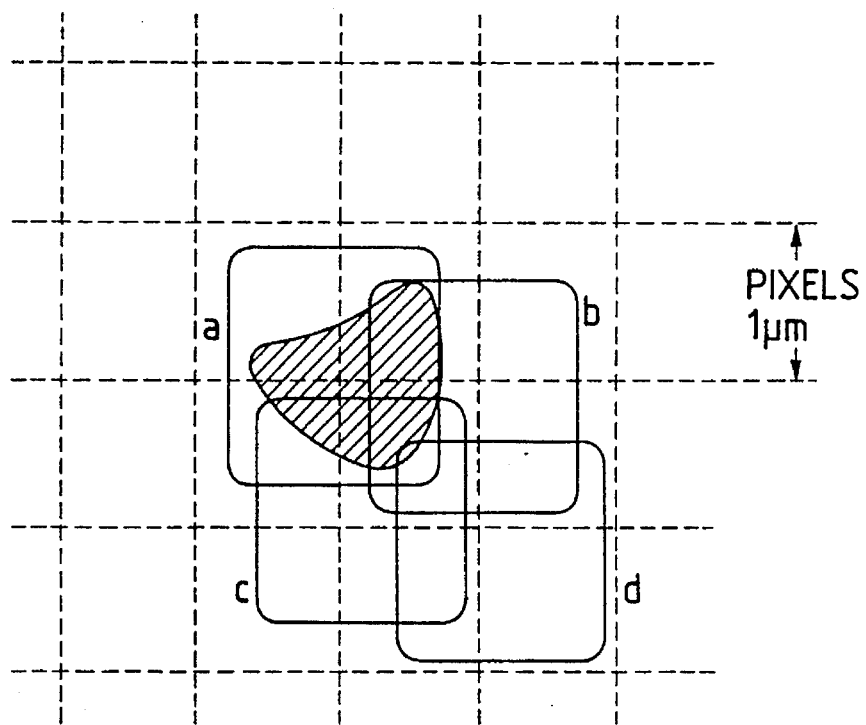
FIG. 27 is a diagrammatic view of assistance in explaining the detection of a foreign particle by a four-pixel addition process using 1×1 μm pixels.

To overcome the foregoing disadvantage, 1×1 $\mu m^2$ pixels as shown in FIG. 27 are used, and the respective detection signals provided by the four adjacent 1×1 $\mu m^2$ pixels are added electrically to simulate the detection signal of a 2×2 $\mu m^2$ pixel. The sums of the detection signals each of four adjacent pixels of each of four duplicate pixel groups a, b, c and d are calculated, and the maximum sum of outputs, i.e., the sum of outputs of the pixels of the pixel group a in FIG. 27, is considered to be equivalent to the output of a 2×2 $\mu m^2$ pixel and used as a foreign particle detection signal. In this method of detecting a foreign particle, the variation of the detection signal indicating a foreign particle is within ±10% and the repeatability of detection for all the foreign particles is 80% or above.

Figure 28:
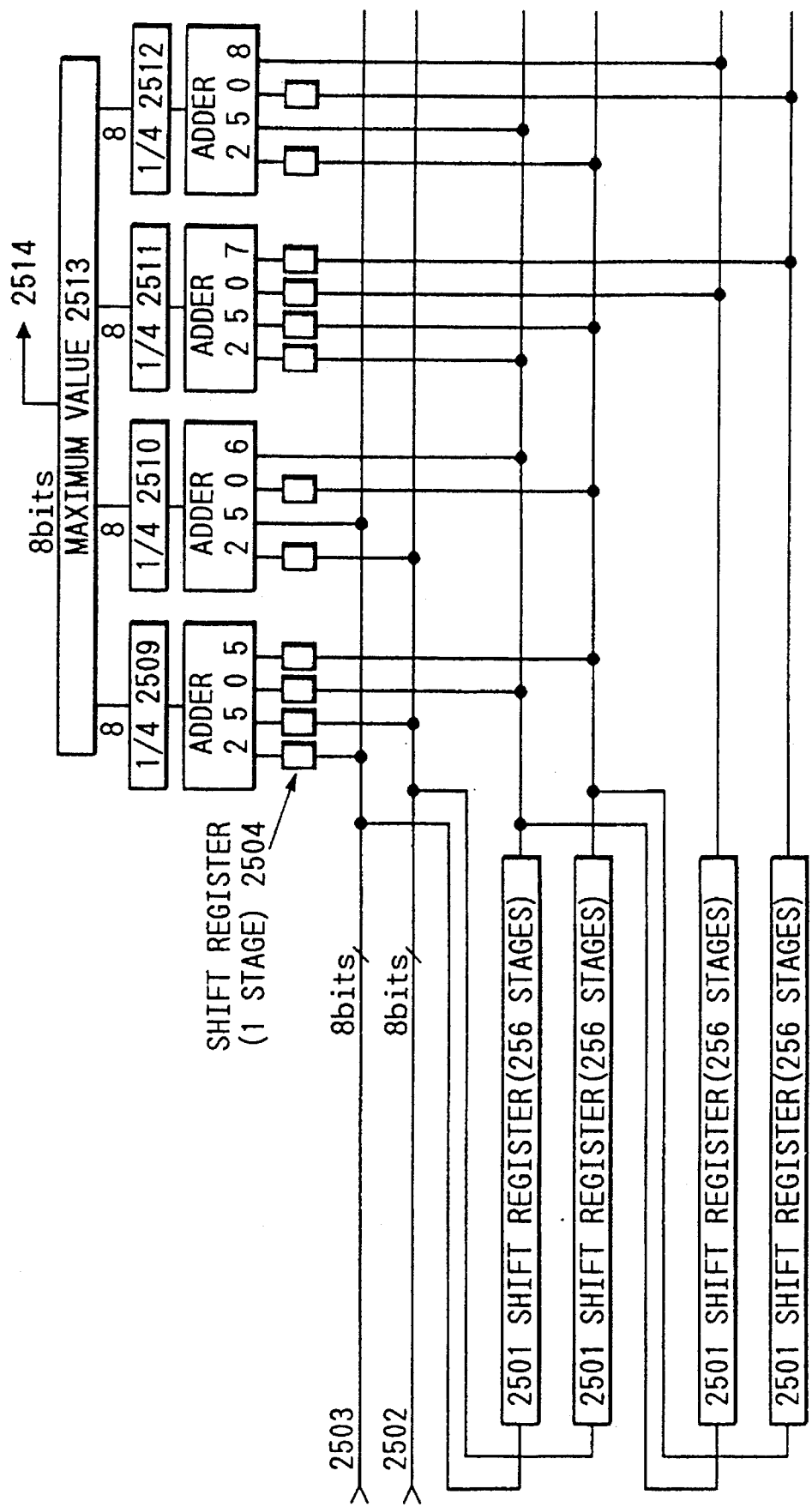
FIG. 28 is a block diagram of a four-pixel addition circuit.

FIG. 28 is a block diagram of a four-pixel addition circuit. This four-pixel addition circuit is used in combination with a one-dimensional imaging device provided with an array of 512 1 $\mu m^2$ pixels, which provides the output 2502 of even-numbered pixels and the output 2503 of odd-numbered pixels separately. The outputs of four 1×1 $\mu m^2$ pixels (2×2 pixels) shifted by one pixel in four directions are added by 256-stage shift registers 2501, one-stage shift registers 2504 and an adders 2505 to 2508, and dividers 2509 to 2512 calculate the means of the outputs of the pixels. A maximum value selecting circuit 2513 selects the maximum mean as a foreign particle detection signal 2514 from among the four means.

When the four-pixel addition circuit shown in FIG. 28 is used, one detection signal is provided for a unit of 2 µm and the quantity of data is reduced by a factor of four. Therefore, the signal processing speed of the subsequent signal processing circuit may be reduced by a factor of four, which is advantageous to designing the circuits and to the operation of the circuits. Thus, defect detecting operation can stably be carried out.

Figure 67:
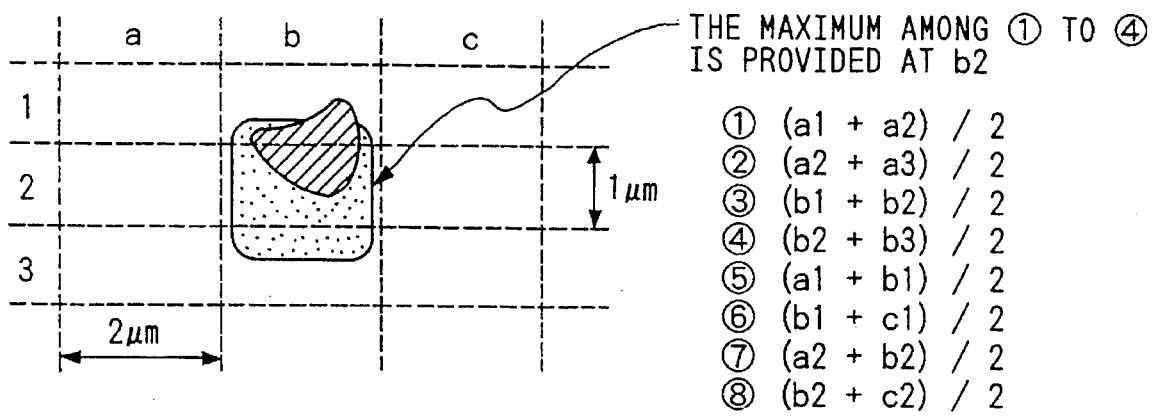
FIG. 67 is a diagrammatic view of assistance in explaining a two-pixel addition method using 2 µm×1 µm pixels.

The foregoing operations for adding the outputs of the adjacent four pixels and calculating the means are intended to prevent the reduction of the level of detection signals provided by four pixels corresponding to one foreign particle. Therefore, each pixel group may have more than four pixels or less than four pixels, provided that the desired object can be achieved. FIG. 67 shows an example of two-pixel addition operation. As shown in FIG. 67, rectangular pixels are used instead of square pixels. This can be realized by using a rectangular detector or by moving the stage at a comparatively high feed speed as compared with the detecting time of the detector; for example, a detector having a size of 1 µm×1 µm on the reticle is used and the stage is moved 2 µm in detecting time T to form 1 µm×2 µm pixels on the reticle. As shown in FIG. 67, the detection signals of two pixels are added.

In the embodiment shown in FIG. 67, (a1+a2)/2, (a2+a3)/2, (b1+b2)/2, (b2+b3)/2, (a1+b1)/2, (b1+c1)/2, (a2+b2)/2 and (b2+c2)/2 are calculated at time b2, and the maximum among the calculated results, i.e., the maximum mean among the means of added values, is provided as the detection signal. Although the effect of the two-pixel addition method on preventing the reduction of the level of the detection signals provided upon the detection of a foreign particle corresponding to four pixels is lower than that of the four-pixel addition method, the stage feed speed of the two-pixel addition method is higher than that of the four-pixel addition method and hence the two-stage addition method enhances the speed of inspection.

In the foregoing embodiment, the size of the foreign particle to be detected, for example, 0.5 μm, is smaller than the size of the pixels, for example, 2 μm×2 μm, of the detector. Therefore, if a foreign particle corresponds to one pixel of, for example, 1 μm×1 μm, a detection signal provided by the detector before the four-pixel addition operation is equal to a detection signal obtained by the four-pixel addition operation and provided by the detector, because the detection signal compensating effect of the four-pixel addition operation is effective only when a foreign particle corresponds to a plurality of pixels. The smaller the area (size) of the pixels of the detector, the smaller is the number (area) of the corners of the circuit pattern corresponding to one pixel and hence the lower is the intensity of scattered light scattered by the circuit pattern. Therefore, the smaller pixels are desirable for for the detection of foreign particles in higher sensitivity. It may safely be said that the four-pixel addition method sacrifices detection sensitivity for stable detection. Although any measures need not be taken to solve this problem if the reduced detection sensitivity is high enough, some measures must be taken to make the detection sensitivity effective even if process conditions and exposure method are changed.

The problem may be solved by selectively using a high-stability detection mode including the four-pixel addition operation or a high-sensitivity detection mode not including the four-pixel addition operation according to required performance.

Both the purposes of high-stability detection mode and the high-sensitivity detection mode can be achieved through the detection of foreign particles before and after the four-pixel operation. The present invention employs a signal processing system as shown in FIG. 42 to achieve the purposes of both the high-stability detection mode and the high-sensitivity detection mode.

Figure 42:
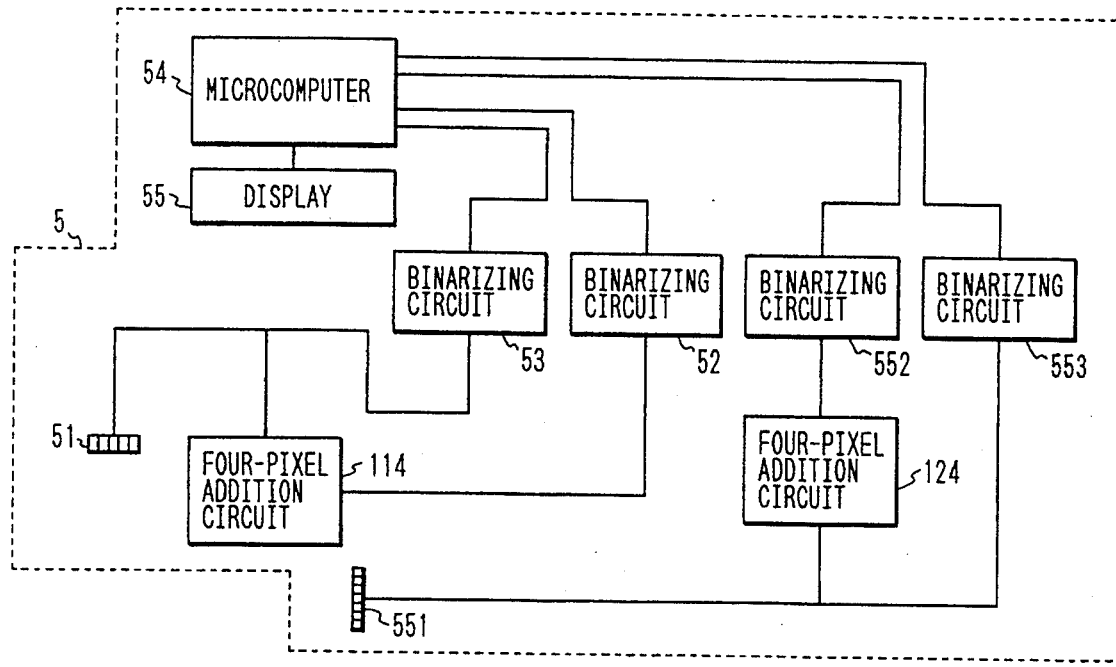
FIG. 42 is a block diagram of a signal processing unit in accordance with the present invention.

Referring to FIG. 42, a detection signal provided by a detector 51 (551) is processed by a four-pixel addition circuit 114 (124), the output of the four-pixel addition circuit 114 (124) is binarized by a binarizing circuit 52 (552), and the detection signal provided by the detector 51 (551) is binarized by a binarizing circuit 53 (553), the outputs of the binarizing circuits 114 (124) and 53 (553) are stored in a storage included in a computer 54, and displayed on a display 55.

Figure 43:
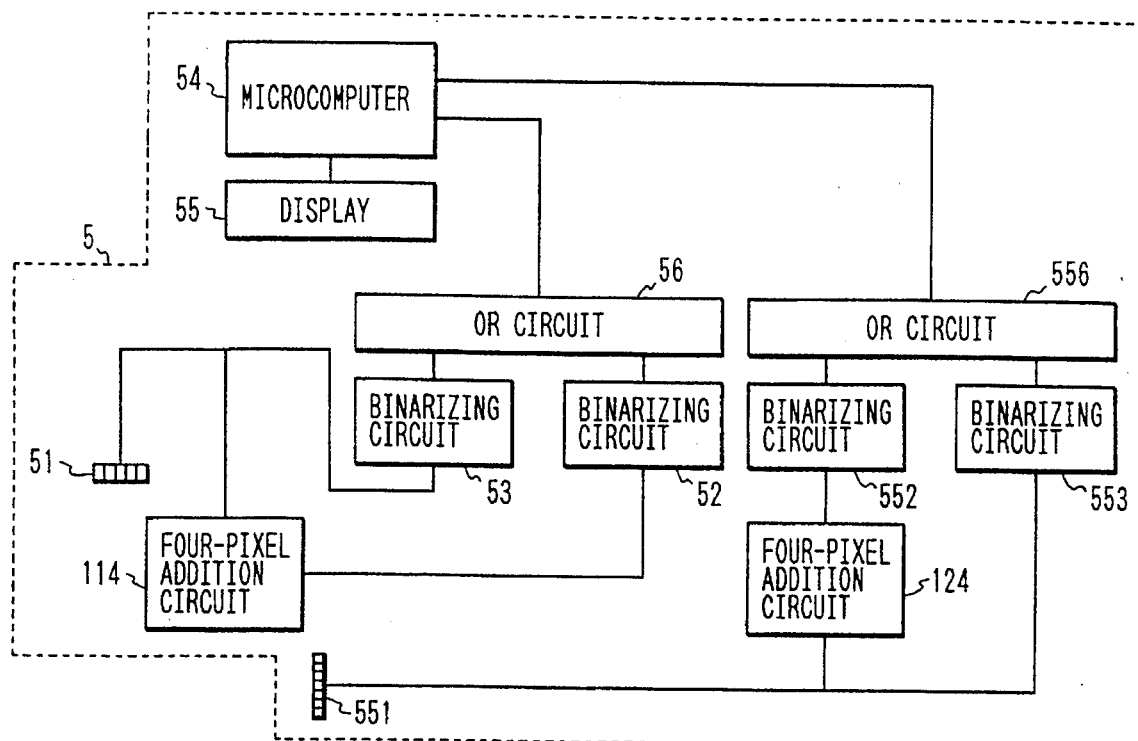
FIG. 43 is a block diagram of a signal processing unit in accordance with the present invention.
Figure 68:
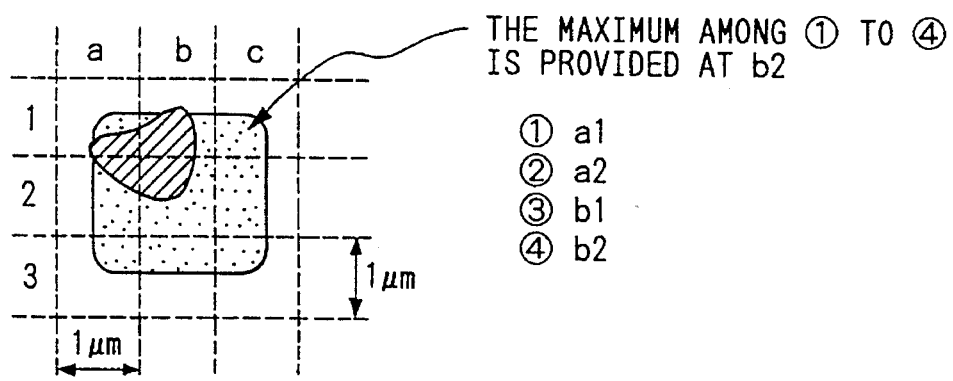
FIG. 68 is a diagrammatic view of assistance in explaining a four-pixel addition method using 1 µm×1 µm pixels.

A foreign particle can be detected on the basis of either the output of the binarizing circuit 52 (552) or that of the binarizing circuit 53 (553). Therefore, the quantity of defect detection data obtained by detecting foreign particles on the circuit pattern can be reduced by subjecting the outputs of the binarizing circuits 52 and 552, and the outputs of the binarizing circuits 53 and 553 to the logical OR operation of OR circuits 56 and 556 and storing the outputs of the OR circuits 56 and 556 in a storage included in a computer 54 as shown in FIG. 43. When the four-pixel addition operation provides the maximum value to reduce the quantity of data, it is difficult to compare the data provided by the four-pixel addition operation with the data not processed by the four-pixel addition operation. In such a case, the maximum value among the four detection signals not processed by the four-pixel addition operation is used to reduce the quantity of data by a factor of four as shown in FIG. 68 to facilitate the logical OR operation. The maximum among a1, a2, a3 and a4 at a moment b2 is provided as a detection signal.

The desirable effect of providing the detection signals in addition to the logical level holds good for the logical OR operation as well as for the logical AND operation.

Figure 70:
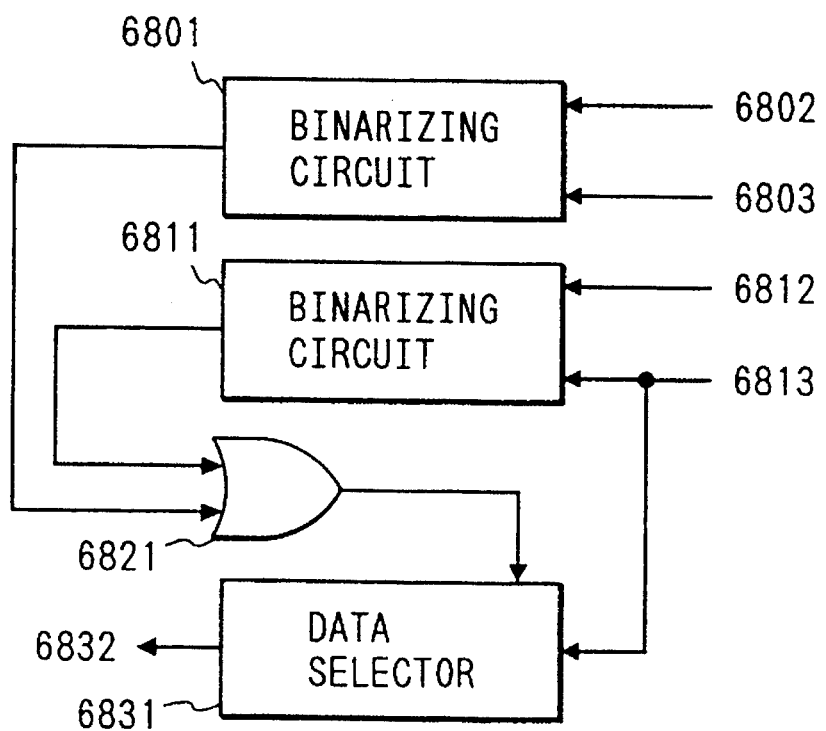
FIG. 70 is a block diagram of a detection circuit which provides a detection output on the basis of the result of AND operation, included in a signal processing system in accordance with the present invention.
Figure 71A:
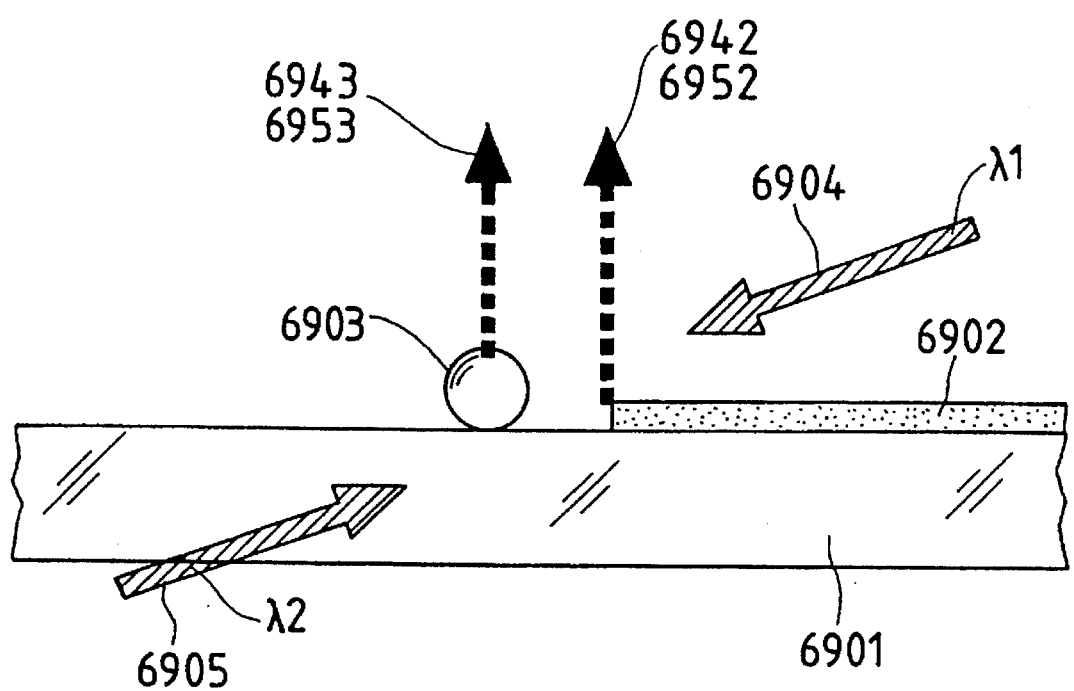
FIGS. 71(A)–71(C) are diagrammatic views of assistance in explaining the condition of scattered light and detection output corresponding to the scattered light.
Figure 71B:
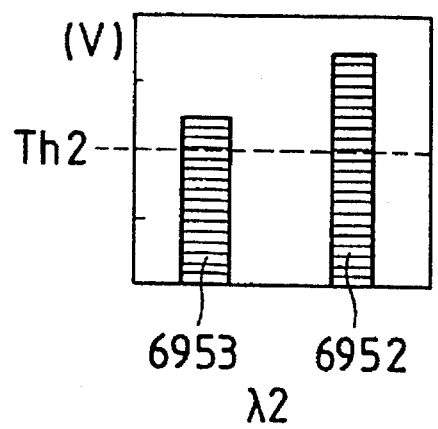
Figure 71C:
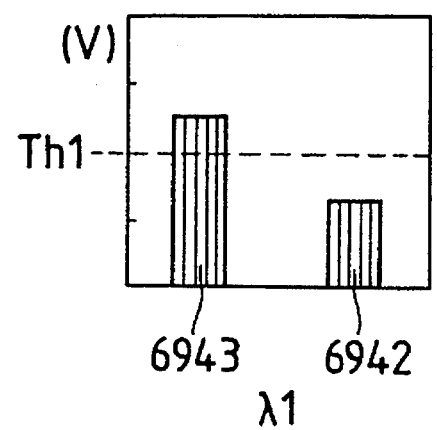
Figure 72A:
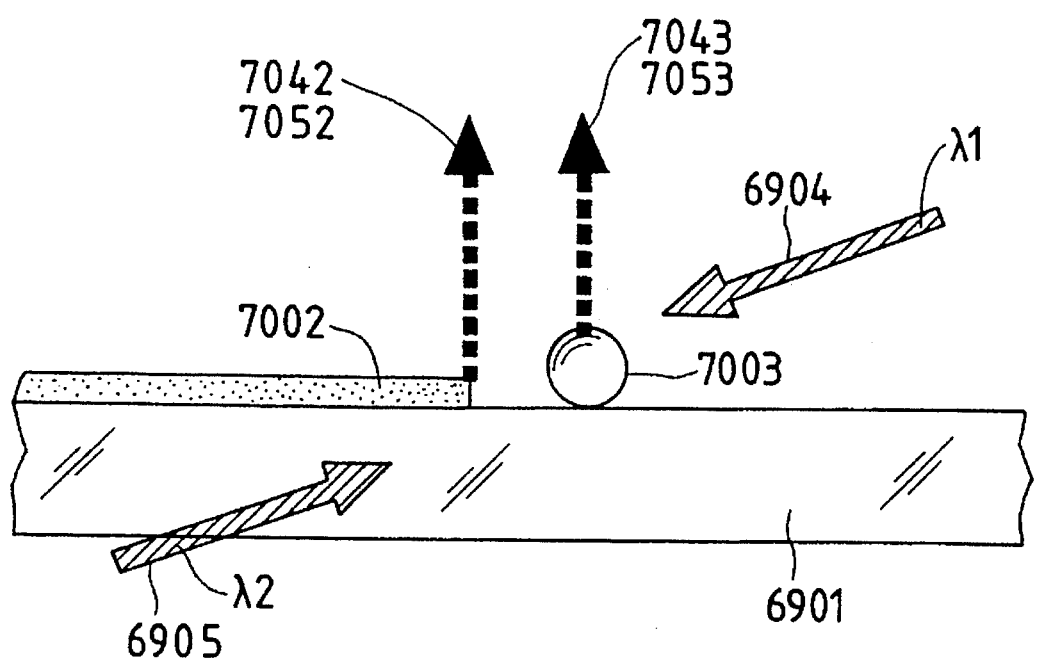
FIGS. 72(A)–72(C) are diagrammatic views of assistance in explaining the condition of scattered light and detection output corresponding to the scattered light.
Figure 72B:
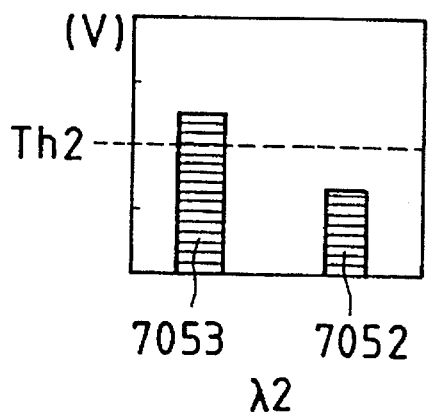
Figure 72C:
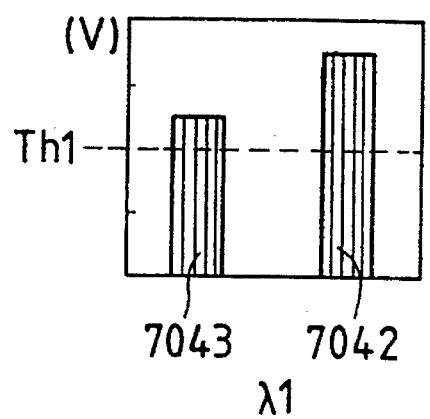
Figure 73A:
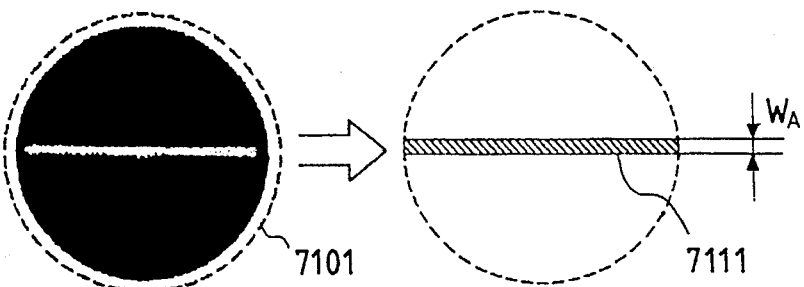
FIGS. 73(A) 73(B), 73(C) and 73(D) are plan views of different kinds of scattered light scattered by different circuit patterns, and corresponding spatial filters.
Figure 73B:
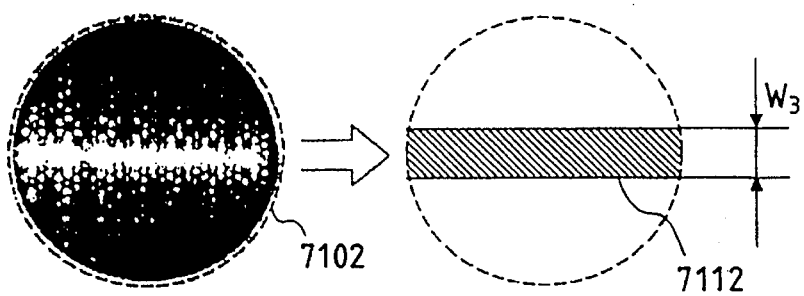
Figure 73C:
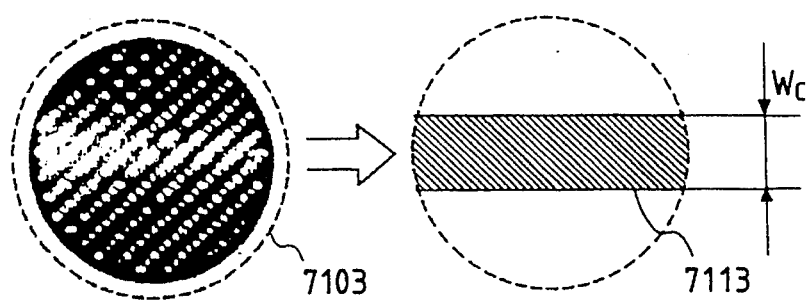
Figure 73D:
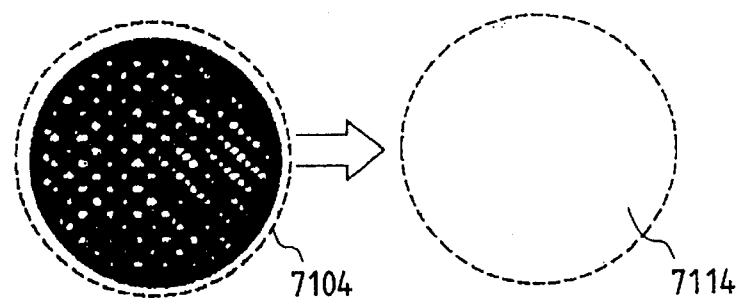

Such a method of detection can be achieved by an arrangement shown in FIG. 70. A threshold 6802 is set for a binarizing circuit 6801 for binarizing detection signals not processed by the four-pixel addition operation, and a threshold 6812 is set for a binarizing circuit 6811 for binarizing detection signals obtained through the four-pixel addition operation. The binarizing circuit 6801 binarizes detection signals 6803 not processed by the four-pixel addition operation, and the binarizing circuit 6811 binarizes detection signals obtained through the four-pixel addition operation. An OR circuit 6821 carries out the logical OR operation between the outputs of the binarizing circuits 6801 and 6811. When the output of the OR circuit 6821 is logical "1", a data selector 6831 selects a detection signal 6832.

When the signal processing system provided with neither the OR circuit 56 nor the OR circuit 556 as shown in FIG. 42 is employed, it is desirable to carry out the logical OR operation between the detection signals by software before displaying the detection signals on the display 55.

Figure 44:
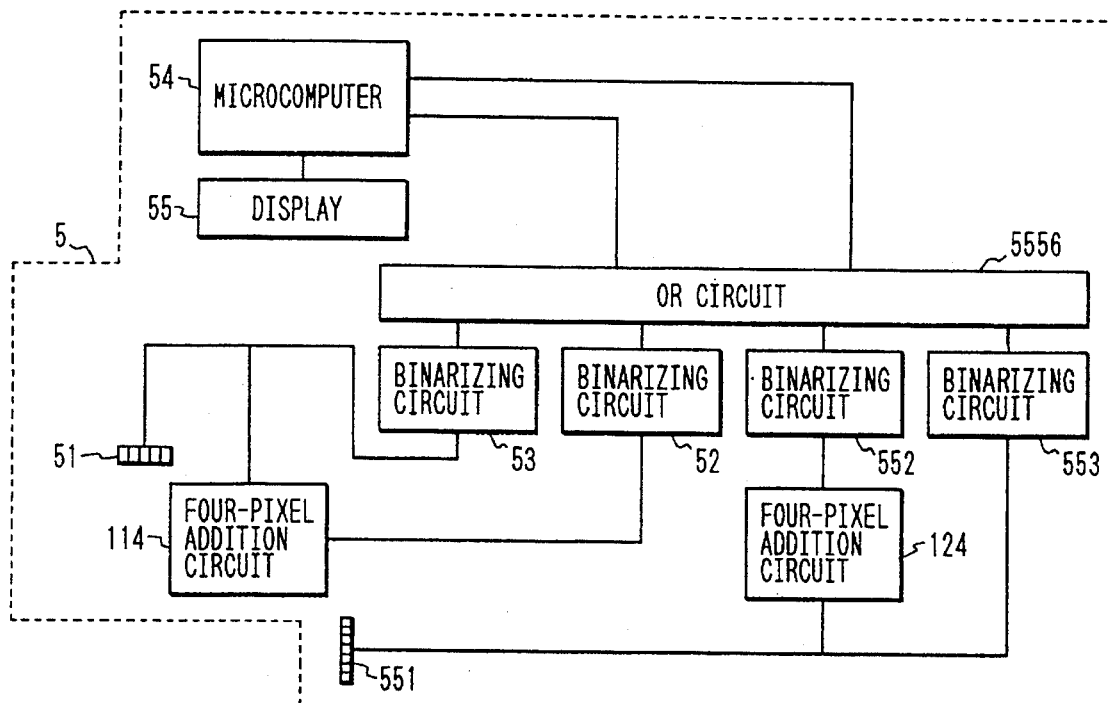
FIG. 44 is a block diagram of a signal processing unit in accordance with the present invention.

When the logical AND operation is not used for defect detection, the logical OR operation between the outputs of the binarizing circuits 52 and 552 and between the outputs of the binarizing circuits 53 and 553 may be carried out by the OR circuit 5556 as shown in FIG. 44 or by software.

Figure 45:
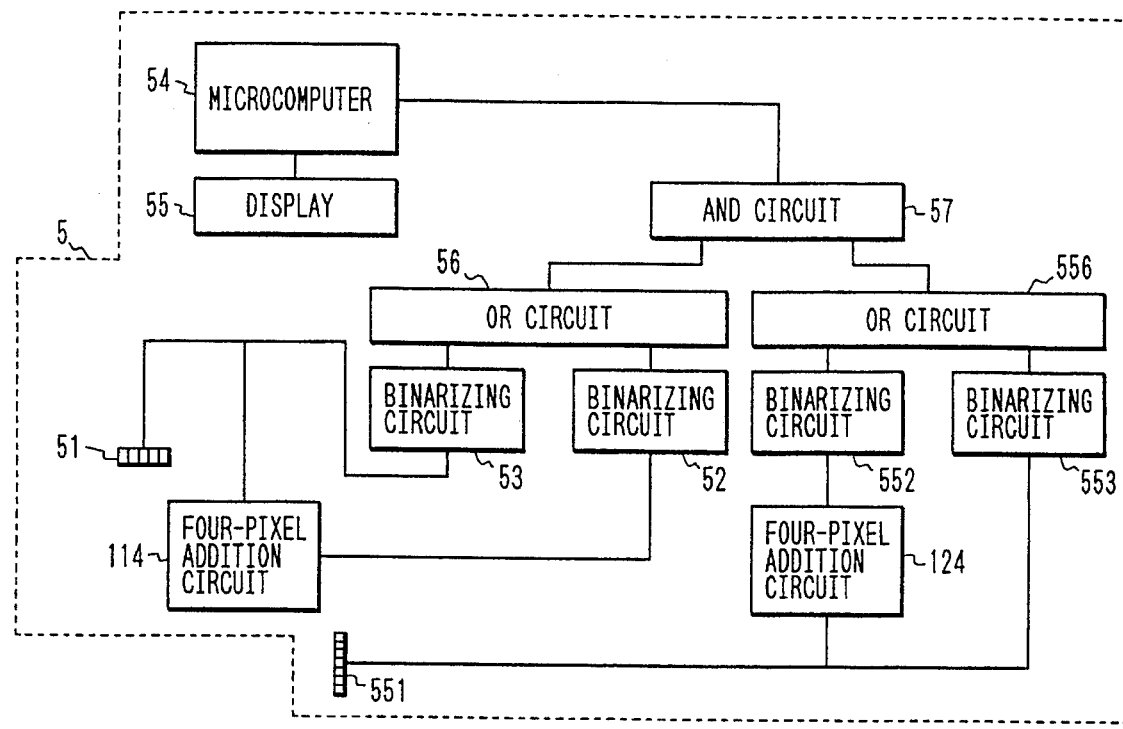
FIG. 45 is a block diagram of a signal processing unit in accordance with the present invention.

As shown in FIG. 45, when the logical AND operation is used for defect detection, an AND circuit 57 carries out the logical AND operation between the outputs of OR circuits 56 and 556. Since the result of the logical AND operation is the final result of defect detection, it is desirable to carry out the logical AND operation during inspection. The execution of the logical AND operation by an AND circuit is more practical than that by software.

Figure 29:
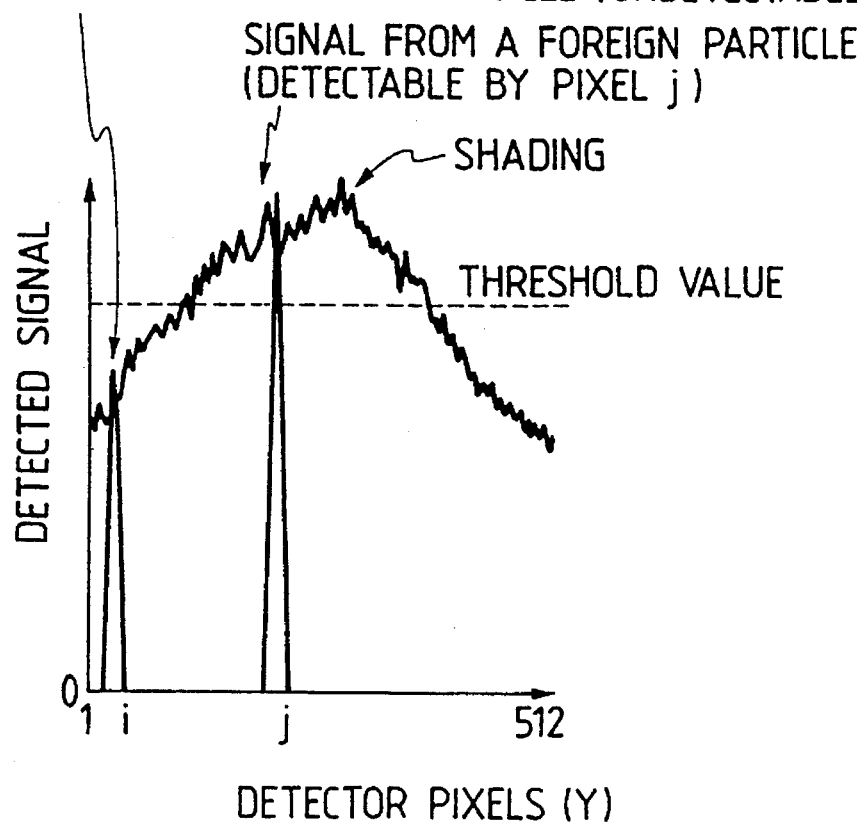
FIG. 29 is a graph of assistance in explaining the effect of shading on the detection of foreign particles.

The reticle inspecting apparatus of the present invention actualizes only foreign particles optically for detection, and binarizes the detection signal when the detection signal is greater than the threshold to detect a foreign particle. However, the detection signal is subject to change due to (1) the difference between the pixels in sensitivity (about ±15%) and (2) the difference between the pixels in output level attributable to the distribution of illuminance on the reticle (shading). Therefore, the different pixels provides different detection signals for the same foreign particle as shown in FIG. 29 and the level of the output signal is dependent on the position of the pixel with respect to the direction along the Y-axis. Thus, it is impossible to detect a foreign particle stably through the binarization of the detection signal exceeding the threshold.

Figure 30A:
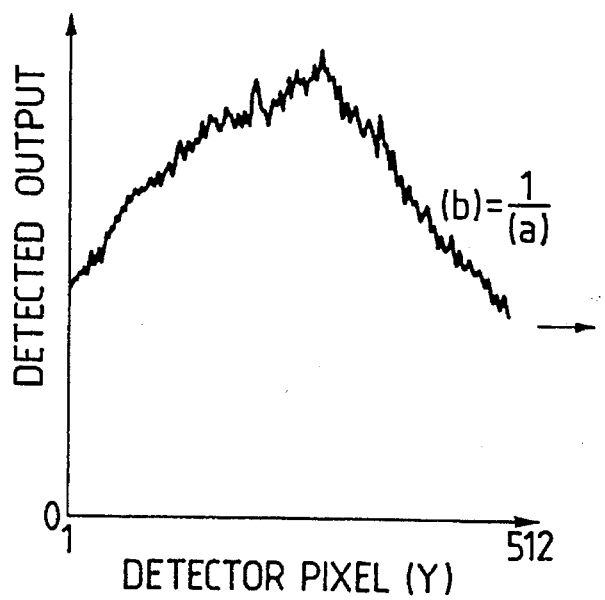
FIGS. 30(a), 30(b) and 30(c) are graphs of assistance in explaining the principle of shading, showing measured data of shading as measured, compensated data of shading and compensated measured data of shading, respectively.
Figure 30B:
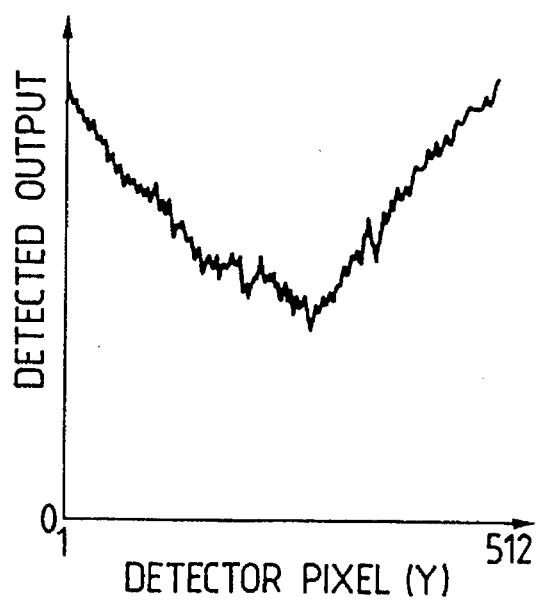
Figure 30C:
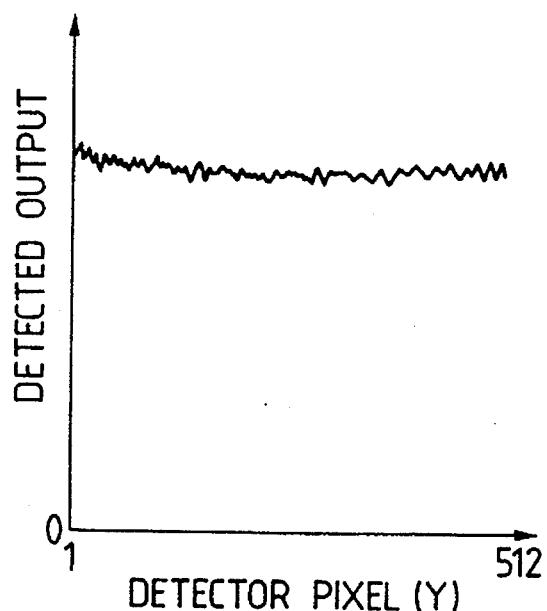

The present invention measures the shading effect of the causes (1) and (2) (FIG. 30(a)) beforehand by using a standard reticle 111 (FIG. 1), calculates the reciprocal of the measured shading effect to determine shading compensating data (FIG. 30(b)) and controls the gain of an amplifier for amplifying the detection signal of the detector for the respective outputs of the pixels to obtain compensated outputs of the pixels (FIG. 30(c)) by eliminate the influence of the shading effect. The standard reticle 111 may be mounted on or disposed near the Z-stage 10 of the inspection stage unit 1 or may be mounted on the Z-stage only when measuring the shading effect.

The standard reticle 111 has a surface having minute irregularities and uniform scattering characteristic. For example, the standard reticle 111 may be a glass plate having a surface having minute irregularities formed by grinding, a glass plate having a surface to which standard particles of a specific size are attached uniformly or a plate provided with an aluminum film formed by sputtering. Practically, it is difficult to form minute irregularities corresponding to a 1×1 $\mu m^2$ pixel uniformly for the standard reticle 111. Therefore, the shading effect measurement is repeated many times, for example 1000 times and determines the compensated data on the basis of the mean of the measured data.

Since only portions of the surface of the standard reticle 111 having minute irregularities scatter light and light is not scattered by the entire surface of the standard reticle 111, the addition of measured values obtained by repeating measurement 1000 times is not equivalent to and far smaller than the addition of 1000 distributions of illuminance over the entire illuminated area of the surface of the standard reticle 111. Therefore the simple mean, such as the means of measured data obtained by dividing the sum of measured data by the number of repetition of measurement, is excessively small for accurate calculation. Under such a condition, the mean may be determined by dividing the sum of the measured data by a divisor, for example, 200, which is a fragment of the number of repetition of measurement, for example, 1000.

As is obvious from the comparative examination of FIGS. 30(a) and 30(c), the shading of about 50% (FIG. 30(a) is reduced to 5% or below by correction. The adverse effect of the optical components of causes of variation in the compensated data attributable to the time-dependent variation of the performance of the illuminating system and the detection optical system can be eliminated by determining and renewing the compensated data every time the inspection is conducted.

Figure 31:
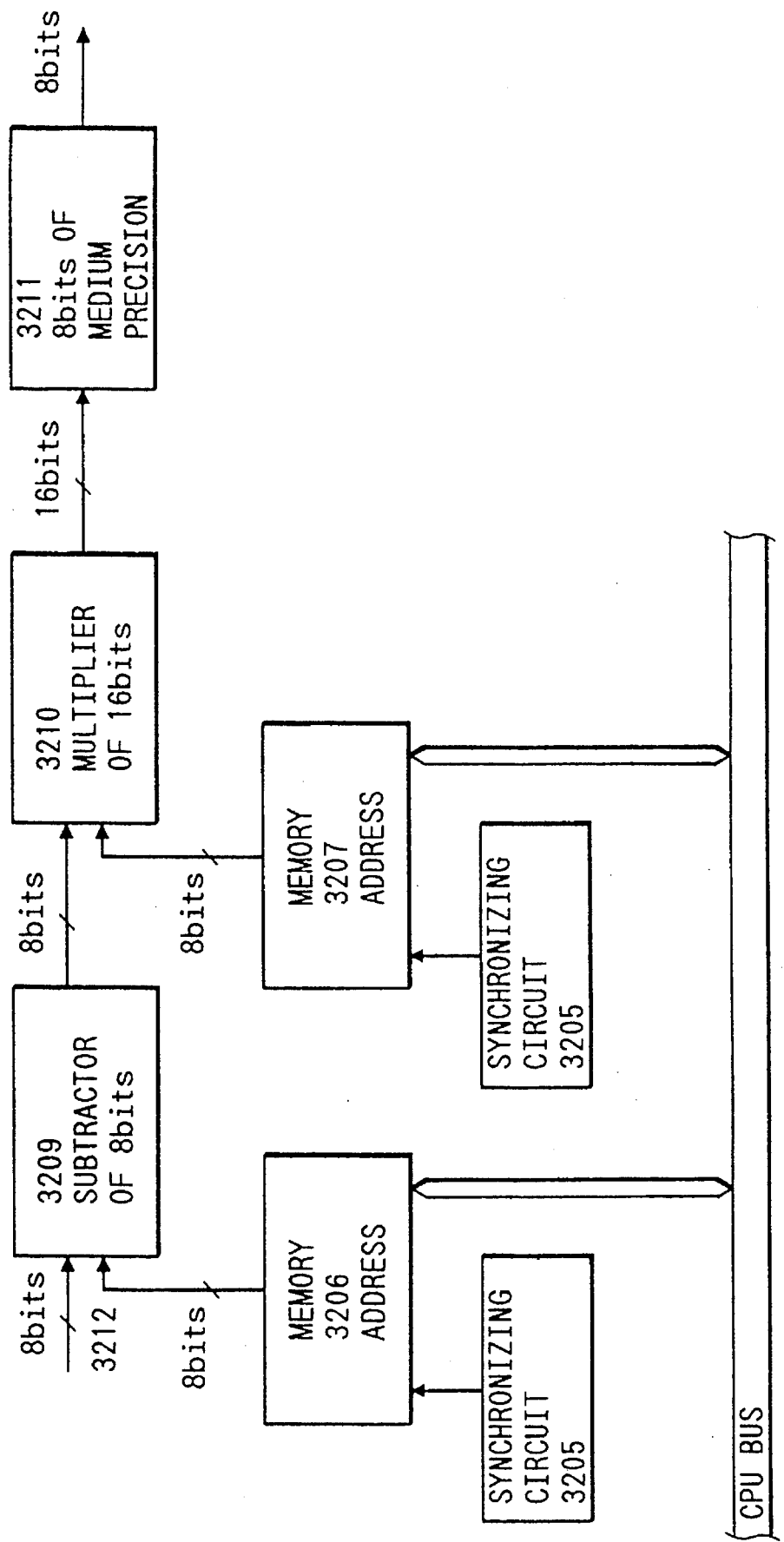
FIG. 31 is a block diagram of a shading compensating circuit.

As shown in FIG. 31 a shading compensating circuit for compensating shading comprises a subtracter 3209 which subtracts data representing the dark current of each pixel and read from a memory 3206 controlled by a synchronizing circuit 3205 from an 8-bit value 3212 (256 steps) obtained through the A/D conversion of a detection signal provided by the one-dimensional imaging device, a multiplier 3210 which multiplies a shading compensation factor by data for each pixel read from a memory 3207 controlled by a synchronizing circuit 3205, and a medium bit signal output circuit 3211 which changes the number of bits of a calculated 16-bit value, which is twice the number of bits, i.e., eight bits, of the 8-bit value 3212 obtained through the A/D conversion of the detection signal provided by the one-dimensional imaging device, for the initial number of bits, i.e., eight bits. Although this shading compensating circuit is a digital circuit that deals with digital values, analog data may be used for compensation.

If 2×2 $\mu m^2$ pixels are used for detecting foreign particles having sizes greater than 2 $\mu m$, the number of pixels detected the foreign particles is not equal to the number of detected foreign particles. When 2×2 $\mu m^2$ pixels are used for detecting A foreign particle of 10 $\mu m$, twenty-five pixels ($10^2/^2=25$) will provide detection signals and the twenty-five detection signals must be examined to observe the detected foreign particle.

The conventional reticle inspecting method examines the positional relation between the pixels which have detected foreign particles by software and decides that one foreign particle is detected by grouping when the pixels which have detected foreign particles are adjacent pixels to avoid the necessity of examining so many detection signals. This conventional method, however, needs software processes and need much time for processing many detection signals, for example, about ten minutes for processing 1000 detection signals.

The present invention divides the entire inspection region into a plurality of field blocks (blocking) which can be simultaneously observed, such as field blocks each of 32×32 $\mu m^2$, and regards all the detection signals corresponding to each field block as detection signals obtained by detecting one and the same foreign particle. Thus, even a large foreign particle can be caught in the field block for observation regardless of its shape.

Although blocking is functionally equivalent to grouping, blocking can be easily achieved by hardware. The present invention carries out blocking in a real-time mode by hardware, reduces the inspection time and enhances the throughput of the reticle inspecting apparatus. The reticle inspecting apparatus of the present invention is able to examine 1000 detection signals in a time ⅔ times the time required by the conventional reticle inspecting apparatus.

Figure 32:
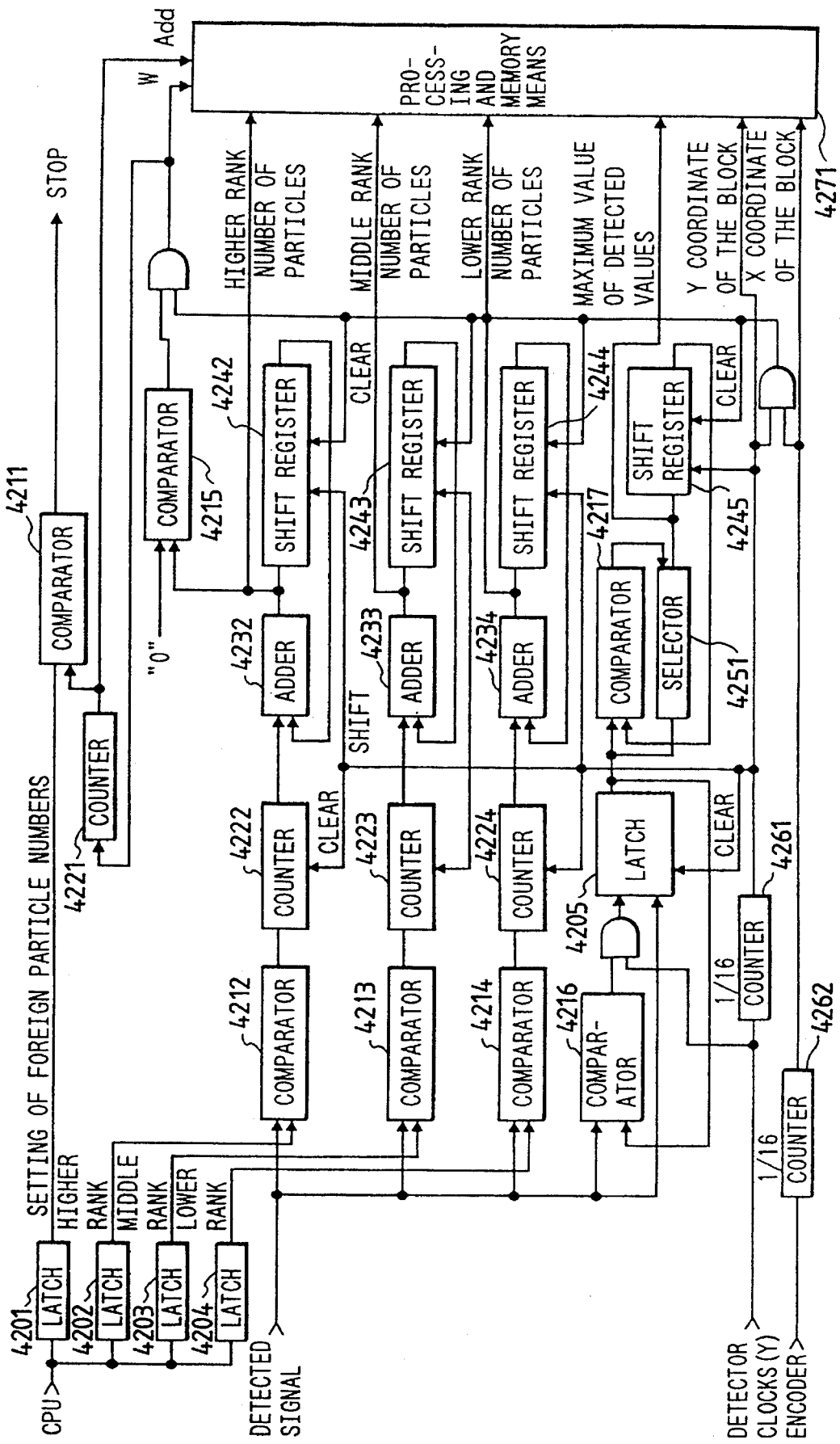
FIG. 32 is a block diagram of a block processing circuit.

Referring to FIG. 32, a blocking circuit classifies detection signals provided by the detector according to magnitude into detection signals of three ranks, namely, those of a large rank (large foreign particle detection signals) corresponding to large foreign particles, those of a medium rank (medium foreign particle detection signals) corresponding to medium foreign particles and those of a small rank (small foreign particle detection signals) corresponding to small foreign particles, counts the respective numbers of large foreign particle detection signals, medium foreign particle detection signals and small foreign particle detection signals in each pixel block of 256 pixels (=16×16 pixels) and, only when the number of foreign particles in each pixel block is 1 or above, writes the respective numbers of the large, medium and small foreign particles included in each pixel block, the maximum detection signal among those provided by the pixels of each block and the coordinates of the each block in a storage device.

A CPU sets a latch 4201 to a maximum number of foreign particles as an upper limit number of foreign particles to be detected. If the number of foreign particles exceeds the maximum number, the inspection is interrupted because the further inspection of a reticle having so many foreign particles is insignificant. A counter counts the number of detected foreign particles and a comparator 4211 compares the count of the counter 4221 with the maximum number to which the latch 4201 is set. If the count of the counter 4221 is greater than the maximum number, the inspection is interrupted.

The CPU sets a latch 4202 to a high threshold for discriminating detection signals indicating large foreign particles from those indicating medium and small foreign particles. When the level of a detection signal is higher than the high threshold, it is decided that the detection signal indicates the detection of a large foreign particle. A comparator 4212 compares the detection signal with the threshold and, if the detection signal is higher than the threshold, the count of a counter 4222 for counting the number of large foreign particles is incremented by one.

The CPU sets a latch 4203 to a medium threshold for discriminating detection signals indicating medium foreign particles from those indicating small foreign particles. A comparator 4213 compares a detection signal with the medium threshold and, if the detection signal is higher than the medium threshold, it is decided that the detection signal indicates a medium foreign particle and the count of a counter 4223 is incremented by one.

The CPU sets a latch 4204 to a low threshold for discriminating detection signals indicating small foreign particles from those indicating matters other than foreign particles. A comparator 4214 compares a detection signal with the low threshold and, if the detection signal is higher than the low threshold, it is decided that the detection signal indicates a small foreign particle and the count of a counter 4224 is incremented by one.

In the foregoing foreign particle counting operation, the number of large particles is counted by all the counters, namely, the counter 4222 for counting large foreign particles, the counter 4223 for counting medium foreign particles and the counter 4224 for counting small foreign particles, and the number of medium foreign particles is counted by both the counter 4223 for counting medium foreign particles and the counter 4224 for counting small foreign particles. Accordingly, the number of small foreign particles is determined by subtracting the number of medium foreign particles from the output of the counter 4224 for counting small foreign particles, and the number of medium particles is determined by subtracting the number of large foreign particles from the output of the counter 4223 for counting medium foreign particles. The respective numbers of large foreign particles, medium foreign particles and small foreign particles may be determined when displaying or providing the result of inspection. The detection signals may be compared by two comparators to make discrimination between detection signals indicating large, medium and small foreign particles. For example, only detection signals between a high threshold for large foreign particles and a medium threshold for medium foreign particles are selected as those indicating medium foreign particles, and only detection signals between the medium threshold and a low threshold for small foreign particles are selected as those indicating small foreign particles.

Adders 4232, 4233 and 4234, and shift registers 4242, 4243 and 4244 blocks the array of one-dimensional detector, such as a CCD detector into two-dimensional blocks each of, for example, 16×16=256 pixels. The number of steps of the shift register is equal to (The number of pixels of the CCD array)/(The number of pixels on one side of the block). In this case, the number of pixels of the CCD array is 256 and the number of pixels on one side of the block is 16, and hence the number of steps of the shift register is 256/16=16. Although the number of steps of the shift register is equal to the number of pixels on one side of the block in this example, the coincidence of those numbers is an accident and the number of steps of the register and that of the pixels on one side of the block need not necessarily be equal to each other. However, if the value of (The number of pixels of the CCD array)/(The number of pixels on one side of the block) is not an integer, a blocking circuit having a complex configuration is necessary. Therefore, it is desirable to determine the number of pixels of the CCD array and the number of pixels on one side of the block so that the value of (The number of pixels of the CCD array)/(The number of pixels on one side of the block) is an integer.

The contents of the counter 4222 for counting the number of large foreign particles are cleared (reset to zero) every time detection signals are provided by the pixels on one side of each block (sixteen pixels) are counted. A clear signal is obtained by dividing a clock which is provided for each of pixels arranged along the Y-axis of the detector by sixteen by means of a frequency divider (counter) 4261. In this case, a transfer clock of CCD array may be used as the clock for each of pixels arranged along the Y-axis. The count of the counter 4222 immediately before clearing, i.e., the count of detection signals for the sixteen pixels arranged along the Y-axis, is added to a value that appears at the output terminal of the 16-step shift register 4242 for large foreign particles by the adder 4232 and the output signal of the adder 4232 is applied to the input terminal of the 16-step shift register 4242 for large foreign particles. Then, the contents of the 16-step shift register 4242 is shifted by one step by the clear signal obtained by dividing the clock that is provided for each of the sixteen pixels arranged along the Y-axis. Therefore, the contents of the 16-step shift register 4242 is shifted by one step for every sixteen pixels arranged along the Y-axis. The contents of the 16-step shift register 4242 appears at the output terminal every time the contents of the same is shifted by sixteen steps. At this time, the CCD array is shifted a distance corresponding to one pixel along the X-axis and the number of large foreign particles detected by the sixteen pixels arranged along the Y-axis is added to the contents of the 16-step shift register 4242 by the adder 4232. The contents of the 16-step shift register 4242 is cleared by a signal obtained by dividing a pulse provided by an encoder provided every time the CCD array is shifted a distance corresponding to one pixel along the X-axis by sixteen by means of a frequency divider (counter) 4262; that is, the contents of the 16-step shift register 4242 is cleared every time the CCD array is shifted a distance corresponding to sixteen pixels arranged along the X-axis. Accordingly, the contents of the 16-step shift register 4242 for large foreign particles is the number of large particles detected by the 16×16=256 pixels. When a comparator 4215 decides that the number of large foreign particles is not zero, signal representing the number of foreign particles and the coordinates of the block is given to a processing and memory means 4271, in which the number of foreign particles is the count of the counter 4224 equal to the sum of the respective numbers of detected large, medium and small foreign particles. Modes of operation of the blocking circuit for medium foreign particles and for small foreign particles are thee same as that for large foreign particles described above.

A circuit for selecting the maximum detection signal from among those included in each block processes 16×16=256 pixels by a maximum detection signal selecting procedure, which is the same as the foreign particle counting procedure for counting the number of detected foreign particles except that the former procedure uses a latch 4205 for holding the maximum detection signal provided by one of the sixteen pixels arranged along the Y-axis instead of the latches 4201, 4202 and 4203 and the counters 4222, 4223 and 4224, and a comparator 4217 and a selector 4251 instead of the adders 4232, 4233 and 4234, by using a clear signal for sixteen pixels arranged along the Y-axis, and a 16-step shift register 4245.

The storage device for storing foreign particle data stores (1) the number of detection signals indicating comparatively large foreign particles and exceeding the threshold for detection signals indicating comparatively large foreign particles, i.e., the number of comparatively large foreign particles in the block, (2) the number of detection signals indicating medium foreign particles and exceeding the threshold for detection signals indicating medium foreign particles, i.e., the number of medium foreign particles in the block, (3) the number of detection signals indicating comparatively small foreign particles and exceeding the threshold for for detection signals indicating comparatively small foreign particles, i.e., the number of comparatively small foreign particles in the block, (4) the maximum detection signal and (5) the coordinates of the block.

These data for the block at the coordinates (5) stored in the storage device are read from the storage device sequentially to observe the foreign particles for confirmation. In some cases it is desirable to display all the data on a display.

The detection sensitivity of an apparatus that carries out binarization in detecting foreign particles, such as the reticle inspecting apparatus of the present invention, is greatly dependent on the thresholds, particularly, on the threshold for the detection signals indicating comparatively small foreign particles. If the threshold is excessively large, the apparatus fails to find comparatively small foreign particles. Failure in detecting comparatively small particles will cause no problem if the apparatus is applied to the detection of foreign particles in a process to monitor the soundness of the process on the basis of the variation of the number of foreign particles. However, failure in detecting even comparatively small foreign particles on a photomask, such as a reticle, causes serious problems in the products manufactured by using the photomask in the exposure and printing processes. Therefore, when the reticle inspecting apparatus must not fail in detecting even a single comparatively small foreign particles on the reticle. To ensure successful detection of comparatively small foreign particles, it is desirable to reduce the threshold for the detection signals to the smallest possible extent. If the threshold is excessively small, in some cases, normal portions of a circuit pattern are detected in mistake for defects, such as foreign particles. The present invention enables the operator to fetch detection data from the storage device to examine the detection data to see whether or not the detection data indicates a foreign particle and, if the detection data is the result of erroneous detection, to delete the detection data.

However, if the number of erroneously detected normal portions of the circuit pattern is very large (generally, the circuit patterns of most LSI circuits have millions of lines), the confirmation of the detection data requires a practically intolerable long time. Therefore, if the number of detection signals is excessively large (in such a case, most detection signals are those provided by the erroneous detection of normal portions of the circuit pattern), a new threshold larger than the threshold is set and the reticle inspection is repeated by using the new threshold, which, however requires additional time for repeating the reticle inspection. Therefore, it is desirable to employ a reticle inspecting method that repeats the inspection of a small inspection area requiring a short time to determine an appropriate threshold, and then starts the inspection of the entire area of the reticle after determining an appropriate threshold, a reticle inspecting method that decides that the threshold is inappropriate and interrupts the reticle inspecting operation when the number of detection signals increases beyond a predetermined value, a reticle inspecting method that interrupts the reticle inspecting operation when the number of detection signals increases beyond a predetermined value, increases the threshold by a predetermined value, and then restarts the reticle inspecting operation automatically, a reticle inspecting method that checks the number of detection signals provided in a fixed time interval, i.e., the rate of increase of the number of detection signals, and interrupts the reticle inspecting operation when the number of detection signals provided in the fixed time interval exceeds a predetermined value, or a reticle inspecting method that interrupts the reticle inspecting operation upon the increase of the number of detection signals provided in the fixed time interval beyond the predetermined value, increases the threshold by a predetermined value, and then restarts the reticle inspecting operation automatically. A latch 4201 shown in FIG. 32 is an important component to realize one of those reticle inspecting method.

It is also possible to store all the detection signals or the detection signals indicating defects, such as foreign particles, in the storage device, to set a threshold after the reticle has completely been inspected and to select the detection signals exceeding the threshold as those indicating foreign particles. This procedure, however, is unable to solve the problems imposed on the group processing circuit, such as "A large foreign particle is mistaken for a plurality of small foreign particles, and a long time is necessary for gaining access to and confirming the results of inspection." and "The grouping by software after the completion of inspection requires addition time.".

Therefore, the present invention displays and gains access to the results of detection of defects, such as foreign particles, in blocks, and uses the detection data of defects, such as foreign particles, obtained by the operation of the block processing circuit shown in FIG. 32, stored in the storage device and including (1) the number of detection signals exceeding the threshold for selecting comparatively large foreign particles (the number of comparatively large foreign particles), (2) the number of detection signals exceeding the threshold for selecting comparatively large foreign particles and medium foreign particles (the number of comparatively large particles and medium foreign particles), (3) the number of detection signals exceeding the threshold for selecting comparatively small foreign particles, medium foreign particles and comparatively large foreign particles (the number of comparatively small foreign particles, medium foreign particles and comparatively large foreign particles), (4) the maximum detection signal and (5) the coordinates of the blocks.

The number of blocks containing detection signals to be displayed and to be accessed can be reduced and can be carried out efficiently by gaining access to only the blocks containing detection signals exceeding the threshold for selecting medium foreign particles and comparatively large foreign particles or only the blocks containing detection signals exceeding the threshold for selecting comparatively large foreign particles. Although operation may be made for (1) to (3), the use of (4) is the quickest way of decision.

If (4) is used for decision, the detection signals need not be compared with the three ranks, i.e., the large rank, the medium rank and the small rank, and detection signals may be compared with an optional set value. The optional set value is changed (increased) gradually and changed (decreased) until the number of the blocks decreases to a value proper for access and confirmation when displaying the blocks, and then access to the blocks is gained, the inspection is carried out again by using the decreased set value as a new threshold, or the foregoing operation may be controlled by an automatic sequence control method.

Figure 33:
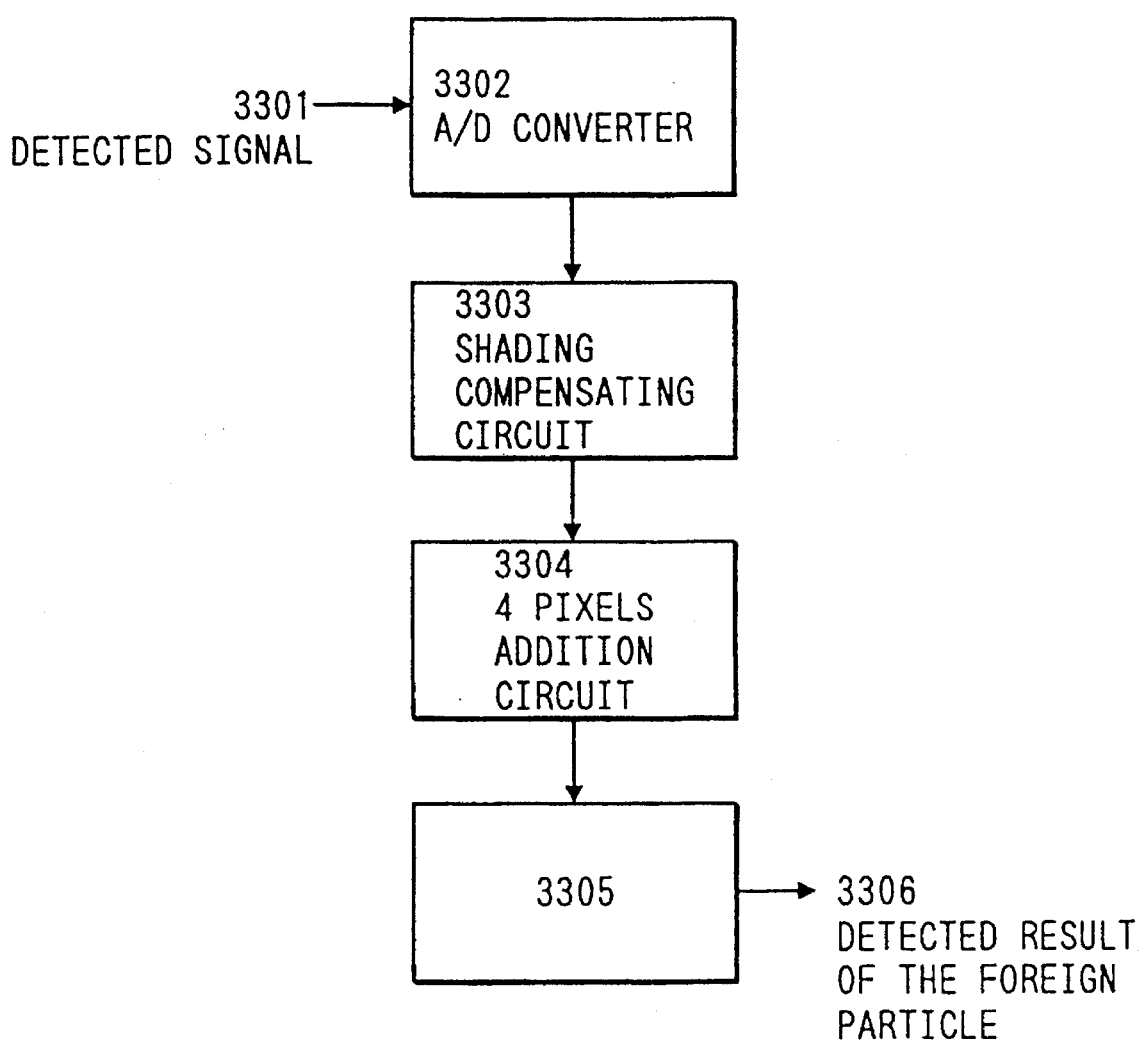
FIG. 33 is a block diagram showing the functional relation between a shading compensating circuit, a four-pixel addition circuit and a block processing circuit.

FIG. 33 shows the functional relation between detection signals 4101 and 4111 provided by the detectors, shading compensating circuits 113 and 123, four-pixel addition circuits 114 and 124, block processing circuits 58 and 558, and results of defect detection.

Figure 48:
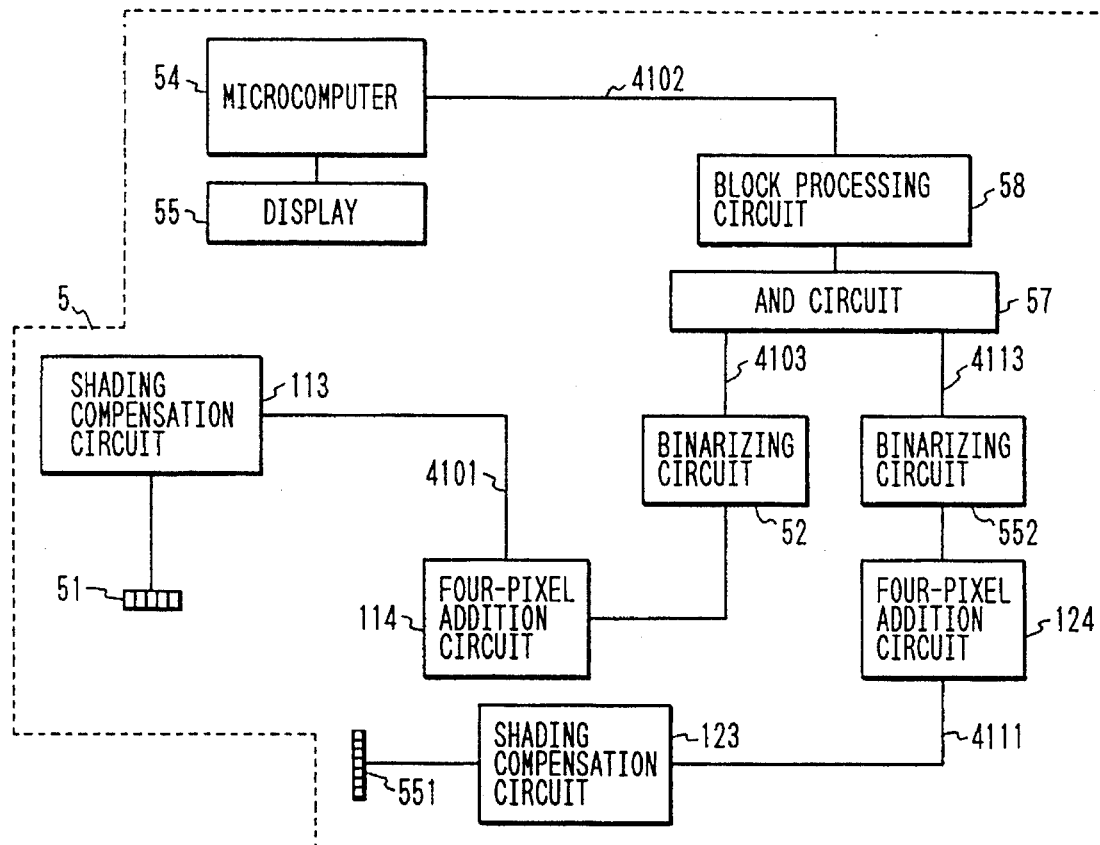
FIG. 48 is a block diagram of a signal processing unit in accordance with the present invention.
Figure 49:
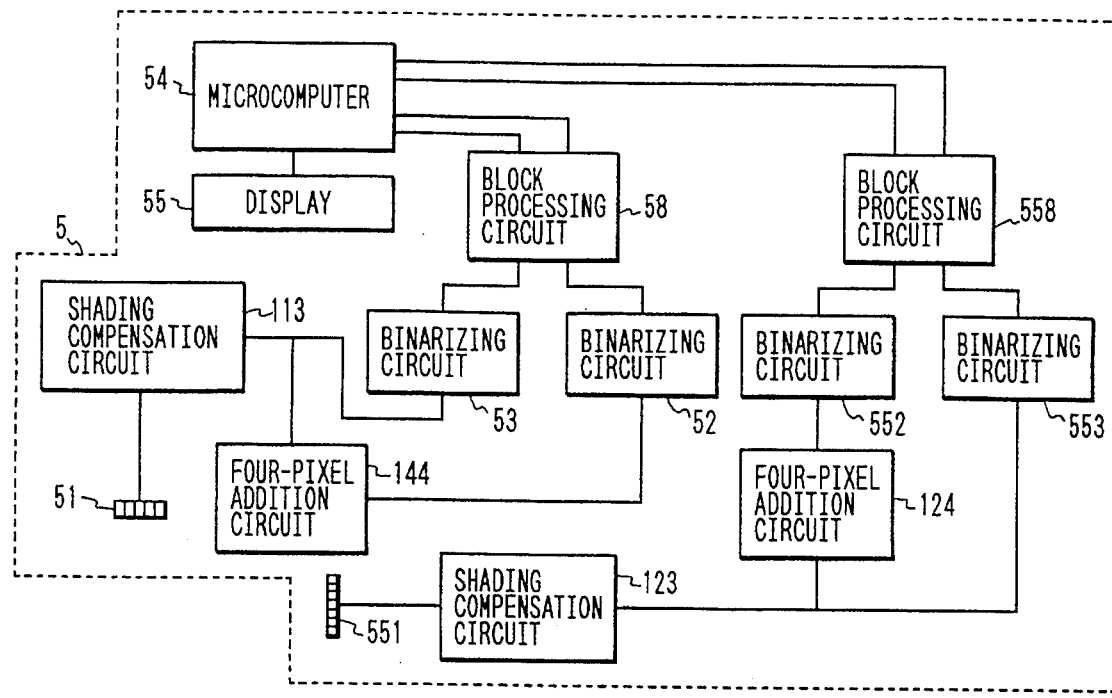
FIG. 49 is a block diagram of a signal processing unit in accordance with the present invention.
Figure 50:
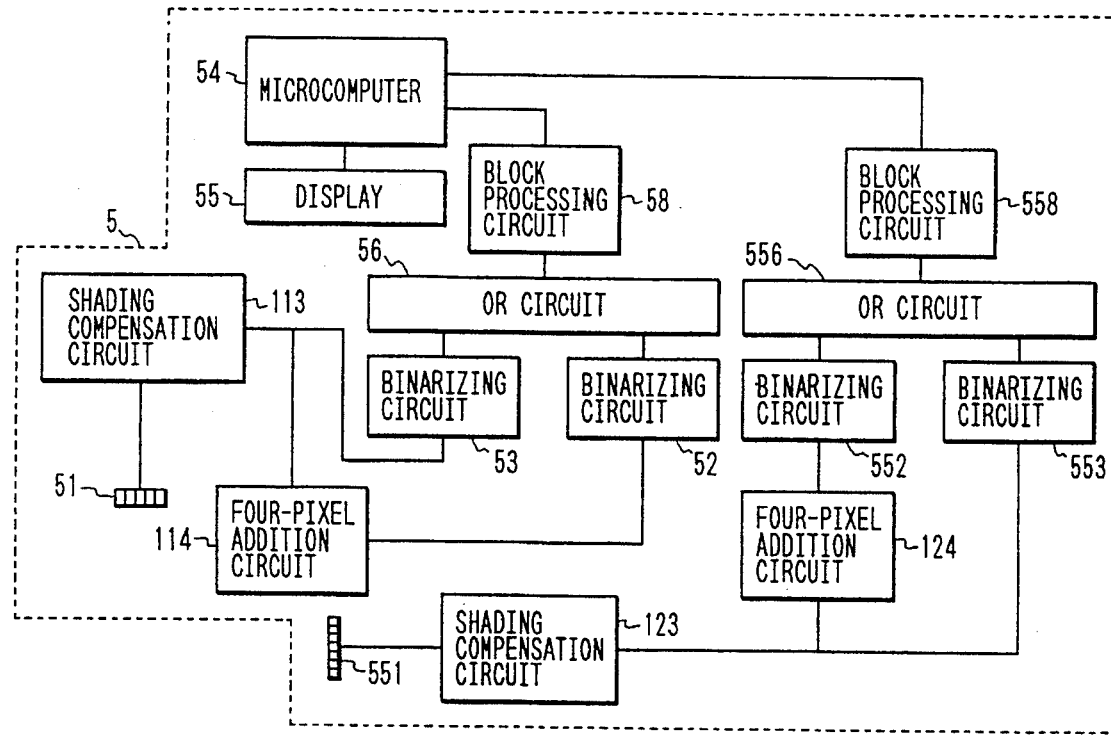
FIG. 50 is a block diagram of a signal processing unit in accordance with the present invention.
Figure 51:
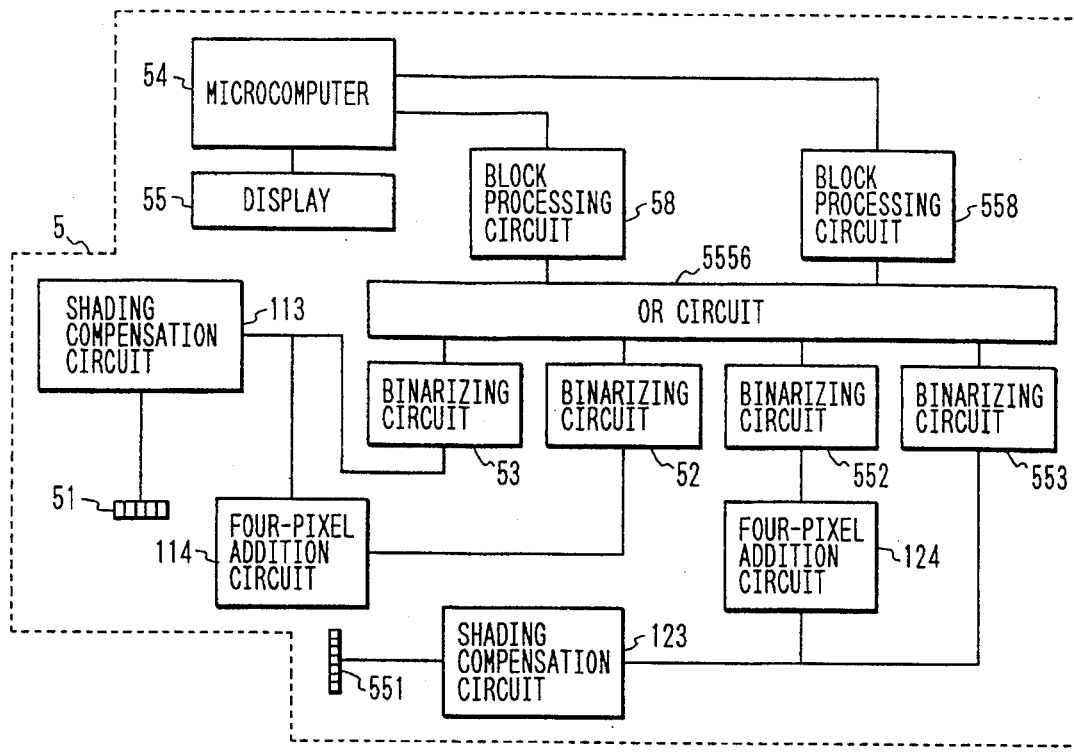
FIG. 51 is a block diagram of a signal processing unit in accordance with the present invention.
Figure 52:
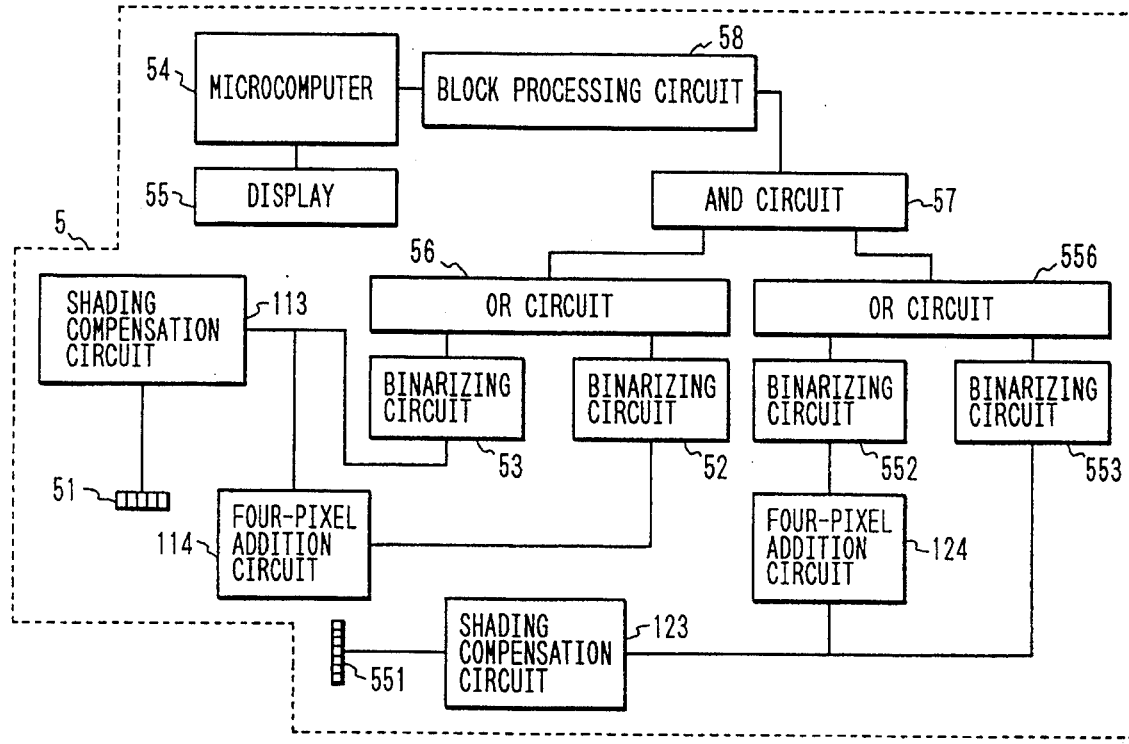
FIG. 52 is a block diagram of a signal processing unit in accordance with the present invention.
Figure 53:
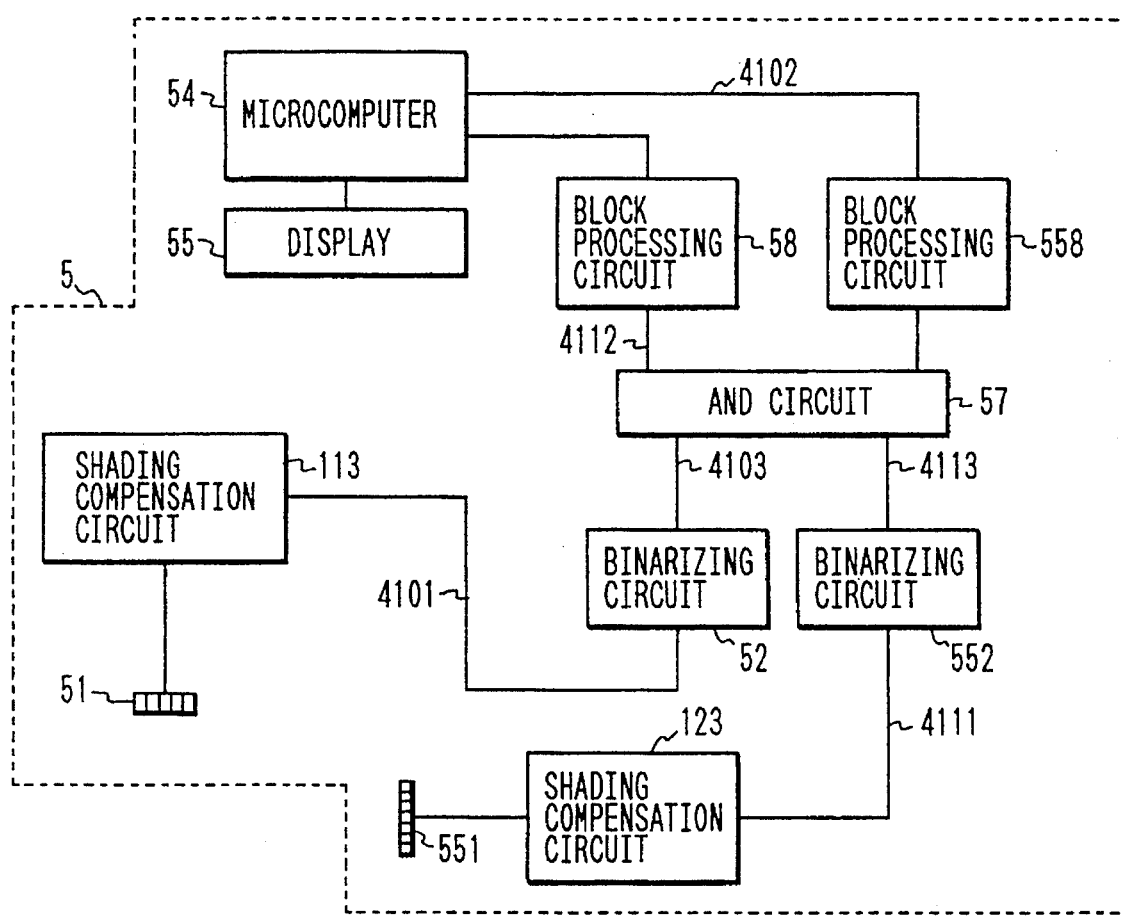
FIG. 53 is a block diagram of a signal processing unit in accordance with the present invention.

FIG. 48 shows a signal processing circuit formed by incorporating the shading compensating circuits 113 and 123, the four-pixel addition circuits 114 and 124 and the block processing circuits 58 and 558 into the signal processing circuit of FIG. 41. FIG. 49 shows a signal processing circuit formed by incorporating the shading compensating circuits 113 and 123, the four-pixel addition circuits 114 and 124 and the block processing circuits 58 and 558 into the signal processing circuit of FIG. 42. FIG. 50 shows a signal processing circuit formed by incorporating the shading compensating circuits 113 and 123, the four-pixel addition circuits 114 and 124 and the block processing circuits 58 and 558 into the signal processing circuit of FIG. 43. FIG. 51 shows a signal processing circuit formed by incorporating the shading compensating circuits 113 and 123, the four-pixel addition circuits 114 and 124 and the block processing circuits 58 and 558 into the signal processing circuit of FIG. 44. FIG. 52 shows a signal processing circuit formed by incorporating the shading compensating circuits 113 and 123, the four-pixel addition circuits 114 and 124 and the block processing circuits 58 and 558 into the signal processing circuit of FIG. 45, and FIG. 53 shows a signal processing circuit formed by incorporating the shading compensating circuits 113 and 123, the four-pixel addition circuits 114 and 124 and the block processing circuits 58 and 558 to the signal processing circuit of FIG. 46.

A reticle inspecting apparatus according to the present invention comprises a detection optical system provided with an optical system having NA of 0.4 or above, disposed on the front side of the reticle and capable of illuminating the front surface of a reticle obliquely with a front illuminating light beam of approximately 780 nm in wavelength, illuminating the back surface of the reticle obliquely with a back illuminating light beam of approximately 488 nm in wavelength, of concentrating scattered light, of separating the scattered light according to wavelength, a reticle, the reticle is washed perfectly in a washing of intercepting diffracted light diffracted by a circuit pattern formed on the front surface of the substrate of the reticle with spatial filters disposed on the Fourier transform planes and of focusing the separated scattered light on detectors; a correcting circuit capable of correcting errors, which are attributable to irregular illumination, in detection signals provided by the detectors; addition circuits for adding the outputs of 2×2 pixels of the corresponding detectors; and a circuit for selecting the maximum sum of detection signals from among four sums of detection signals obtained by shifting the detector by a distance corresponding to one pixel in four directions. Thus, defects, such as minute foreign particles of sizes on the submicron order adhering to the substrate provided with the circuit pattern, such as a photomask, particularly, a reticle provided with a phase shift film for improving printing resolution can be easily and stable discriminated from the circuit pattern by a simple optical system.

A photomask, such as a phase shift reticle, is fabricated by a photomask fabricating process shown in FIG. 65(A). A circuit pattern of a metal thin film and a phase shift film are formed on the front surface of a substrate in a circuit pattern forming step 651 to form a reticle, the reticle is washed perfectly in a washing step 652, and then the surface of the reticle is inspected for defects, such as foreign particles, by the reticle inspecting apparatus of the present invention in an inspecting step 653. If any detrimental foreign particles are found on the reticle, the reticle is washed and inspected again. This procedure is repeated until no foreign particle is found on the reticle.

After thus perfectly cleaning the reticle, pellicles for preventing the contamination of the reticle with foreign particles are attached to the reticle in a pellicle attaching step 654, and then the surfaces of the pellicles are inspected for foreign particles by the reticle inspecting apparatus of the present invention in an inspecting step 655. If any foreign particles are found, the pellicles are removed, the reticle is washed again, and then the pellicle attaching step 654, the inspecting step 655, removal of the pellicles and washing are repeated until no foreign particle is found on the reticle.

The perfect photomask, i.e., the perfect reticle, thus fabricated is delivered to an exposure process using a stepper.

Figure 66:
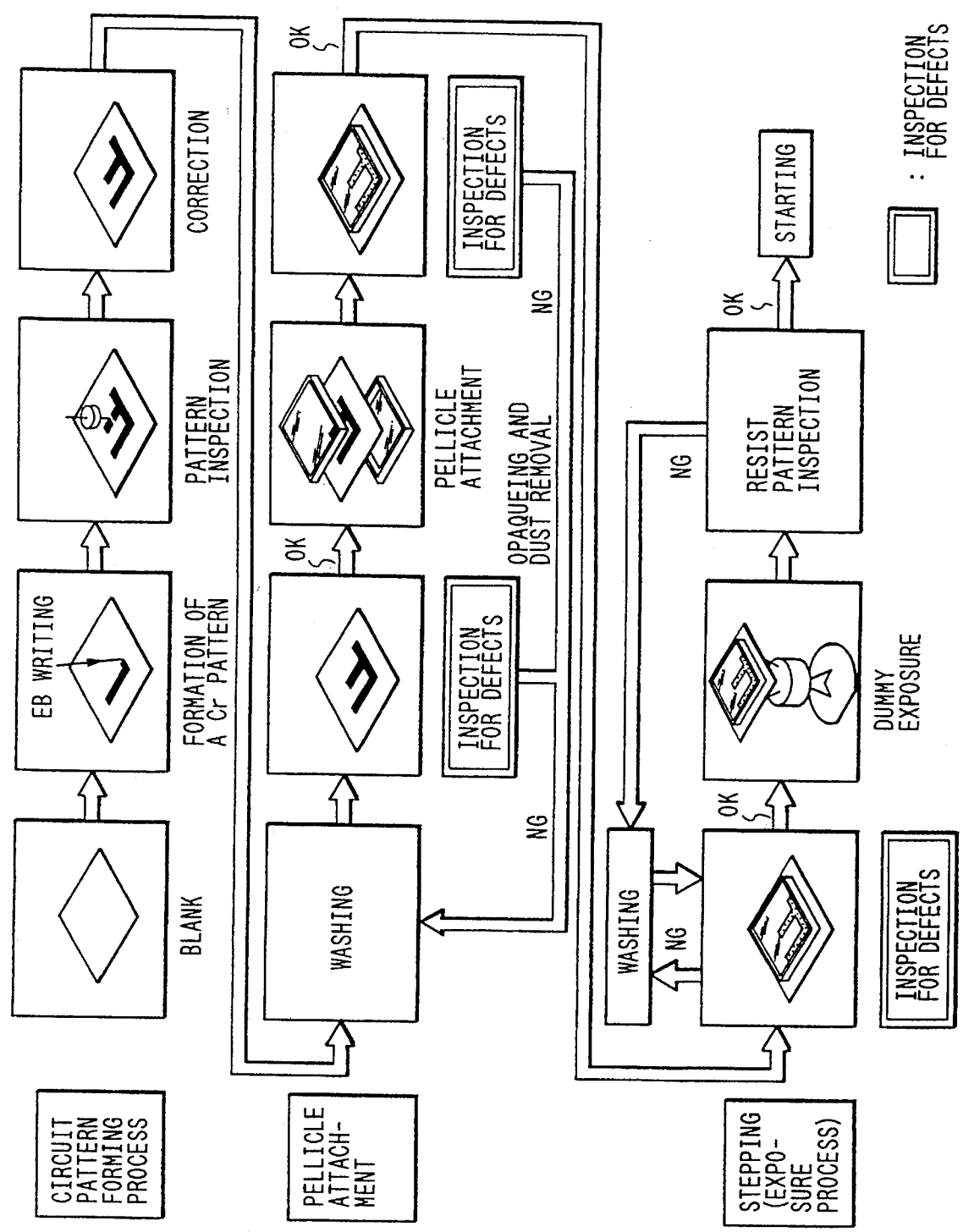
FIG. 66 is a block diagram of a reticle fabricating process in accordance with the present invention.

In a stepping projection process as shown in FIG. 65(B) using a stepper, a reticle is taken out from a stocker 656 storing reticles, and the reticle is inspected for foreign particles by the reticle inspecting apparatus of the present invention in an inspection step 657. If any foreign particle is found on the reticle, the reticle is returned to the reticle fabricating process, and the foreign particles are removed from the reticle by the reticle fabricating process. When no foreign particle is found on the reticle, the stepper carries out a dummy exposure step 658, the resist pattern formed on a wafer to be exposed to light transmitted by the reticle is inspected in a reticle error inspecting step 659 and, if the wafer is faultless, exposure and printing are carried out. FIG. 66 also shows the stepping projection process.

The reticle inspecting apparatus of the present invention is used in close systematic combination with the reticle fabricating process and the stepping projection process to supply perfect reticles perfectly free from defects, such as foreign particles, to semiconductor device fabricating processes for fabricating LSI circuits and the like.

What is claimed is:

1. A method of inspecting a reticle comprising a transparent or translucent substrate, a circuit pattern of an opaque film formed on a front surface of the substrate, and a pattern of a transparent or translucent film formed on the front surface of the substrate, said method comprising:

obliquely projecting a front illuminating light beam having a wavelength about 1.6 times of a smallest size of a foreign particle to be inspected on the reticle on the front surface of the substrate by a front illuminating system;

concentrating scattered light scattered by the front surface of the substrate and surfaces of the patterns formed on the front surface of the substrate;

obliquely projecting a back illuminating light beam having at least one wavelength about 1.0 times the smallest size of the foreign particle to be inspected on the reticle through a back surface of the substrate by a back illuminating system;

concentrating transmitted-and-diffracted light transmitted and diffracted by the substrate and the patterns formed on the front surface of the substrate;

intercepting the scattered light scattered by the patterns and the transmitted-and-diffracted light transmitted and scattered by the patterns with spatial filters disposed on Fourier transform planes;

focusing the scattered light and the transmitted-and-diffracted light transmitted by the spatial filters on detectors, respectively; and comparing a detection signal of the detector representing the scattered light and a detection signal of the detector representing the transmitted-and-diffracted light to see if there are any foreign particles adhering to the substrate.

2. A method of inspecting a reticle according to claim 1, wherein the reticle is provided with a phase shifter.

3. A method of inspecting a reticle according to claim 1, wherein the scattered light and the transmitted-and-diffracted light are concentrated by a focusing optical system disposed on a side of the front surface of the reticle with its optical axis extended substantially perpendicularly to the front surface of the substrate.

4. A method of inspecting a reticle according to claim 1, wherein a position on the front surface of the reticle is illuminated from a plurality of directions with the front illuminating light beam, and a position on the back surface of the reticle is illuminated from a plurality of directions with the back illuminating light beam.

5. A method of inspecting a reticle according to claim 1, wherein either the front illuminating light beam or the back illuminating light beam is used at a time.

6. A method of inspecting a reticle comprising a transparent or translucent substrate, a circuit pattern of an opaque film formed on a front surface of the substrate, and a pattern of a transparent or translucent film formed on the front surface of the substrate, said method comprising:

obliquely projecting a front illuminating light beam having a wavelength about 1.6 times of a smallest size of a foreign particle to be inspected on the reticle on the front surface of the substrate by a front illuminating system;

concentrating scattered light scattered by the front surface of the substrate and surfaces of the patterns formed on the front surface of the substrate;

obliquely projecting a back illuminating light beam having at least one wavelength about 1.0 times the smallest size of the foreign particle to be inspected on the reticle through a back surface of the substrate by a back illuminating system;

concentrating transmitted-and-diffracted light transmitted and diffracted by the substrate and the patterns formed on the front surface of the substrate;

separating the concentrated scattered light and the concentrated transmitted-and-diffracted light:

intercepting the scattered light scattered by the patterns and the transmitted-and-diffracted light transmitted and diffracted by the patterns with spatial filters disposed on Fourier transform planes;

focusing the scattered light and the transmitted-and-diffracted light transmitted by the spatial filters on a first detector and a second detector, respectively; and comparing detection signals provided by the first detector and the second detector to detect a defect including a foreign particle.

7. A method of inspecting a reticle according to claim 6, wherein the reticle is provided with a phase shifter.

8. A method of inspecting a reticle according to claim 6, wherein the scattered light and the transmitted-and-diffracted light are concentrated by a focusing optical system disposed on the side of the front surface of the reticle with its optical axis extended substantially perpendicularly to the front surface of the substrate.

9. A method of inspecting a reticle according to claim 6, wherein a position on the front surface of the reticle is illuminated from a plurality of directions with the front illuminating light beam, and a position on the back surface of the reticle is illuminated from a plurality of directions with the back illuminating light beam.

10. A method of inspecting a reticle according to claim 6, wherein the wavelength of the front illuminating light beam is in a range of 600 to 800 nm, and the wavelength of the back illuminating light beam is in a range of 450 to 550 nm.

11. A method of inspecting a reticle according to claim 10, wherein the wavelength of the front illuminating light beam is about 780 nm and the wavelength of the back illuminating light beam is one of about 488 nm and about 515 nm.

12. A projection exposure method comprising:

a reticle inspecting process for inspecting a phase shift reticle comprising a transparent or translucent substrate, a circuit pattern of an opaque film formed on a front surface of the substrate and a pattern of a transparent or translucent film formed on the front surface of the substrate, and contamination preventing devices each comprising a frame and a transparent thin film held on the frame, and put on the front surface and a back surface of the substrate, respectively, comprising:

obliquely projecting a front illuminating light beam having a wavelength about 1.6 times of a smallest size of a foreign particle to be inspected on the reticle on the front surface of the substrate by a front illuminating system, concentrating scattered light scattered by the front surface of the substrate and surfaces of the patterns formed on the front surface of the substrate, obliquely projecting a back illuminating light beam having at least one wavelength about 1.0 times the smallest size of the foreign particle to be inspected on the reticle through the back surface of the substrate by a back illuminating system, concentrating transmitted-and-diffracted light transmitted and diffracted by the substrate and the patterns formed on the front surface of the substrate, intercepting the scattered light scattered by the patterns and the transmitted-and-diffracted light transmitted and diffracted by the patterns with spatial filters disposed on Fourier transform planes, focusing the scattered light and the transmitted-and-diffracted light transmitted by the spatial filters on a first detector and a second detector, respectively, and comparing a detection signal provided by the first detector and a detection signal provided by the second detector to see if there are any foreign particles adhering to the substrate;

a conveying process for conveying the phase shift reticle provided with the contamination preventing devices, inspected by the reticle inspecting process and proved to be free from foreign particles to a projection exposure apparatus and locating the phase shift reticle at a predetermined exposure position; and an exposure process for projecting exposure light through the phase shift reticle located at the exposure position toward a wafer and focusing the exposure light transmitted by the phase shift reticle on the wafer by a focusing optical system, which changes a phase of the light transmitted by the circuit pattern of the transparent or translucent film to prevent interference, to print an image of the pattern of the opaque film of the phase shift reticle on the wafer 13. A projection exposure method comprising:

a reticle inspecting process for inspecting a phase shift reticle comprising a transparent or translucent substrate, a circuit pattern of an opaque film formed on a front surface of the substrate and a pattern of a transparent or translucent film formed on the front surface of the substrate, comprising:

obliquely projecting a front illuminating light beam having a wavelength about 1.6 times of a smallest size of a foreign particle to be inspected on the reticle on the front surface of the substrate by a front illuminating system, concentrating scattered light scattered by the front surface of the substrate and surfaces of the patterns formed on the front surface of the substrate, obliquely projecting a back illuminating light beam having at least one wavelength about 1.0 times the smallest size of the foreign particle to be inspected on the reticle through the back surface of the substrate by a back illuminating system, concentrating transmitted-and-diffracted light transmitted and diffracted by the substrate and the patterns formed on the front surface of the substrate, separating the concentrated scattered light and the concentrated transmitted-and-diffracted light, intercepting the scattered light scattered by the patterns and the transmitted-and-diffracted light transmitted and diffracted by the patterns with spatial filters disposed on Fourier transform planes, respectively, focusing the scattered light and the transmitted-and-diffracted light transmitted by the spatial filters on a first detector and a second detector, respectively, and comparing a detection signal provided by the first detector and a detection signal provided by the second detector to see if there are any foreign particles adhering to the substrate;

a conveying process for conveying the phase shift reticle inspected by the reticle inspecting process and proved to be free from foreign particles to a projection exposure apparatus and locating the phase shift reticle at a predetermined exposure position; and an exposure process for projecting exposure light through the phase shift reticle located at the exposure position toward a wafer and focusing the exposure light transmitted by the phase shift reticle on the wafer by a focusing optical system, which changes a phase of the light transmitted by the circuit pattern of the transparent or translucent film to prevent interference, to print an image of the pattern of the opaque film of the phase shift reticle on the wafer.

14. A projection exposure method comprising:

a first reticle inspecting process for inspecting a phase shift reticle comprising a transparent or translucent substrate, a circuit pattern of an opaque film formed on a front surface of the substrate and a pattern of a transparent or translucent film formed on the front surface of the substrate, comprising:

obliquely projecting a front illuminating light beam having a wavelength about 1.6 times of a smallest size of a foreign particle to be inspected on the reticle on the front surface of the substrate by a front illuminating system, concentrating scattered light scattered by the front surface of the substrate and surfaces of the patterns formed on the front surface of the substrate, obliquely projecting a back illuminating light beam having at least one wavelength about 1.0 times the smallest size of the foreign particle to be inspected on the reticle through the back surface of the substrate by a back illuminating system, concentrating transmitted-and-diffracted light transmitted and diffracted by the substrate and the patterns formed on the front surface of the substrate, separating the concentrated scattered light and the concentrated transmitted-and-diffracted light, intercepting the scattered light scattered by the patterns and transmitted-and-diffracted light transmitted and diffracted by the patterns with spatial filters disposed on Fourier transform planes, respectively, focusing the scattered light and the transmitted-and-diffracted light transmitted by the spatial filters on a first detector and a second detector, respectively, and comparing a detection signal provided by the first detector and a detection signal provided by the second detector to see if there are any foreign particles adhering to the substrate;

a contamination preventing device attaching process for attaching contamination preventing devices each comprising a frame and a transparent thin film held on the frame to the front surface and the back surface, respectively, of the substrate of the phase shift reticle inspected by the first reticle inspecting process and proved to be free from foreign particles;

a second reticle inspecting process comprising:

obliquely projecting a front illuminating light beam through the transparent thin film of the contamination preventing device on the front surface of the substrate by the front illuminating system, concentrating scattered light scattered by the front surface of the substrate and the surfaces of the patterns formed on the front surface of the substrate, and traveling through the transparent thin film of the contamination preventing device, obliquely projecting a back illuminating light beam through the transparent thin film of the contamination preventing device on the back surface of the substrate by the back illuminating system, concentrating transmitted-and-diffracted light transmitted and diffracted by the substrate and the patterns formed on the front surface of the substrate, and traveling through the transparent thin film of the contamination preventing device, separating the concentrated scattered light and the concentrated transmitted-and-diffracted light, intercepting the scattered light scattered by the patterns and the transmitted-and-diffracted light transmitted and diffracted by the patterns with the spatial filters disposed on Fourier transform planes, respectively, focusing the scattered light and the transmitted-and-diffracted light transmitted by the spatial filters on the first detector and the second detector, respectively, and comparing a detection signal provided by the first detector and a detection signal provided by the second detector to see if there are any foreign particles adhering to the substrate;

a conveying process for conveying the phase shift reticle inspected by the second reticle inspecting process and proved to be free from foreign particles to a projection exposure apparatus and locating the phase shift reticle at a predetermined exposure position;

an exposure process for projecting exposure light through the phase shift reticle located at the exposure position toward a wafer and focusing the exposure light transmitted by the phase shift reticle on the wafer by a focusing optical system, which changes a phase of the light transmitted by the circuit pattern of the transparent or translucent film to prevent interference, to print an image of the pattern of the opaque film of the phase shift on the wafer.

15. A reticle inspecting apparatus for inspecting a reticle comprising a transparent or translucent substrate, a pattern of an opaque film formed on a front surface of the substrate, and a pattern of a transparent or translucent film formed on the front surface of the substrate, said reticle inspecting apparatus comprising:

a front illuminating system for obliquely projecting a front illuminating light beam having a wavelength about 1.6 times of a smallest size of a foreign particle to be inspected on the reticle on the front surface of the substrate;

a back illuminating system for obliquely projecting a back illuminating light beam having at least one wavelength about 1.0 times the smallest size of the foreign particle to be inspected on the reticle through a back surface of the substrate;

a focusing optical system for concentrating and focusing scattered light, which is part of the front illuminating light beam scattered by the front surface of the substrate and the surfaces of the patterns, and transmitted-and-diffracted light, which is part of the back illuminating light beam transmitted and diffracted by the substrate and the patterns;

spatial filters disposed on Fourier transform planes to intercept the scattered light scattered by the patterns and the transmitted-and-diffracted light transmitted and diffracted by the patterns, respectively;

detectors for receiving the scattered light and the transmitted-and-diffracted light transmitted by the spatial filters, and for providing detection signals representing the received scattered light and the received transmitted-and-diffracted light, respectively; and a comparing means for comparing a detection signal provided by the detector and representing the received scattered light, and a detection signal provided by the detector and representing the received transmitted-and-diffracted light to determine if there are any foreign particles on the reticle.

16. A reticle inspecting apparatus according to claim 15, wherein the reticle is a phase shift reticle provided with a phase shifter.

17. A reticle inspecting apparatus according to claim 15, wherein the focusing optical system is disposed on the side of the front surface of the reticle with its optical axis extended perpendicularly to the front surface of the substrate.

18. A reticle inspecting apparatus according to claim 15, wherein the front illuminating system is capable of illuminating a position on the surface of the substrate from a plurality of directions with the front illuminating light beam and the back illuminating system is capable of illuminating one position on the back surface of the substrate from a plurality of directions with the back illuminating light beam.

19. A reticle inspecting apparatus according to claim 15, wherein the front illuminating system has two front illuminating units, the back illuminating system has two back illuminating units, and a switching means selects either of the two front illuminating units and either of the back illuminating units for enabling inspection.

20. A reticle inspecting apparatus for inspecting a reticle comprising a transparent or translucent substrate, a pattern of an opaque film formed on a front surface of the substrate, and a pattern of a transparent or translucent film formed on the front surface of the substrate, said reticle inspecting apparatus comprising:

a front illuminating system for obliquely projecting a front illuminating light beam having a wavelength about 1.6 times of a smallest size of a foreign particle to be inspected on the reticle on the front surface of the substrate;

a back illuminating system for obliquely projecting a back illuminating light beam having at least one wavelength about 1.0 times the smallest size of the foreign particle to be inspected on the reticle through a back surface of the substrate;

a focusing optical system for concentrating and focusing scattered light, which is part of the front illuminating light beam scattered by the surface of the substrate and surfaces of the patterns, and transmitted-and-diffracted light, which is part of the back illuminating light beam transmitted and diffracted by the substrate and the patterns;

a separating optical system for separating the scattered light and the transmitted-and-diffracted light concentrated by the focusing optical system;

a first spatial filter and a second spatial filter disposed on Fourier transform planes to intercept the scattered light scattered by the patterns and the transmitted-and-diffracted light transmitted and diffracted by the patterns, respectively;

a first detector and a second detector for receiving the scattered light and the transmitted-and-diffracted light transmitted by the first and second spatial filter and focused by the focusing optical system and for converting the respective intensities of the received scattered light and the received transmitted-and-diffracted light into corresponding detection signals, respectively; and a comparing means for comparing a detection signal provided by the first detector and representing the received scattered light, and a detection signal provided by the second detector and representing the received transmitted-and-diffracted light to determine if there are any foreign particles on the reticle.

21. A reticle inspecting apparatus according to claim 20, wherein the reticle is a phase shift reticle provided with phase shifter.

22. A reticle inspecting apparatus according to claim 20, wherein the focusing optical system is disposed on the side of the front surface of the reticle with its optical axis extended perpendicularly to the front surface of the substrate.

23. A reticle inspecting apparatus according to claim 20, wherein the front illuminating system is capable of illuminating a position on the front surface of the substrate from a plurality of directions, and the back illuminating system is capable of illuminating a position on the back surface of the substrate from a plurality of directions.

24. A reticle inspecting apparatus according to claim 20, wherein the wavelength of the front illuminating light beam is in a range of 600 to 800 nm and that of the back illuminating light beam is in a range of 450 to 550 nm.

25. A reticle inspecting apparatus according to claim 24, wherein the wavelength of the front illuminating light beam is about 780 nm and the wavelength of the back illuminating light beam is one of about 488 nm and about 515 nm.

26. A projection exposure apparatus comprising:

a reticle inspecting means for inspecting a phase shift reticle provided with a phase shifter and comprising a transparent or translucent substrate, a circuit pattern of an opaque film formed on a front surface of the substrate, a pattern of a transparent or translucent film formed on the front surface of the substrate, and contamination preventing devices each comprising a frame and a transparent thin film held on the frame, and attached to the front surface and back surface of the substrate, respectively, by obliquely projecting a front illuminating light beam having a wavelength about 1.6 times of a smallest size of a foreign particle to be inspected on the reticle through the transparent thin film on the front surface of the substrate by a front illuminating system, concentrating scattered light scattered by the front surface of the substrate and the surfaces of the patterns and traveling through the transparent thin film, obliquely projecting a back illuminating light beam having at least one wavelength about 1.0 times the smallest size of the foreign particle to be inspected on the reticle through the transparent thin film on the back surface of the substrate, concentrating transmitted-and-diffracted light transmitted and diffracted by the substrate and the patterns and traveling through the transparent thin film, separating the concentrated scattered light and the concentrated transmitted-and-diffracted light, intercepting the scattered light scattered by the patterns and the transmitted-and-diffracted light transmitted and diffracted by the patterns with spatial filters disposed on Fourier transform planes, respectively, focusing the scattered light and the transmitted-and-diffracted light transmitted by the spatial filters on a first detector and a second detector, respectively, and comparing a detection signal provided by the first detector and a detection signal provided by the second detector to see if there are any foreign particles on the reticle;

a conveying means for conveying the phase shift reticle provided with the contamination preventing devices, inspected by the reticle inspecting means and proved to be free from foreign particles to and locating the same at a predetermined exposure position; and a projection exposure means for projecting exposure light through the phase shift reticle provided with the contamination preventing devices and located at the exposure position toward a wafer and focusing the exposure light transmitted by the phase shift reticle on the wafer by a focusing optical system, which changes a phase of the light transmitted by the circuit pattern of the transparent or translucent film to prevent interference, to print an image of the pattern of the opaque film of the phase shift reticle on the wafer.

27. A projection exposure apparatus comprising:

a reticle inspecting means for inspecting a phase shift reticle provided with a phase shifter and comprising a transparent or translucent substrate, a circuit pattern of an opaque film formed on a front surface of the substrate and a pattern of a transparent or translucent film formed on the front surface of the substrate by obliquely projecting a front illuminating light beam having a wavelength about 1.6 times of a smallest size of a foreign particle to be inspected on the reticle on the front surface of the substrate by a front illuminating system, concentrating scattered light scattered by the front surface of the substrate and the surfaces of the patterns, obliquely projecting a back illuminating light beam having at least one wavelength about 1.0 times the smallest size of the foreign particle to be inspected on the reticle through a back surface of the substrate by a back illuminating system, concentrating transmitted-and-diffracted light transmitted and diffracted by the substrate and the patterns, separating the concentrated scattered light and the concentrated transmitted-and-diffracted light, intercepting the scattered light scattered by the patterns and the transmitted-and-diffracted light transmitted and diffracted by the patterns with spatial filters disposed on Fourier transform planes, respectively, focusing the scattered light and the transmitted-and-diffracted light transmitted by the spatial filters on a first detector and a second detector, and comparing a detection signal provided by the first detector and a detection signal provided by the second detector to see if there are any foreign particles on the reticle;

a conveying means for conveying the phase shift reticle inspected by the reticle inspecting means and proved to be free from foreign particles to and locating the same at a predetermined exposure position; and a projection exposure means for projecting exposure light through the phase shift reticle located at the exposure position toward a wafer and focusing the exposure light transmitted by the phase shift reticle on the wafer by a focusing optical system, which changes a phase of the light transmitted by the circuit pattern of the transparent or translucent film to prevent interference, to print an image of the pattern of the opaque film on the wafer.

28. A projection exposure apparatus comprising:

a reticle inspecting means for inspecting a phase shift reticle provided with a phase shifter and comprising a transparent or translucent substrate, a circuit pattern of an opaque film formed on a front surface of the substrate and a pattern of a transparent or translucent film formed on the front surface of the substrate, before and after attaching contamination preventing devices to the reticle, by obliquely projecting a front illuminating light beam on having a wavelength about 1.6 times of a smallest size of a foreign particle to be inspected on the reticle the front surface of the substrate, concentrating scattered light scattered by the surface of the substrate and surfaces of the patterns, obliquely projecting back illuminating light beam having at least one wavelength about 1.0 times the smallest size of the foreign particle to be inspected on the reticle through a back surface of the substrate by a back illuminating system, concentrating transmitted-and-diffracted light transmitted and diffracted by the substrate and the patterns, separating the concentrated scattered light and the concentrated transmitted-and-diffracted light, intercepting the scattered light scattered by the patterns and the transmitted-and-diffracted light transmitted and diffracted by the patterns with spatial filters disposed on Fourier transform planes, respectively, focusing the scattered light and the transmitted-and-diffracted light transmitted by the spatial filters on a first detector and a second detector, respectively, and comparing a detection signal provided by the first detector and a detection signal provided by the second detector to see if there are any foreign particles on the reticle;

a conveying means for conveying the phase shift reticle provided with contamination preventing devices, inspected by the reticle inspecting means and proved to be free from foreign particles to and locating the same at a predetermined exposure position; and a projection exposure means for projecting exposure light through the phase shift reticle provided with contamination preventing devices and located at the exposure position toward a wafer and focusing the exposure light transmitted by the phase shift reticle on the wafer by a focusing optical system, which changes a phase of the light transmitted by the pattern of the transparent or translucent film to prevent interference, to print an image of the circuit pattern of the opaque film of the reticle on the wafer.

\* \* \* \* \*